(12) United States Patent
Tsuna et al.

(10) Patent No.: US 12,163,195 B2
(45) Date of Patent: Dec. 10, 2024

(54) LISTERIA-MONOCYTOGENES DETECTION METHOD

(71) Applicants: NIPPN CORPORATION, Tokyo (JP); FASMAC CO., LTD., Atsugi (JP)

(72) Inventors: Mika Tsuna, Atsugi (JP); Yoshitaka Harada, Atsugi (JP); Yasuhiro Seto, Atsugi (JP); Kazuto Takasaki, Atsugi (JP)

(73) Assignees: NIPPN CORPORATION, Tokyo (JP); FASMAC CO., LTD., Atsugi (JP)

( * ) Notice: Subject to any disclaimer, the term of this patent is extended or adjusted under 35 U.S.C. 154(b) by 0 days.

(21) Appl. No.: 18/505,697

(22) Filed: Nov. 9, 2023

(65) Prior Publication Data

US 2024/0167104 A1 May 23, 2024

Related U.S. Application Data

(62) Division of application No. 16/632,051, filed as application No. PCT/JP2017/045280 on Dec. 18, 2017.

(30) Foreign Application Priority Data

Jul. 20, 2017 (JP) ................... 2017-141201

(51) Int. Cl.
| | | |
|---|---|---|
| C12Q 1/689 | (2018.01) | |
| C12Q 1/6853 | (2018.01) | |
| C12Q 1/686 | (2018.01) | |
| C12Q 1/6869 | (2018.01) | |
| G01N 33/52 | (2006.01) | |

(52) U.S. Cl.
CPC ........... *C12Q 1/689* (2013.01); *C12Q 1/6853* (2013.01); *C12Q 1/686* (2013.01); *C12Q 1/6869* (2013.01); *G01N 33/52* (2013.01); *C12Q 2600/156* (2013.01); *G01N 2458/00* (2013.01); *G01N 2469/00* (2013.01)

(58) Field of Classification Search
CPC .............................. C12Q 1/689; C12Q 1/6853
See application file for complete search history.

(56) References Cited

U.S. PATENT DOCUMENTS

2006/0257894 A1 11/2006 Doumith et al.
2021/0024979 A1 1/2021 Tsuna et al.

FOREIGN PATENT DOCUMENTS

| JP | 2007-61061 A | 3/2007 |
|---|---|---|
| JP | 2010/0263873 A | 11/2010 |
| JP | 2018-57363 A | 4/2018 |
| WO | WO 2019/016976 A1 | 1/2019 |

OTHER PUBLICATIONS

Wu, R., et al. Development of double loop-mediated isothermal amplification to detect Listeria monocytogenes in food, 2014, Curr Microbiol, 69:839-845 (Year: 2014).*
Cho, A-R, et al. Development of a loop-mediated isothermal amplification assay for detecting Listeria monocytogenes prfA in milk; 2014, Food Sci Biotech 23(2):467-474 (Year: 2014).*
Deng et al., "Probing the pan-genome of Listeria monocytogenes: new insights into intraspecific niche expansion and genomic diversification," BMC Genomics (2010), vol. 11, No. 500, pp. 1-21.
English translation of International Preliminary Report on Patentability and Written Opinion mailed Jan. 30, 2020, in PCT/JP2017/045280.
English translation of International Search Report mailed Mar. 13, 2018, in PCT/JP2017/045280.
Notification No. 1128, Article 2 of the Department of Food Safety, "Examination of Listeria monocytogenes", Nov. 28, 2014.
Paul et al., "Genome comparison of Listeria Monocytogenes serotype 4a strain HCC23 with selected lineage I and lineage II L. monocytogenes strains and other Listeria strains," Genomics Data (2014), vol. 2, pp. 219-225.
Tan et al., "Development of ListeriaBase and comparative analysis of Listeria monocytogenes," BMC Genomics (2015), vol. 16, No. 755, pp. 1-19.
Tao et al., "Mining of novel species-specific primers for POR detection of Listeria monocytogenes based on genomic approach," World J. Microbiol. Biotechnol. (2015), vol. 31, pp. 1955-1966.
Tsuna et al., "Development of simple method for detection of Listeria monocytogenes," Abstracts of the 38th Annual Meeting of Japanese Society of Food Microbiology. Aug. 31, 2017.
Tsuna et al., "Development of simple method for detection of Listeria monocytogenes," Poster Session, The 38th Annual Meeting of Japanese Society of Food Microbiology, Oct. 5-6, 2017.

* cited by examiner

Primary Examiner — Samuel C Woolwine
Assistant Examiner — Lisa Horth
(74) *Attorney, Agent, or Firm* — Birch, Stewart, Kolasch & Birch, LLP

(57) ABSTRACT

Novel means that enables detection of the *monocytogenes* bacterium alone distinctly from other bacteria belonging to the genus *Listeria* with sufficiently high accuracy is disclosed. The present inventors intensively analyzed the genome of the *monocytogenes* bacterium to identify two genes (the lmo0084 gene and the lmo2736 gene) as target regions with which the *monocytogenes* bacterium can be specifically detected distinctly from other bacteria belonging to the genus *Listeria* utilizing a nucleic acid amplification method. By a further intensive study of the base sequences of these two genes, primer setting regions for highly accurate, specific detection of the *monocytogenes* bacterium alone were identified, and preferred particular examples of PCR primer sets, LAMP primer sets, and real-time PCR primer-probe sets were established.

2 Claims, 3 Drawing Sheets
Specification includes a Sequence Listing.

Primer set No. 4  Forward Primer: lmo00084 F281A
Reverse Primer: lmo00084 R757B
PCR product size: 476 bp Primer set No. 1  Forward Primer: lmo02736_F8
Reverse Primer: lmo02736_R176
PCR product size: 168 bp

SEQUENCE LISTING

```
Sequence total quantity: 86
SEQ ID NO: 1              moltype = DNA   length = 983
FEATURE                   Location/Qualifiers
source                    1..983
                          mol_type = genomic DNA
                          organism = Listeria monocytogenes
SEQUENCE: 1
atgaaaaaga gacaattagg aaatgctggc ttagttactt cagagcttgg attcggctgt   60
atggggctaa attatcatcg tggacctgcg aaagatcgaa atgaaatgat tgaagtcgta  120
cgcactgcaa tggatgcagg gattacgatg ttcgatacag ctgaagtgta tggacccttat 180
actaacgaag aacttgtcgg agaagcttta gttggcaaaa gaaaccatgt tcaaatcgca  240
acaaaaggtg gttttaaaat taatggttta aataacgaag tcgatagccg tccagaaagc  300
atcaaggccg cggttgaagg ctctctcaaa cggctaaaaa cagattacat tgatttatat  360
tacattcata gaattgaccc ctctatccca attgaagagg ttgccggcac cattcagaat  420
ttaaaacaag aagggaaaat tctacactgg ggactctccg aagccagcgc aaagacaata  480
cgccgtgctc ataaagtaga gccactagct gcggttgaaa gtgagtattc tatctggtgg  540
cgagaagctg aaaaagaagt attcccggtt ttagaagaac ttggcatcgg cttgtcgca   600
tacagcccac taggtcgtgg ttatttaact ggaaaattag atataaatgc tgacttcaat  660
gcaaacgaca accgtggtgg cttaccaaga ttccaaaaag aagccatgga agccaaccaa  720
gtactactag atttcatgaa agaaatcgcc gacgagcaaa acgtcacaac agcccaactt  780
gccctcgctt ggatacttga ccaaaaacct tggatcgtgc caattcccgg aacaacaaga  840
ccaagcagaa tggaagaaaa tatcgcctcc actgaaattc attttgatga tggagcacga  900
caaaaaatag ctgatgcttt atcgcagatt gaaattgttg gtgatagata ctcagccgcc  960
gaaaataaac gtatcggaaa ata                                          983

SEQ ID NO: 2              moltype = DNA   length = 983
FEATURE                   Location/Qualifiers
source                    1..983
                          mol_type = genomic DNA
                          organism = Listeria monocytogenes
SEQUENCE: 2
atgaaaaaga gacaattagg aaacactggt ttagtaactt cagagcttgg attcggctgt   60
atgggactca attatcaccg gggacctgcg aaagatagaa aagaaatgat tgaagtcgta  120
cgcactgcaa tggatgcagg gattacgatg ttcgatactg ctgaagtgta cggacccttat 180
actaatgaag aacttgtcgg agaagcttta gttggcaaaa gaaaccatgt tcaaattgca  240
acaaaaggtg gttttaaaat taatggttta aataacgaag tcgatagccg tccagaaagc  300
atcaaggccg cggttgaagg ctctctcaaa cggctaaaaa cggattacat tgatttatat  360
tacattcata gaattgaccc ctctatccca attgaagagg ttgccggaac cattcagaat  420
ttaaaacaag aaggaaaaat tctacactgg ggactttccg aagccagcgc aaagacaata  480
cgccgtgctc ataaagtaga gccactagct gctgttgaaa gtgagtattc catctggtgg  540
cgagaagctg aaaaagaaat atttccggtt ttagaagaac ttggcatcgg cttgtcgca   600
tacagcccac taggtcgcgg ttatttaact ggcaaattgg atataaatgc tagcttcaat  660
gaaaacgaca accgcggtgg cttaccaaga ttccaaaaag aagccatgga agccaaccaa  720
gtactactcg attttatgaa agaaatagcc gacgagcaaa atgtcacaac agcacaactc  780
gccatcgctt ggatacttga ccaaaaacct tggatcgtgc caattcccgg aacaacaaaa  840
caaagcagaa ttaagaaaaa tatcgcctcc acggacattc gttttgatga cggagcacga  900
caaaaaatag ctgatgcttt atcgcagatt gaaattgttg gtgatagata ctcagcagct  960
gaaaataaac gcatcggaaa gta                                          983

SEQ ID NO: 3              moltype = DNA   length = 984
FEATURE                   Location/Qualifiers
source                    1..984
                          mol_type = genomic DNA
                          organism = Listeria monocytogenes
SEQUENCE: 3
atgaaaaaga gacaattagg aaatgctggc ttagttactt cagagcttgg attcggctgt   60
atggggctaa attatcatcg tggacctgcg aaagatcgaa atgaaatgat tgaagtcgta  120
cgcactgcaa tggatgcagg gattacgatg ttcgatacag ctgaagtgta tggacccttat 180
actaacgaag aacttgtcgg agaagctttg gttggcaaaa gaaaccatgt tcaaatcgca  240
acaaaaggtg gttttaaaat taatggttta aataacgaag tcgatagccg tccagaaagc  300
atcaaggccg cggttgaagg ctctctcaaa cggctaaaaa cggattacat tgatttatat  360
tacattcata gaattgaccc ctctatccca attgaagagg ttgccggcac cattcagaat  420
ttaaaacaag aagggaaaat tctacactgg ggactctccg aagccagcgc aaagacaata  480
cgccgtgctc ataaagtaga gccactagct gcggttgaaa gtgagtattc tatctggtgg  540
cgagaagctg aaaaagaagt attcccggtt ttagaagaac ttggcatcgg cttgtcgca   600
tacagcccac taggtcgtgg ttatttaact ggaaaattag atataaatgc tgacttcaat  660
gcaaacgaca accgtggtgg cttaccaaga ttccaaaaag aagccatgga agccaaccaa  720
gtactactag atttcatgaa agaaatcgcc gacgagcaaa acgtcacaac agcccaactt  780
gccctcgctt ggatacttga ccaaaaacct tggatcgtgc caattcccgg aacaacaaga  840
ccaagcagaa tagaagaaaa tatcgcctcc actgaaattc attttgatga tggagcacga  900
caaaaaatag ctgatgcttt atcgcagatt gaaattgttg gtgatagata ctcagccgcc  960
gaaaataaac gtatcggaaa ataa                                         984

SEQ ID NO: 4              moltype = DNA   length = 984
FEATURE                   Location/Qualifiers
source                    1..984
                          mol_type = genomic DNA
                          organism = Listeria monocytogenes
```

```
SEQUENCE: 4
atgaaaaaga gacaattagg aaatgctggc ttagttactt cagagcttgg attcggctgt    60
atggggctaa attatcatcg tggacctgcg aaagatcgaa atgaaatgat tgaagtcgta   120
cgcactgcaa tggatgcagg gattacgatg ttcgatacag ctgaagtgta tggacccttat  180
actaacgaag aacttgtcgg agaagctttg gttggcaaaa gaaaccatgt tcaaatcgca   240
acaaaaggtg gttttaaaat taatggttta aataacgaag tcgatagccg tccagaaagc   300
atcaaggccg cggttgaagg ctctctcaaa cggctaaaaa cagattacat tgatttatat   360
tacattcata gaattgaccc ctctatccca attgaagagg ttgccggcac cattcagaat   420
ttaaaacaag aagggaaaat tctacactgg ggactctccg aagccagcgc aaagacaata   480
cgccgtgctc ataaagtaga gccactagct gcggttgaag gtgagtattc tatctggtgg   540
cgagaagcag aaaaagaagt attcccggtt ttagaagaac ttggcatcgg gcttgtcgca   600
tacagcccac taggtcgtgg ttatttaact ggaaaattag atataaatgc tgacttcaat   660
gcaaacgaca accgtggtgg cttaccaaga ttccaaaaag aagccatgga agccaaccaa   720
gtactactag atttcatgaa agaaatcgcc gacgagcaaa acgtcacaac agcccaactt   780
gccctcgctt ggatacttga ccaaaaacct tggatcgtgc caattcccgg aacaacaaga   840
ccaagcagaa tagaagaaaa tatcgcctcc actgaaattc attttgatga tggagcacga   900
caaaaaatag ctgatgcttt atcgcagatt gaaattgttg gtgatagata ctcagccgcc   960
gaaaataaac gtatcggaaa ataa                                          984

SEQ ID NO: 5                moltype = DNA   length = 983
FEATURE                     Location/Qualifiers
source                      1..983
                            mol_type = genomic DNA
                            organism = Listeria monocytogenes
SEQUENCE: 5
atgaaaaaga gacaattagg aaacactggt ttagtaactt cagagcttgg attcggctgt    60
atgggactca attatcaccg gggacctgcg aaagatagaa aagaaatgat tgaagtcgta   120
cgcactgcaa tggatacagg gattacgatg ttcgatactg ctgaagtgta cggaccttat   180
actaatgaag aacttgtcgg agaagcttta gttggcaaaa gaaaccatgt tcaaattgca   240
acaaaaggtg gttttaaaat taatggttta aataacgaag tcgatagccg tccagaaagc   300
atcaaggccg cggttgaagg ctctctcaaa cggctaaaaa cggattacat tgatttatat   360
tacattcata gaattgaccc ctctatccca attgaagagg ttgccggaac cattcagaat   420
ttaaaacaag aaggaaaaat tctacactgg ggactttccg aagccagcgc aaagacaata   480
cgccgtgctc ataaagtaga gccactagct gctgttgaaa atgagtattc catctggtgg   540
cgagaagctg aaaaagaaat atttccggtt ttagaagaac ttggcatcgg gcttgtcgca   600
tacagcccac taggtcgcgg ttatttaact ggcaaattgg atataaatgc tagcttcaat   660
gaaaacgaca accgcggtgg cttaccaaga ttccaaaaag aagccatgga agccaaccaa   720
gtactactcg attttatgaa agaaatagcc gacgagcaaa atgtcacaac ggcacaactc   780
gccatcgctt ggatacttga ccaaaaacct tggatcgtgc caattcccgg aacaacaaga   840
caaagcagaa ttaagaaaaa tatcgcctcc acggacattc gttttgatga cggagcacga   900
caaaaaatag ctgatgcttt atcgcagatt gaaattgttg gtgatagata ctcagcagct   960
gaaaataaac gcatcggaaa gta                                          983

SEQ ID NO: 6                moltype = DNA   length = 984
FEATURE                     Location/Qualifiers
source                      1..984
                            mol_type = genomic DNA
                            organism = Listeria monocytogenes
SEQUENCE: 6
atgaaaaaga gacaattagg aaatgctggc ttagttactt cagagcttgg attcggctgt    60
atggggctaa attatcatcg tggacctgcg aaagatcgaa atgaaatgat tgaagtcgta   120
cgcactgcaa tggatgcagg gattacgatg ttcgatacag ctgaagtgta tggacccttat  180
actaacgaag aacttgtcgg agaagctttg gttggcaaaa gaaaccatgt tcaaatcgca   240
acaaaaggtg gttttaaaat taatggttta aataacgaag tcgatagccg tccagaaagc   300
atcaaggccg cggttgaagg ctctctcaaa cggctaaaaa cagattacat tgatttatat   360
tacattcata gaattgaccc ctctatccca attgaagagg ttgccggcac cattcagaat   420
ttaaaacaag aagggaaaat tctacactgg ggactctccg aagccagcgc aaagacaata   480
cgccgtgctc ataaagtaga gccactagct gcggttgaag gtgagtattc tatctggtgg   540
cgagaagctg aaaaagaagt attcccggtt ttagaagaac ttggcatcgg gcttgtcgca   600
tacagcccac taggtcgtgg ttatttaact ggaaaattag atataaatgc tgacttcaat   660
gcaaacgaca accgtggtgg cttaccaaga ttccaaaaag aagccatgga agccaaccaa   720
gtactactag atttcatgaa agaaatcgcc gacgagcaaa acgtcacaac agcccaactt   780
gccctcgctt ggatacttga ccaaaaacct tggatcgtgc caattcccgg aacaacaaga   840
ccaagcagaa tagaagaaaa tatcgcctcc actgaaattc attttgatga tggagcacga   900
caaaaaatag ctgatgcttt atcgcagatt gaaattgttg gtgatagata ctcagccgcc   960
gaaaataaac gtatcggaaa ataa                                          984

SEQ ID NO: 7                moltype = DNA   length = 983
FEATURE                     Location/Qualifiers
source                      1..983
                            mol_type = genomic DNA
                            organism = Listeria monocytogenes
SEQUENCE: 7
atggataaga gacgattagg cacgactggc ttagttacat cagaactcgg atttggttgt    60
atggggctca attatcatcg tggtccggcg aaaaatcgga atgaaatgat agaagtcgtt   120
cgcgccgcaa tggattctgg tattacaatg ttcgataccg ccgaggttta tggtccttat   180
acaaatgaag aacttgtagg agaagctttg tctagcaaaa gaaatcatgt tcaaattgca   240
acgaaaggtg gctttaaaat cgatggttta aataacgagg ttgatagccg cccagaaagt   300
ctcaaagcag cagtggaagg atcgctaaaa cgcttaaaaa ctgattacat tgatctgtat   360
```

```
tacattcata gaattgaccc ttctatccca attgaagaag ttgccggaac tatcaagcag   420
ttaaagcaag aaggaaaaat tctacactgg gggctttccg aggcaagcgc caaaaccatc   480
cgacgagctc acaaagtaga acgtctagca acagtggaaa gtgaatactc catctggtgg   540
cgagaagccg aacaggaaat atttccggct ttagaagaac tcggcatcgg ccttgtcgca   600
tatagtcctc tcggtcgagg ctatttatct ggtaagcttg atatcaatac taattttact   660
gaaaatgaca accgcggcgg cctaccaaga ttccaaaaag aagccatgaa agccaaccaa   720
gtgctgctcg attttatgaa agaaatagcc gacgagcaaa atgtcacaac agctcagctt   780
gccatcgcct ggattctcga ccaaaaacca tggatcgtcc caattcccgg aacaacaaga   840
caaagtagaa taaagaaaaa tatcgccgcc actaaaattc attttgatga tgcagcacga   900
caaaaaatag ctactgcttt atctcagatt gaaatagttg gtgacaggta ctcagctgcc   960
gaaaataaac gcatcggaaa ata                                         983

SEQ ID NO: 8              moltype = DNA   length = 983
FEATURE                   Location/Qualifiers
source                    1..983
                          mol_type = genomic DNA
                          organism = Listeria monocytogenes
SEQUENCE: 8
atgaaaaaga gacaattagg aaacactggt ttagtaactt cagagcttgg attcggctgt    60
atgggactca attatcaccg gggacctgcg aaagatagaa aagaaatgat tgaagtcgta   120
cgcactgcaa tggatgcagg gattacgatg ttcgatactg ctgaagtgta cggaccttat   180
actaatgaag aacttgtcgg agaagcttta gttggcaaaa gaaaccatgt tcaaattgca   240
acaaaaggtg gtttttaaaat taatggttta aataacgaag tcgatagccg tccagaaagc   300
atcaaggccg cggttgaagg ctctctcaaa cggctaaaaa cggattacat tgatttatat   360
tacattcata gaattgaccc ctctatccca attgaagagg ttgccggaac cattcagaat   420
ttaaaacaag aaggaaaaat tctacactgg ggactttccg aaccagcg aaagacaata   480
cgccgtgctc ataaagtaga gccactagct gctgttgaaa atgagtattc catctggtgg   540
cgagaagctg aaaagaaat atttccggtt ttagaagaac ttggcatcgg gcttgtcgca   600
tacagcccac taggtcgcgg ttatttaact ggcaaattgg atataaatgc tagcttcaat   660
gaaaacgaca accgcggtgg cttaccaaga ttccaaaaag aagccatgga agccaaccaa   720
gtactactcg attttatgaa agaaatagcc gacgagcaaa atgtcacaac ggcacaactc   780
gccatcgctt ggtacttga ccaaaaacct tggatcgtgc caattcccgg aacaacaaaa   840
caaagcagaa ttaagaaaaa tatcgcctcc acggacattc gttttgatga cggagcacga   900
caaaaaatag ctgatgcttt atcgcagatt gaaattgttg gtgatagata ctcagcagct   960
gaaaataaac gcatcggaaa gta                                         983

SEQ ID NO: 9              moltype = DNA   length = 983
FEATURE                   Location/Qualifiers
source                    1..983
                          mol_type = genomic DNA
                          organism = Listeria monocytogenes
SEQUENCE: 9
atggataaga gacgattggg caagactggc ttagttacat cagaactcgg atttggttgt    60
atggggctca attatcatcg tggtccggcg aaaaatcgaa atgaaatgat agaagtcgtt   120
cgcgccgcaa tagattctgg tattacaatg ttcgataccg ccgaggttta cggtccttat   180
acgaatgaag aacttgtagg agaagctttg tctggcaaaa gaaatcatgt tcaaatcgca   240
acgaaaggtg gctttaaaat cgatggttta aataacgagg ttgatagccg cccagaaagt   300
ctcaaagcag cagtggaagg atcgctaaaa cgcttgaaaa ctgattacat tgatttgtat   360
tacattcata gaattgaccc ttctatccca attgaagaag ttgccggaac tatcaagcag   420
ttaaagcaag aaggaaaaat tctacactgg gggctttccg aggcaagcgc caaaaccatc   480
cgacgagctc acaaagtaga acctctagca acagtggaaa gtgaatactc catctggtgg   540
cgagaagccg aacaggaaat atttccggtt ttagaagaac tcggcatcgg ccttgtcgca   600
tatagtcctc tcggtcgagg ctatttatct ggcaaacttg atatcaatac taatttcact   660
gaaaatgaca accgtggcgg gctaccaaga ttccaaaaag aagccatgaa agccaaccaa   720
gtgctgctcg attttatgaa agaaatagct gacgagcaaa atgtcacaac agcccagctt   780
gccatcgcct ggattctcga ccaaaaacca tggatcgtcc caattcccgg aacaacaaga   840
caaagtagaa taaagaaaaa tatcgccgcc actaaaattc attttgatga tgcagcacga   900
caaaaaatag ctactgcttt atctcagatt gaaatagttg gtgacaggta ctcagctgcc   960
gaaaataaac gcatcggaaa ata                                         983

SEQ ID NO: 10             moltype = DNA   length = 983
FEATURE                   Location/Qualifiers
source                    1..983
                          mol_type = genomic DNA
                          organism = Listeria monocytogenes
SEQUENCE: 10
atgaaaaaga gacaattagg aaacactggt ttagtaactt cagagcttgg attcggctgt    60
atgggactca attatcaccg gggacctgcg aaagatagaa aagaaatgat tgaagtcgta   120
cgcactgcaa tggatgcagg gattacgatg ttcgatactg ctgaagtgta cggaccttat   180
actaatgaag aacttgtcgg agaagcttta gttggcaaaa gaaaccatgt tcaaattgca   240
acaaaaggtg gtttttaaaat taatggttta aataacgaag tcgatagccg tccagaaagc   300
atcaaggccg cggttgaagg ctctctcaaa cggctaaaaa cggattacat tgatttatat   360
tacattcata gaattgaccc ctctatccca attgaagagg ttgccggaac cattcagaat   420
ttaaaacaag aaggaaaaat tctacactgg ggactttccg aaccagcg aaagacaata   480
cgccgtgctc ataaagtaga gccactagct gctgttgaaa gtgagtattc catctggtgg   540
cgagaagctg aaaagaaat atttccggtt ttagaagaac ttggcatcgg gcttgtcgca   600
tacagcccac taggtcgcgg ttatttaact ggcaaattgg atataaatgc tagcttcaat   660
gaaaacgaca accgcggtgg cttaccaaga ttccaaaaag aagccatgga agccaaccaa   720
gtactactcg attttatgaa agaaatagcc gacgagcaaa atgtcacaac ggcacaactc   780
```

```
gccatcgctt ggatacttga ccaaaaacct tggatcgtgc caattccgg  aacaacaaaa    840
caaagcagaa ttaaagaaaa tatcgcctcc acggacattc gttttgatga cggagcacga    900
caaaaaatag ctgatgcttt atcgcagatt gaaattgttg gtgatagata ctcagcagct    960
gaaaataaac gcatcggaaa gta                                            983

SEQ ID NO: 11              moltype = DNA  length = 983
FEATURE                    Location/Qualifiers
source                     1..983
                           mol_type = genomic DNA
                           organism = Listeria monocytogenes
SEQUENCE: 11
atgaaaaaga gacaattagg aaacactggt ttagtaactt cagagcttgg attcggctgt     60
atgggactca attatcaccg gggacctgcg aaagatagaa aagaaatgat tgaagtcgta    120
cgcactgcaa tggatgcagg gattacgatg ttcgatactg ctgaagtgta cggaccttat    180
actaatgaag aacttgtcgg agaagcttta gttggcaaaa gaaaccatgt tcaaattgca    240
acaaaaggtg gttttaaaat taatggttta aataacgaag tcgatagccg tccagaaagc    300
atcaaggccg cggttgaagg ctctctcaaa cggctaaaaa cggattacat tgatttatat    360
tacattcata gaattgaccc ctctatccca attgaagagg ttgccggaac cattcagaat    420
ttaaaacaag aaggaaaaat tctacactgg ggactttccg aagccagcgc aaagacaata    480
cgccgtgctc ataaagtaga gccactagct gctgttgaaa atgagtattc catctggtgg    540
cgagaagctg aaaaagaaat atttccggtt ttagaagaac ttggcatcgg gcttgtcgca    600
tacagcccac taggtcgcgg ttatttaact ggcaaattgg atataaatgc tagcttcaat    660
gaaaacgaca accgcggtgg cttaccaaga ttccaaaaag aagccatgga agccaaccaa    720
gtactactcg attttatgaa agaaatagcc gacgagcaaa atgtcacaac ggcacaactc    780
gccatcgctt ggatacttga ccaaaaacct tggatcgtgc caattccgg  aacaacaaaa    840
caaagcagaa ttaaagaaaa tatcgcctcc acggacattc gttttgatga cggagcacga    900
caaaaaatag ctgatgcttt atcgcagatt gaaattgttg gtgatagata ctcagcagct    960
gaaaataaac gcatcggaaa gta                                            983

SEQ ID NO: 12              moltype = DNA  length = 983
FEATURE                    Location/Qualifiers
source                     1..983
                           mol_type = genomic DNA
                           organism = Listeria monocytogenes
SEQUENCE: 12
atgaaaaaga gacaattagg aaacactggt ttagtaactt cagagcttgg attcggctgt     60
atgggactca attatcaccg gggacctgcg aaagatagaa agaaaatgat tgaagtcgta    120
cgcactgcaa tggatgcagg gattacgatg ttcgatactg ctgaagtgta cggaccttat    180
actaatgaag aacttgtcgg agaagcttta gttggcaaaa gaaaccatgt tcaaattgca    240
acaaaaggtg gttttaaaat taatggttta aataacgaag tcgatagccg tccagaaagc    300
atcaaggccg cggttgaagg ctctctcaaa cggctaaaaa cggattacat tgatttatat    360
tacattcata gaattgaccc ctctatccca attgaagagg ttgccggaac cattcagaat    420
ttaaaacaag aaggaaaaat tctacactgg ggactttccg aagccagcgc aaagacaata    480
cgccgtgctc ataaagtaga gccactagct gctgttgaaa atgagtattc catctggtgg    540
cgagaagctg aaaaagaaat atttccggtt ttagaagaac ttggcatcgg gcttgtcgca    600
tacagcccac taggtcgcgg ttatttaact ggcaaattgg atataaatgc tagcttcaat    660
gaaaacgaca accgcggtgg cttaccaaga ttccaaaaag aagccatgga agccaaccaa    720
gtactactcg attttatgaa agaaatagcc gacgagcaaa atgtcacaac ggcacaactc    780
gccatcgctt ggatacttga ccaaaaacct tggatcgtgc caattccgg  aacaacaaaa    840
caaagcagaa ttaaagaaaa tatcgcctcc acggacattc gttttgatga cggagcacga    900
caaaaaatag ctgatgcttt atcgcagatt gaaattgttg gtgatagata ctcagcagct    960
gaaaataaac gcatcggaaa gta                                            983

SEQ ID NO: 13              moltype = DNA  length = 1134
FEATURE                    Location/Qualifiers
source                     1..1134
                           mol_type = genomic DNA
                           organism = Listeria monocytogenes
SEQUENCE: 13
atgaaaatcg tcatcgcacc tgattcattc aaagagagcg ccactgcggt ggaagtagca     60
actgccataa aaaaaggctg gactaaagct cgtccagccg atcaaattag ccttgccct    120
gtttctgacg ggggtgaggg ttttcttact gttttaagtg agtcttccga ggtggaattg    180
ttccaagcag aagtaaccaa cctaaacggt cacaaaataa cggcccccta cggtattcac    240
actagccaag aaactgcgat tatcgagtcc gccaacacga ttggattaga tttaatccca    300
gcggcagacc gcaatccagc ttacgcgagc tctaaaggag tcggtgaact aattttggcg    360
gcactgaatc acaacgtcaa aaaaatcatt atcgggctag cgcaagtgg tacaaacgat    420
ggcggcgctg ggctaatcca agctttggc gttgcactac ttgataaaaa caacagcct    480
attccgcccg gcggtattca tttgcaagag ctagcctata ttgatgccaa caatcttaac    540
ccaaagctga acaacattca attccaaata gcctgtgacg tgacgaatcc acttcttgga    600
gaaaacggtg ctacatttgt tttcggtgct caaaaagggg caagtcccga catgctcgtt    660
aaactagaga acgccatgca gaactacgga gcaaaactcg accaattttc ttctcaaaaa    720
atcaccacca aaaaggagc tggagccgct ggtggtatcg ctgctggact aatgaccttc    780
ctaaatgcag acttattaag cggttcaact cttgttatgg aactttctaa tatgaaagat    840
aaaatgaaag accgatat tgttattgtt ggtgaaggac gaatgggacaa gcaatcgatg    900
atggggaaaa ttcctgttca aatcgctcaa gaagctaaaa acaaggttg cttcgttctg    960
gctattgtcg gcagccttgc actcgaaaac aacctagccc aacagcacgg catcgatgct   1020
ttttccccaa acatccctga aataacagat ttacccactc ttttttgaaaa tacgacgaaa   1080
aacctcgaac gtacggcgga aaacatcgcc aaactaactt taattggcaa ataa          1134
```

```
SEQ ID NO: 14              moltype = DNA   length = 1134
FEATURE                    Location/Qualifiers
source                     1..1134
                           mol_type = genomic DNA
                           organism = Listeria monocytogenes
SEQUENCE: 14
atgaaaatcg tcatcgcacc tgattcattc aaagagagcg ccactgctgt tgaagtagca   60
aatgctataa aaaaaggctg gactaaagca cgtccagccg atcaaattag ccttgccect  120
gtttctgacg ggggtgaggg ttttcttact gttttaagtg agtcttccga ggtggaattg  180
tttcaagcag aagtaaccaa cctaaatggt cacaaaataa cggcctccta cggtattctc  240
gctagccaag aaactgcaat tatcgagtcc gctaacacga ttggattaga tttaatccca  300
gccgtagacc gcaatccagc ttacgcgagc tctaaaggcg tcggtgaact tattttggcg  360
gcactgaatc acaacgtcaa aaaaatcatt atcggccttg gtggaagtgg cacaaacgat  420
ggcggcgctg ggctaatcca agctttgggc gttgcactac ttgataaaaa caaacagcct  480
attccgcccg gtgcattcca tttgcaagaa ctagcttaca ttgatgccag caaccttaat  540
ccaaagctga aaaacattca attccaaata gcctgcgacg tcacgaatcc acttcttgga  600
gaaaacggcg ctaccttcgt tttcggtgct caaaaaggcg caactcccga aatgctcgtt  660
caactagagc gcgccatgca gaactacgga gcaaaactcg atcaatttc atctcaaaaa  720
atcactacaa aaaaaggagc cggagccgct ggtggtatcg ctgccggact aatgactttc  780
ctaaatgcat acgtgttaag cggttcagct ctagttatgg aactttctaa tatgaaggat  840
aaaatgaaag atgcggatat cgttattgtt ggtgaaggac gaatggacaa gcaatcgatg  900
atggggaaaa tccctgttca aattgctcaa gaagctaaaa aacaaggttg tttcgtccta  960
gcaatcgtcg gtagccttgc actcgaaaac aatatcgccc aacaacacgg tatcgatgcg 1020
tttttcccaa acatcccaga aataacagat ttacccactc ttttcgaaaa tacaacaaag 1080
aacctcgaac gcacggcgga aaacattgcc aaactaactt taattggcaa ataa        1134

SEQ ID NO: 15              moltype = DNA   length = 1134
FEATURE                    Location/Qualifiers
source                     1..1134
                           mol_type = genomic DNA
                           organism = Listeria monocytogenes
SEQUENCE: 15
atgaaaatcg tcatcgcacc tgattcattc aaagaaagcg ccactgcggt ggaagtagca   60
actgccatta aaaaaggctg gactaaagct cgtccagccg atcaaataag ccttgccect  120
gtttctgacg ggggtgaggg ttttcttact gttttaagtg agtcttccga ggtggaattg  180
ttccaagcag aagtaaccaa cttaaacggt cacaaaataa tggcctccta cggtattcac  240
gcccgccaag aaactgcgat tatcgagtcc gccaacacga ttggattaga tttaatccca  300
gcggcagacc gtaatccagc ccatgcaagc tctgctggcg tcggtgaact aattttggca  360
tcactggatc acaacgtcaa aaaaatcatt atcggccttg gtggaagtgg cacaaacgat  420
ggcggcgctg gactaatcca agctttgggc gttgcactac ttgataaaaa caaacagcct  480
attccgcccg gtgcattcca tttgcaagaa ctagcctaca ttgatgccag caaccttaac  540
ccaaagctga aaaacattca attccaaata gcctgtgacg tgacgaatcc acttcttgga  600
gaaaacggtg ctacatttgt tttcggtgct caaaaaggcg caagtcccga catgctcgtt  660
aaactagaga acgccatgca gaactacgga gcaaaactcg accaattttc ttctcaaaaa  720
atcaccacaa aaaaaggagc tggagccgct ggtggtatcg ctgctggact aatgaccttc  780
ctaaatgcag acttattaag cggttcaact cttgttatgg aactttctaa tatgaaagat  840
aaaatgaaag acgccgatat tgttattgtt ggtgaaggac gaatggacaa gcaatcgatg  900
atggggaaaa tccctgttca aatcgctcaa gaagctaaaa aacaaggttg cttcgttctg  960
gctattgtcg gcagccttgc actcgaaaac aacctagccc agcagcacgg catcgatgct 1020
tttttcccaa acatccctga aataacagat ttacccactc tttttgaaaa tacgacgaaa 1080
aacctcgaac gtacggcgga aaacatcgcc aaactaactt taattggcaa ataa        1134

SEQ ID NO: 16              moltype = DNA   length = 1134
FEATURE                    Location/Qualifiers
source                     1..1134
                           mol_type = genomic DNA
                           organism = Listeria monocytogenes
SEQUENCE: 16
atgaaaatcg tcatcgcacc tgattcattc aaagaaagcg ccactgcggt ggaagtagca   60
actgccatta aaaaaggctg gactaaagct cgtccagccg atcaaataag ccttgccect  120
gtttctgacg ggggtgaggg ttttcttact gttttaagtg agtcttccga ggtggaattg  180
ttccaagcag aagtaaccaa cttaaacggt cacaaaataa tggcctccta cggtattcac  240
gcccgccaag aaactgcgat tatcgagtcc gccaacacga ttggattaga tttaatccca  300
gcggcagacc gcaatccagc ttacgcgagc tctaaaggag tcggtgaact aattttggca  360
tcactggatc acaacgtcaa aaaaatcatt atcggccttg gtggaagtgg cacaaacgat  420
ggcggcgctg gactaatcca agctttgggc gttgcgctac ttgataaaaa caaacagcct  480
attctgcccg gcgtattcca tttgcaagag ctagcctata ttgatgccag caatcttaac  540
ccaaagctga aaaacattca attccaaata gcctgtgacg tgacgaatcc acttcttgga  600
gaaaacggtg ctacatttgt tttcggtgct caaaaaggca caagtcccga catgctcgtt  660
aaactagaga acgccatgca gaactacgga gcaaaactcg accaattttc ttctcaaaaa  720
atcaccacaa aaaaaggagc tggagccgct ggtggtatcg ctgctggact aatgaccttc  780
ctaaatgcag acttattaag cggttcaact cttgttatgg aactttctaa tatgaaagat  840
aaaatgaaag acgccgatat tgttattgtt ggtgaaggac gaatggacaa gcaatcgatg  900
atggggaaaa tccctgttca aatcgctcaa gaagctaaaa aacaaggttg cttcgttctg  960
gctattgtcg gcagccttgc actcgaaaac aacctagccc agcagcacgg catcgatgct 1020
tttttcccaa acatccctga aataacagat ttacccactc tttttgaaaa tacgacgaaa 1080
aacctcgaac gtacggcgga aaacatcgcc aaactaactt taattggcaa ataa        1134

SEQ ID NO: 17              moltype = DNA   length = 1134
```

| FEATURE | Location/Qualifiers |
|---|---|
| source | 1..1134 |
| | mol_type = genomic DNA |
| | organism = Listeria monocytogenes |

SEQUENCE: 17

```
atgaaaatcg tcatcgcacc tgattcattc aaagagagcg ccactgctgt tgaagtagca  60
aatgctataa aaaaaggctg gactaaagca cgtccagccg atcaaattag ccttgccccct 120
gtttctgacg ggggtgaggg ttttcttact gttttaagtg agtcttccga ggtggaatta  180
tttcaagcag aagtaaccaa cctaaatggt cacaaaataa cggcctccta cggtattctc  240
gctagccaag aaactgcgat tatcgagtcc gccaacacga ttggattaga tttaatccca  300
gccgtagacc gtaatccagc ttacgcgagc tctaaaggcg tcggtgaact aattttggcg  360
gcactgaatc acaacgtcaa aaaaatcatt atcggccttg gtggaagtgg cacaaacgat  420
ggcggcgctg ggctaatcca agctttgggc gttgcactac ttgataaaaa caaacagcct  480
attccgcccg gtggcattca tttgcaagaa ctagcctaca ttgatgccag caaccttaat  540
ccaaagctga aaacattca attccaaata gcctgcgacg tcacgaatcc acttcttgga   600
gaaaacggcg ctaccttcgt tttcggtgct caaaaaggcg caactcccga aatgctcgtt  660
caactagagc gcgccatgca gaactacgga gcaaaactcg atcaattttc atctcaaaaa  720
atcactacaa aaaaaggagc cggagccgct ggtggtatcg ctgccggact aatgactttc  780
ctaaatgcag acgtgttaag cggttcagct ctagttatgg aactttctaa tatgaaggat  840
aaaatgaaag atgcggatat cgttattgtt ggtgaaggac gaatggacaa gcaatcgatg  900
atggggaaaa tccctgttca aattgctcaa gaagctaaaa acaaggttg tttcgtccta   960
gcaatcgtcg gtagccttgc actcgaaaac aatatcgcct aacaacacgg tatcgatgcg 1020
tttttcccaa acatcccaga aataacagat ttacccactc ttttcgaaaa tacaacaaag 1080
aacctcgaac gcacggcgga aaacattgcc aaactaactt taattggcaa ataa         1134
```

| SEQ ID NO: 18 | moltype = DNA length = 1134 |
|---|---|
| FEATURE | Location/Qualifiers |
| source | 1..1134 |
| | mol_type = genomic DNA |
| | organism = Listeria monocytogenes |

SEQUENCE: 18

```
atgaaaatcg tcatcgcacc tgattcattc aaagaaagcg ccactgcggt ggaagtagca  60
actgccatta aaaaaggctg gactaaagct cgtccagccg atcaaataag ccttgccccct 120
gtttctgacg ggggtgaggg ttttcttact gttttaagtg agtcttccga ggtggaattg  180
ttccaagcag aagtaaccaa cttaaacggt cacaaaataa tggcctccta cggtattcac  240
gcccgccaag aaactgcgat tatcgagtcc gccaacacga ttggattaga tttaatccca  300
gcggcagacc gtaatccagc ccatgcaagc tctgctggcg tcggtgaact aattttggca  360
tcactggatc acaacgtcaa aaaaatcatt atcggccttg gtggaagtgg cacaaacgat  420
ggcggcgctg gactaatcca agctttgggc gttgcactac ttgataaaaa caaacagcct  480
attccgcccg gtggcattca tttgcaagaa ctagcctaca ttgatgccag caaccttaac  540
ccaaagctga aaacattca attccaaata gcctgtgacg tgacgaatcc acttcttgga   600
gaaaacggtg ctacatttgt tttcggtgct caaaaagggg caagtcccga catgctcgtt  660
aaactagaga acgccatgca gaactacgga gcaaaactcg accaattttc ttctcaaaaa  720
atcaccacaa aaaaaggagc tggagccgct ggtggtatcg ctgctggact aatgaccttc  780
ctaaatgcag acttattaag cggttcaact cttgttatgg aactttctaa tatgaaagat  840
aaaatgaaag acgccgatat tgttattgtt ggtgaaggac gaatggacaa gcaatcgatg  900
atggggaaaa ttcctgttca aatcgctcaa gaagctaaaa acaaggttgc cttcgttctg  960
gctattgtcg gcagccttgc actcgaaaac aacctagccc agcagcacgg catcgatgct 1020
tttttcccaa acatccctga aataacagat ttacccactc ttttgaaaaa tacgacgaaa 1080
aacctcgaac gtacggcgga aaacattgcc aaactaactt taattggcaa ataa         1134
```

| SEQ ID NO: 19 | moltype = DNA length = 1134 |
|---|---|
| FEATURE | Location/Qualifiers |
| source | 1..1134 |
| | mol_type = genomic DNA |
| | organism = Listeria monocytogenes |

SEQUENCE: 19

```
atgaaaatcg tcatcgcacc tgattcattc aaagagagcg ccactgcggt ggaagtagca  60
actgccataa aaaaaggctg gactaaagct cgtccagccg atcaaattag ccttgccccct 120
gtttctgacg ggggtgaggg ttttcttact gttttaagtg agtcttccga ggtggaattg  180
ttccaagcag aagtaaccaa cctaaacggt cacaaaataa cggcctccta cggtattcac  240
actagccaag aaactgcgat tatcgagtcc gccaacacga ttggattaga tttaatccca  300
gcggcagacc gcaatccagc ttacgcgagc tctaaaggcg tcggtgaact aattttggcg  360
gcactgaatc acaacgtcaa aaaaatcatt atcgggctag gcggaagtgg cacaaacgat  420
ggcggcgctg ggctaatcca agctttgggc gttgcactac ttgataaaaa caaacagcct  480
attccgcccg gtggcattca tttgcaagaa ctagcctaca ttgatgccag caaccttaat  540
ccaaagctga aaacattca attccaaata gcctgtgacg tcacgaatcc acttcttgga   600
gaaaacggcg ctaccttcgt tttcggtgct caaaaaggcg caactcccga aatgctcgtt  660
caactagagc acgccatgca gaactacggg gcaaaacttg atcaattttc atctcaaaaa  720
atcactacaa aaaaaggagc cggagccgct ggtggtatcg ctgccggact aatgactttc  780
ctaaatgcag acgtattaag cggttcagct cttgttatgg aactttctaa tatgaaggat  840
aaaatgaaag atgcggatat cgtcattgtt ggcgaagggc gaatggacaa gcaatcgatg  900
atggggaaaa tccctgttca aatcgctcaa gaagctaaaa acaaggttg tttcgtccta   960
gcaatcgtcg gtagccttgc actcgaaaac aatatcgcct aacaacacgg tatcgatgcg 1020
ttcttcccaa acatcccaga aataacagat ttacccactc ttttcgaaaa tacaacaaag 1080
aacctcgaac gcacggcgga aaacattgcc aaattaactt taattggcaa ataa         1134
```

| SEQ ID NO: 20 | moltype = DNA length = 1134 |
|---|---|
| FEATURE | Location/Qualifiers |

| | | |
|---|---|---|
| source | 1..1134 | |
| | mol_type = genomic DNA | |
| | organism = Listeria monocytogenes | |

SEQUENCE: 20

```
atgaaaatcg tcatcgcacc tgattcattc aaagagagcg ccactgctgt tgaagtagca   60
aatgctataa aaaaaggctg gactaaagca cgtccagccg atcaaattag ccttgcccct  120
gtttctgacg ggggtgaggg ttttcttact gttttaagtg agtcttccga ggtggaattg  180
tttcaagcag aagtaaccaa cctaaatggt cacaaaataa cggcctccta cggtattctc  240
gctagccaag aaactgcaat tatcgagtcc gctaacacaa ttggattaga tttaatccca  300
gccgtagacc gcaatccagc ttacgcgagc tctaaaggcg tcggtgaact aattttggcg  360
gcactgaatc acaacgtcaa aaaaatcatt atcggccttg gtggaagtgg cacaaacgat  420
ggcggcgctg ggctaatcca agctttgggc gttgcactac ttgataaaaa caaacagcct  480
attccgcccg gtggcattca tttgcaagaa ctagcttaca ttgatgccag caaccttaat  540
ccaaagctga aaacattca attccaaata gcctgcgacg tcacgaatcc acttcttgga  600
gaaaacggcg ctaccttcgt tttcggtgct caaaaaggcg caactcccga aatgctcgtt  660
caactagagc gcgccatgca gaactacgga gcaaaactcg atcaattttc atctcaaaaa  720
atcactacaa aaaaaggagc cggagccgct ggtggtatcg ctgccggact aatgactttc  780
ctaaatgcag acgtgttaag cggttcagct ctagttatgg aacttctcaa tatgaaggat  840
aaaatgaaag atgcggatat cgttattgtt ggtgaaggac gaatggacaa gcaatcgatg  900
atggggaaaa tccctgttca aattgctcaa gaagctaaaa acaaggttg ttcgtccta  960
gcaatcgtcg gtagccttgc actcgaaaac aatatcgccc aacaacacgg tatcgatgcg 1020
ttttttcccaa acatcccaga aataacagat ttacccactc ttttcgaaaa tacaacaaag 1080
aacctcgaac gcacggcgga aaacattgcc aaactaactt taattggcaa ataa        1134
```

| | | |
|---|---|---|
| SEQ ID NO: 21 | moltype = DNA length = 1134 | |
| FEATURE | Location/Qualifiers | |
| source | 1..1134 | |
| | mol_type = genomic DNA | |
| | organism = Listeria monocytogenes | |

SEQUENCE: 21

```
atgaaaatcg tcatcgcacc tgattcattc aaagagagcg ccactgctgt tgaagtagca   60
aatgccataa aaaaaggctg gactaaagca cgtccagccg atcaaattag ccttgcccct  120
gtttctgacg ggggtgaggg ttttcttact gttttaagtg agtcttccga ggtggaattg  180
tttcaagcag aagtaaccaa cctaaatggt cacaaaataa cggcctccta cggtattctc  240
gctagccaag aaactgcaat tatcgagtcc gctaacacga ttggattaga tttaatccca  300
gccgtagacc gcaatccagc ttacgcgagc tctaaaggcg tcggtgaact tattttggcg  360
gcactgaatc acaacgtcaa aaaaatcatt atcggccttg gtggaagtgg cacaaacgat  420
ggcggcgctg ggctaatcca agctttgggc gttgcactac ttgataaaaa caaacagcct  480
attccgcccg gtggcattca tttgcaagaa ctagcttaca ttgatgccag caaccttaat  540
ccaaagctga aaacattca attccaaata gcctgcgacg tcacgaatcc acttcttgga  600
gaaaacggcg ctaccttcgt tttcggtgct caaaaaggcg caactcccga aatgctcgtt  660
caactagagc gcgccatgca gaactacgga gcaaaactcg atcaattttc atctcaaaaa  720
atcactacaa aaaaaggagc cggagccgct ggtggtatcg ctgccggact aatgactttc  780
ctaaatgcag acgtgttaag cggttcagct ctagttatgg aacttctcaa tatgaaggat  840
aaaatgaaag atgcggatat cgttattgtt ggtgaaggac gaatggacaa gcaatcgatg  900
atggggaaaa tccctgttca aattgctcaa gaagctaaaa acaaggttg ttcgtccta  960
gcaatcgtcg gtagccttgc actcgaaaac aatatcgccc aacaacacgg tatcgatgcg 1020
ttttttcccaa acatcccaga aataacagat ttacccactc ttttcgaaaa tacaacaaag 1080
aacctcgaac gcacggcgga aaacattgcc aaactaactt taattggcaa ataa        1134
```

| | | |
|---|---|---|
| SEQ ID NO: 22 | moltype = DNA length = 1134 | |
| FEATURE | Location/Qualifiers | |
| source | 1..1134 | |
| | mol_type = genomic DNA | |
| | organism = Listeria monocytogenes | |

SEQUENCE: 22

```
atgaaaatcg tcatcgcacc tgattcattc aaagagagcg ccactgcagt ggaagtagca   60
actgccataa aaaaaggctg gactaaagct cgtccagccg atcaaattag ccttgcccct  120
gtttctgacg ggggtgaggg ttttcttact gttttaagtg agtcttccga ggtggaattg  180
ttccaagcag aagtaaccaa cctaaacggt cacaaaataa cggcctccta cggtattcac  240
actagccaag aaactgcgat tatcgagtcc gccaacacga ttggattaga tttaatccca  300
gcagtagacc gcaatccagc ttacgcgagc tctaaaggcg tcggtgaact aattttggcg  360
gcactgaatc acaacgtcaa aaaaatcatt atcgggctag cggaagtgg tacaaacgat  420
ggcggcgctg ggctaatcca agctttgggc gttgcactac ttgataaaaa caaacagcct  480
attccgcccg gtggcattca tttgcaagaa ctagcctaca ttgatgccag caaccttaat  540
ccaaagctga aaacattca attccaaata gcctgcgacg tcacgaatcc acttcttgga  600
gaaaacggag ctaccttcgt tttcggtgct caaaaaggcg caactcccga aatgctcgtt  660
caactagagc atgccatgca gaactacggg gcaaaaatc gatcaattttc atctcaaaaa  720
atcactacaa aaaaaggagc cggagccgcc ggtggtatcg ctgccggact aatgactttc  780
ctaaatgcag acgtattaag cggttcagct cttgttatgg aacttctcaa tatgaaggat  840
aaaatgaaag atgcggatat cgtcattgtt ggcgaaggac gaatggacca gcaatcgatg  900
atggggaaaa ttcctgttca aatcgctcaa gaagctaaaa acaaggtttg ttcgtccta  960
gcaatcgtcg gtagccttgc actcgaaaac aatatcgccc aacaacacgg tatcgatgcg 1020
ttcttcccaa acatcccaga aataacagat ttacccactc ttttcgaaaa tacaacaaag 1080
aacctcgaac gcacggcgga aaacattgcc aaattaactt taattggcaa ataa        1134
```

| | | |
|---|---|---|
| SEQ ID NO: 23 | moltype = DNA length = 1134 | |
| FEATURE | Location/Qualifiers | |
| source | 1..1134 | |

```
                        mol_type = genomic DNA
                        organism = Listeria monocytogenes
SEQUENCE: 23
atgaaaatcg tcatcgcacc tgattcattc aaagagagcg ccactgctgt tgaagtagca    60
aatgctataa aaaaaggctg gactaaagca cgtccagccg atcaaattag ccttgcccct   120
gtttctgacg ggggtgaggg ttttcttact gttttaagtg agtcttccga ggtggaattg   180
tttcaagcag aagtaaccaa cctaaatggt cacaaaataa cggcctccta cggtattctc   240
gctagccaag aaactgcgat tatcgagtcc gccaacacga ttggattaga tttaatccca   300
gccgtagacc gtaatccagc ttacgcgagc tctaaaggcg tcggtgaact aattttggcg   360
gcactgaatc acaacgtcaa aaaaatcatt atcggccttg gtggaagtgg cacaaacgat   420
ggcggcgctg gctaatcca agctttgggc gttgcactac ttgataaaaa caaacagcct   480
attccgcccg gtggcattca tttgcaagaa ctagcttaca ttgatgccag caaccttaat   540
ccaaagctga aaacattca attccaaata gcctgcgacg tcacgaatcc acttcttgga   600
gaaaacggcg ctaccttcgt tttcggtgct caaaaaggcg caactcccga aatgctcgtt   660
caactagagc gcgccatgca gaactacgga gcaaaactcg atcaattttc atctcaaaaa   720
atcactacaa aaaaggagc cggagccgct ggtggtatcg ctgccggact aatgactttc   780
ctaaatgcag acgtgttaag cggttcagct ctagttatgg aactttctaa tatgaaggat   840
aaaatgaaag atgcggatat cgttattgtt ggtgaaggac gaatggacaa gcaatcgatg   900
atggggaaaa tccctgttca aattgctcaa gaagctaaaa acaaggttg tttcgtccta   960
gcaatcgtcg gtagccttgc actcgaaaac aatatcgccc aacaacacgg tatcgatgcg  1020
ttttttcccaa acatcccaga aataacagat ttacccactc ttttcgaaaa tacaacaaag  1080
aacctcgaac gcacggcgga aaacattgcc aaactaactt taattggcaa ataa         1134

SEQ ID NO: 24            moltype = DNA  length = 1134
FEATURE                  Location/Qualifiers
source                   1..1134
                         mol_type = genomic DNA
                         organism = Listeria monocytogenes
SEQUENCE: 24
atgaaaatcg tcatcgcacc tgattcattc aaagagagcg ccactgctgt tgaagtagca    60
aatgctataa aaaaaggctg gactaaagca cgtccagccg atcaaattag ccttgcccct   120
gtttctgacg ggggtgaggg ttttcttact gttttaagtg agtcttccga ggtggaattg   180
tttcaagcag aagtaaccaa cctaaatggt cacaaaataa cggcctccta cggtattctc   240
gctagccaag aaactgcaat tatcgagtcc gctaacacga ttggattaga tttaatccca   300
gccgtagacc gcaatccagc ttacgcgagc tctaaaggcg tcggtgaact aattttggcg   360
gcactgaatc acaacgtcaa aaaaatcatt atcggccttg gtggaagtgg cacaaacgat   420
ggcggcgctg gctaatcca agctttgggc gttgcactac ttgataaaaa caaacagcct   480
attccgcccg gtggcattca tttgcaagaa ctagcttaca ttgatgccag caaccttaat   540
ccaaagctga aaacattca attccaaata gcctgcgacg tcacgaatcc acttcttgga   600
gaaaacggcg ctaccttcgt tttcggtgct caaaaaggcg caactcccga aatgctcgtt   660
caactagagc gcgccatgca gaactacgga gcaaaactcg atcaattttc atctcaaaaa   720
atcactacaa aaaaggagc cggagccgct ggtggtatcg ctgccggact aatgactttc   780
ctaaatgcag acgtgttaag cggttcagct ctagttatgg aactttctaa tatgaaggat   840
aaaatgaaag atgcggatat cgttattgtt ggtgaaggac gaatggacaa gcaatcgatg   900
atggggaaaa tccctgttca aattgctcaa gaagctaaaa acaaggttg tttcgtccta   960
gcaatcgtcg gtagccttgc actcgaaaac aatatcgccc aacaacacgg tatcgatgcg  1020
ttttttcccaa acatcccaga aataacagat ttacccactc ttttcgaaaa tacaacaaag  1080
aacctcgaac gcacggcgga aaacattgcc aaactaactt taattggcaa ataa         1134

SEQ ID NO: 25            moltype = DNA  length = 1134
FEATURE                  Location/Qualifiers
source                   1..1134
                         mol_type = genomic DNA
                         organism = Listeria monocytogenes
SEQUENCE: 25
atgaaaatcg tcatcgcacc tgattcattc aaagagagcg ccactgctgt tgaagtagca    60
aatgctataa aaaaaggctg gactaaagca cgtccagccg atcaaattag ccttgcccct   120
gtttctgacg ggggtgaggg ttttcttact gttttaagtg agtcttccga ggtggaattg   180
tttcaagcag aagtaaccaa cctaaatggt cacaaaataa cggcctccta cggtattctc   240
gctagccaag aaactgcaat tatcgagtcc gctaacacga ttggattaga tttaatccca   300
gccgtagacc gcaatccagc ttacgcgagc tctaaaggcg tcggtgaact tattttggcg   360
gcactgaatc acaacgtcaa aaaaatcatt atcggccttg gtggaagtgg cacaaacgat   420
ggcggcgctg gctaatcca agctttgggc gttgcactac ttgataaaaa caaacagcct   480
attccgcccg gtggcattca tttgcaagaa ctagcttaca ttgatgccag caaccttaat   540
ccaaagctga aaacattca attccaaata gcctgcgacg tcacgaatcc acttcttgga   600
gaaaacggcg ctaccttcgt tttcggtgct caaaaaggcg caactcccga aatgctcgtt   660
caactagagc gcgccatgca gaactacgga gcaaaactcg atcaattttc atctcaaaaa   720
atcactacaa aaaaggagc cggagccgct ggtggtatcg ctgccggact aatgactttc   780
ctaaatgcat acgtgttaag cggttcagct ctagttatgg aactttctaa tatgaaggat   840
aaaatgaaag atgcggatat cgttattgtt ggtgaaggac gaatggacaa gcaatcgatg   900
atggggaaaa tccctgttca aattgctcaa gaagctaaaa acaaggttg tttcgtccta   960
gcaatcgtcg gtagccttgc actcgaaaac aatatcgccc aacaacacgg tatcgatgcg  1020
ttttttcccaa acatcccaga aataacagat ttacccactc ttttcgaaaa tacaacaaag  1080
aacctcgaac gcacggcgga aaacattgcc aaactaactt taattggcaa ataa         1134

SEQ ID NO: 26            moltype = DNA  length = 20
FEATURE                  Location/Qualifiers
misc_feature             1..20
                         note = primer LMO0084-F286A
```

```
source                    1..20
                          mol_type = other DNA
                          organism = synthetic construct
SEQUENCE: 26
agccgtccag aaagcatcaa                                              20

SEQ ID NO: 27             moltype = DNA   length = 20
FEATURE                   Location/Qualifiers
misc_feature              1..20
                          note = primer LMO0084-F286B
source                    1..20
                          mol_type = other DNA
                          organism = synthetic construct
SEQUENCE: 27
agccgcccag aaagtctcaa                                              20

SEQ ID NO: 28             moltype = DNA   length = 20
FEATURE                   Location/Qualifiers
misc_feature              1..20
                          note = primer LMO0084-F281A
source                    1..20
                          mol_type = other DNA
                          organism = synthetic construct
SEQUENCE: 28
tcgatagccg tccagaaagc                                              20

SEQ ID NO: 29             moltype = DNA   length = 20
FEATURE                   Location/Qualifiers
misc_feature              1..20
                          note = primer LMO0084-F281B
source                    1..20
                          mol_type = other DNA
                          organism = synthetic construct
SEQUENCE: 29
ttgatagccg cccagaaagt                                              20

SEQ ID NO: 30             moltype = DNA   length = 20
FEATURE                   Location/Qualifiers
misc_feature              1..20
                          note = primer LMO0084-R757A
source                    1..20
                          mol_type = other DNA
                          organism = synthetic construct
SEQUENCE: 30
gctcgtcggc gatttctttc                                              20

SEQ ID NO: 31             moltype = DNA   length = 20
FEATURE                   Location/Qualifiers
misc_feature              1..20
                          note = primer LMO0084-R757B
source                    1..20
                          mol_type = other DNA
                          organism = synthetic construct
SEQUENCE: 31
gctcgtcggc tatttctttc                                              20

SEQ ID NO: 32             moltype = DNA   length = 20
FEATURE                   Location/Qualifiers
misc_feature              1..20
                          note = primer LMO2736-F8
source                    1..20
                          mol_type = other DNA
                          organism = synthetic construct
SEQUENCE: 32
tcgtcatcgc acctgattca                                              20

SEQ ID NO: 33             moltype = DNA   length = 20
FEATURE                   Location/Qualifiers
misc_feature              1..20
                          note = primer LMO2736-F222
source                    1..20
                          mol_type = other DNA
                          organism = synthetic construct
SEQUENCE: 33
ggcctcctac ggtattcacg                                              20

SEQ ID NO: 34             moltype = DNA   length = 20
FEATURE                   Location/Qualifiers
misc_feature              1..20
```

```
                        note = primer LMO2736-F488
source                  1..20
                        mol_type = other DNA
                        organism = synthetic construct
SEQUENCE: 34
ccggtggcat tcatttgcaa                                                    20

SEQ ID NO: 35           moltype = DNA  length = 20
FEATURE                 Location/Qualifiers
misc_feature            1..20
                        note = primer LMO2736-F530
source                  1..20
                        mol_type = other DNA
                        organism = synthetic construct
SEQUENCE: 35
gcaaccttaa cccaaagctg                                                    20

SEQ ID NO: 36           moltype = DNA  length = 20
FEATURE                 Location/Qualifiers
misc_feature            1..20
                        note = primer LMO2736-F572
source                  1..20
                        mol_type = other DNA
                        organism = synthetic construct
SEQUENCE: 36
cctgtgacgt sacgaatcca                                                    20

SEQ ID NO: 37           moltype = DNA  length = 20
FEATURE                 Location/Qualifiers
misc_feature            1..20
                        note = primer LMO2736-R176
source                  1..20
                        mol_type = other DNA
                        organism = synthetic construct
SEQUENCE: 37
tccacctcgg aagactcact                                                    20

SEQ ID NO: 38           moltype = DNA  length = 20
FEATURE                 Location/Qualifiers
misc_feature            1..20
                        note = primer LMO2736-R591
source                  1..20
                        mol_type = other DNA
                        organism = synthetic construct
SEQUENCE: 38
tggattcgtc acgtcacagg                                                    20

SEQ ID NO: 39           moltype = DNA  length = 20
FEATURE                 Location/Qualifiers
misc_feature            1..20
                        note = primer LMO2736-R685
source                  1..20
                        mol_type = other DNA
                        organism = synthetic construct
SEQUENCE: 39
agttctgcat ggcgttctct                                                    20

SEQ ID NO: 40           moltype = DNA  length = 20
FEATURE                 Location/Qualifiers
misc_feature            1..20
                        note = primer LMO2736-R771
source                  1..20
                        mol_type = other DNA
                        organism = synthetic construct
SEQUENCE: 40
tagtccagca gcgataccac                                                    20

SEQ ID NO: 41           moltype = DNA  length = 20
FEATURE                 Location/Qualifiers
misc_feature            1..20
                        note = primer LMO2736-R992
source                  1..20
                        mol_type = other DNA
                        organism = synthetic construct
SEQUENCE: 41
ttgttttcga gtgcaaggct                                                    20

SEQ ID NO: 42           moltype = DNA  length = 20
FEATURE                 Location/Qualifiers
```

```
misc_feature            1..20
                        note = primer LMO84 F3
source                  1..20
                        mol_type = other DNA
                        organism = synthetic construct
SEQUENCE: 42
aaatgattga agtcgtacgc                                              20

SEQ ID NO: 43           moltype = DNA  length = 21
FEATURE                 Location/Qualifiers
misc_feature            1..21
                        note = primer LMO84 B3
source                  1..21
                        mol_type = other DNA
                        organism = synthetic construct
SEQUENCE: 43
gcaacctctt caattgggat a                                            21

SEQ ID NO: 44           moltype = DNA  length = 40
FEATURE                 Location/Qualifiers
misc_feature            1..40
                        note = primer LMO84 FIP
source                  1..40
                        mol_type = other DNA
                        organism = synthetic construct
SEQUENCE: 44
ctaaagcttc tccgacaagt tcaatggatg cagggattac                        40

SEQ ID NO: 45           moltype = DNA  length = 42
FEATURE                 Location/Qualifiers
misc_feature            1..42
                        note = primer LMO84 BIP
source                  1..42
                        mol_type = other DNA
                        organism = synthetic construct
SEQUENCE: 45
agaaaccatg ttcaaattgc aacagctttc tggacggcta tc                     42

SEQ ID NO: 46           moltype = DNA  length = 20
FEATURE                 Location/Qualifiers
misc_feature            1..20
                        note = primer LMO2736-1 F3
source                  1..20
                        mol_type = other DNA
                        organism = synthetic construct
SEQUENCE: 46
gaactagcct acattgatgc                                              20

SEQ ID NO: 47           moltype = DNA  length = 21
FEATURE                 Location/Qualifiers
misc_feature            1..21
                        note = primer LMO2736-1 B3
source                  1..21
                        mol_type = other DNA
                        organism = synthetic construct
SEQUENCE: 47
ttgaaccgct taataagtct g                                            21

SEQ ID NO: 48           moltype = DNA  length = 39
FEATURE                 Location/Qualifiers
misc_feature            1..39
                        note = primer LMO2736-1 FIP
source                  1..39
                        mol_type = other DNA
                        organism = synthetic construct
SEQUENCE: 48
ttcgtcacgt cacaggctat cagcaacctt aacccaaag                         39

SEQ ID NO: 49           moltype = DNA  length = 41
FEATURE                 Location/Qualifiers
misc_feature            1..41
                        note = primer LMO2736-1 BIP
source                  1..41
                        mol_type = other DNA
                        organism = synthetic construct
SEQUENCE: 49
ggagcaaaac tcgaccaatt ttcgtccagc agcgatacca c                      41

SEQ ID NO: 50           moltype = DNA  length = 22
```

```
FEATURE                 Location/Qualifiers
misc_feature            1..22
                        note = primer LMO2736-2 F3
source                  1..22
                        mol_type = other DNA
                        organism = synthetic construct
SEQUENCE: 50
caagaactag cctacattga tg                                                 22

SEQ ID NO: 51           moltype = DNA  length = 21
FEATURE                 Location/Qualifiers
misc_feature            1..21
                        note = primer LMO2736-2 B3
source                  1..21
                        mol_type = other DNA
                        organism = synthetic construct
SEQUENCE: 51
tctgcattta ggaaggtcat t                                                  21

SEQ ID NO: 52           moltype = DNA  length = 40
FEATURE                 Location/Qualifiers
misc_feature            1..40
                        note = primer LMO2736-2 FIP
source                  1..40
                        mol_type = other DNA
                        organism = synthetic construct
SEQUENCE: 52
ttcgtcacgt cacaggctat cagcaacctt aacccaaagc                              40

SEQ ID NO: 53           moltype = DNA  length = 41
FEATURE                 Location/Qualifiers
misc_feature            1..41
                        note = primer LMO2736-2 BIP
source                  1..41
                        mol_type = other DNA
                        organism = synthetic construct
SEQUENCE: 53
ggagcaaaac tcgaccaatt ttcgtccagc agcgatacca c                            41

SEQ ID NO: 54           moltype = DNA  length = 21
FEATURE                 Location/Qualifiers
misc_feature            1..21
                        note = primer LMO2736-10 F3
source                  1..21
                        mol_type = other DNA
                        organism = synthetic construct
SEQUENCE: 54
gtggcattca tttgcaagaa c                                                  21

SEQ ID NO: 55           moltype = DNA  length = 22
FEATURE                 Location/Qualifiers
misc_feature            1..22
                        note = primer LMO2736-10 B3
source                  1..22
                        mol_type = other DNA
                        organism = synthetic construct
SEQUENCE: 55
gagctgaacc gcttaataag tc                                                 22

SEQ ID NO: 56           moltype = DNA  length = 49
FEATURE                 Location/Qualifiers
misc_feature            1..49
                        note = primer LMO2736-10 FIP
source                  1..49
                        mol_type = other DNA
                        organism = synthetic construct
SEQUENCE: 56
gaagtggatt cgtcacgtca caggctacat tgatgccagc aaccttaac                    49

SEQ ID NO: 57           moltype = DNA  length = 43
FEATURE                 Location/Qualifiers
misc_feature            1..43
                        note = primer LMO2736-10 BIP
source                  1..43
                        mol_type = other DNA
                        organism = synthetic construct
SEQUENCE: 57
ctcgaccaat tttcttctca aaaatcacc accagcgggct ccg                          43
```

```
SEQ ID NO: 58          moltype = DNA   length = 19
FEATURE                Location/Qualifiers
misc_feature           1..19
                       note = F2 sequence of LMO84 FIP
source                 1..19
                       mol_type = other DNA
                       organism = synthetic construct
SEQUENCE: 58
caatggatgc agggattac                                              19

SEQ ID NO: 59          moltype = DNA   length = 18
FEATURE                Location/Qualifiers
misc_feature           1..18
                       note = B2 sequence of LMO84 BIP
source                 1..18
                       mol_type = other DNA
                       organism = synthetic construct
SEQUENCE: 59
gctttctgga cggctatc                                               18

SEQ ID NO: 60          moltype = DNA   length = 19
FEATURE                Location/Qualifiers
misc_feature           1..19
                       note = F2 sequence of LMO2736-1 FIP
source                 1..19
                       mol_type = other DNA
                       organism = synthetic construct
SEQUENCE: 60
cagcaacctt aacccaaag                                              19

SEQ ID NO: 61          moltype = DNA   length = 18
FEATURE                Location/Qualifiers
misc_feature           1..18
                       note = B2 sequence of LMO2736-1 BIP and LMO2736-2 BIP
source                 1..18
                       mol_type = other DNA
                       organism = synthetic construct
SEQUENCE: 61
gtccagcagc gataccac                                               18

SEQ ID NO: 62          moltype = DNA   length = 20
FEATURE                Location/Qualifiers
misc_feature           1..20
                       note = F2 sequence of LMO2736-2 FIP
source                 1..20
                       mol_type = other DNA
                       organism = synthetic construct
SEQUENCE: 62
cagcaacctt aacccaaagc                                             20

SEQ ID NO: 63          moltype = DNA   length = 25
FEATURE                Location/Qualifiers
misc_feature           1..25
                       note = F2 sequence of LMO2736-10 FIP
source                 1..25
                       mol_type = other DNA
                       organism = synthetic construct
SEQUENCE: 63
ctacattgat gccagcaacc ttaac                                       25

SEQ ID NO: 64          moltype = DNA   length = 15
FEATURE                Location/Qualifiers
misc_feature           1..15
                       note = B2 sequence of LMO2736-10 BIP
source                 1..15
                       mol_type = other DNA
                       organism = synthetic construct
SEQUENCE: 64
ccaccagcgg ctccg                                                  15

SEQ ID NO: 65          moltype = DNA   length = 21
FEATURE                Location/Qualifiers
misc_feature           1..21
                       note = primer LMO0833 F329
source                 1..21
                       mol_type = other DNA
                       organism = synthetic construct
SEQUENCE: 65
ggaaagcaat tgtccactcg a                                           21
```

| | | |
|---|---|---|
| SEQ ID NO: 66<br>FEATURE<br>misc_feature<br><br>source | moltype = DNA   length = 20<br>Location/Qualifiers<br>1..20<br>note = primer LMO0833_R610<br>1..20<br>mol_type = other DNA<br>organism = synthetic construct | |
| SEQUENCE: 66<br>tgttggtgag tagcgtggaa | | 20 |
| SEQ ID NO: 67<br>FEATURE<br>misc_feature<br><br>source | moltype = DNA   length = 20<br>Location/Qualifiers<br>1..20<br>note = mixed primer LMO0084-F286/M<br>1..20<br>mol_type = other DNA<br>organism = synthetic construct | |
| SEQUENCE: 67<br>agccgyccag aaagymtcaa | | 20 |
| SEQ ID NO: 68<br>FEATURE<br>misc_feature<br><br>source | moltype = DNA   length = 20<br>Location/Qualifiers<br>1..20<br>note = mixed primer LMO0084-F281/M<br>1..20<br>mol_type = other DNA<br>organism = synthetic construct | |
| SEQUENCE: 68<br>tygatagccg yccagaaagy | | 20 |
| SEQ ID NO: 69<br>FEATURE<br>misc_feature<br><br>source | moltype = DNA   length = 20<br>Location/Qualifiers<br>1..20<br>note = mixed primer LMO0084-R757/M<br>1..20<br>mol_type = other DNA<br>organism = synthetic construct | |
| SEQUENCE: 69<br>gctcgtcrgc katttctttc | | 20 |
| SEQ ID NO: 70<br>FEATURE<br>misc_feature<br><br>source | moltype = DNA   length = 20<br>Location/Qualifiers<br>1..20<br>note = mixed primer LMO2736-F222/M<br>1..20<br>mol_type = other DNA<br>organism = synthetic construct | |
| SEQUENCE: 70<br>ggccycctac ggtattcwcr | | 20 |
| SEQ ID NO: 71<br>FEATURE<br>misc_feature<br><br>source | moltype = DNA   length = 20<br>Location/Qualifiers<br>1..20<br>note = mixed primer LMO2736-F488/M<br>1..20<br>mol_type = other DNA<br>organism = synthetic construct | |
| SEQUENCE: 71<br>ccggyggyat tcatttgcaa | | 20 |
| SEQ ID NO: 72<br>FEATURE<br>misc_feature<br><br>source | moltype = DNA   length = 20<br>Location/Qualifiers<br>1..20<br>note = mixed primer LMO2736-F530/M<br>1..20<br>mol_type = other DNA<br>organism = synthetic construct | |
| SEQUENCE: 72<br>gcaayctta accaaagctg | | 20 |
| SEQ ID NO: 73<br>FEATURE<br>misc_feature<br><br>source | moltype = DNA   length = 20<br>Location/Qualifiers<br>1..20<br>note = mixed primer LMO2736-F572/M<br>1..20<br>mol_type = other DNA<br>organism = synthetic construct | |
| SEQUENCE: 73 | | |

```
cctgygacgt sacgaatcca                                                20

SEQ ID NO: 74           moltype = DNA  length = 20
FEATURE                 Location/Qualifiers
misc_feature            1..20
                        note = mixed primer LMO2736-R591/M
source                  1..20
                        mol_type = other DNA
                        organism = synthetic construct
SEQUENCE: 74
tggattcgts acgtcrcagg                                                20

SEQ ID NO: 75           moltype = DNA  length = 20
FEATURE                 Location/Qualifiers
misc_feature            1..20
                        note = mixed primer LMO2736-R685/M
source                  1..20
                        mol_type = other DNA
                        organism = synthetic construct
SEQUENCE: 75
agttctgcat ggcrykctct                                                20

SEQ ID NO: 76           moltype = DNA  length = 20
FEATURE                 Location/Qualifiers
misc_feature            1..20
                        note = mixed primer LMO2736-R771/M
source                  1..20
                        mol_type = other DNA
                        organism = synthetic construct
SEQUENCE: 76
tagtccrgca gcgataccac                                                20

SEQ ID NO: 77           moltype = DNA  length = 23
FEATURE                 Location/Qualifiers
misc_feature            1..23
                        note = oligonucleotide sequence of probe 0084TMP366-389
source                  1..23
                        mol_type = other DNA
                        organism = synthetic construct
SEQUENCE: 77
tattacattc atagaattga ccc                                            23

SEQ ID NO: 78           moltype = DNA  length = 23
FEATURE                 Location/Qualifiers
misc_feature            1..23
                        note = oligonucleotide sequence of probe 0084TMP535-558(TA)
source                  1..23
                        mol_type = other DNA
                        organism = synthetic construct
SEQUENCE: 78
atctggtggc gagaagctga aaa                                            23

SEQ ID NO: 79           moltype = DNA  length = 23
FEATURE                 Location/Qualifiers
misc_feature            1..23
                        note = oligonucleotide sequence of probe 0084TMP535-558(CC)
source                  1..23
                        mol_type = other DNA
                        organism = synthetic construct
SEQUENCE: 79
atctggtggc gagaagccga aca                                            23

SEQ ID NO: 80           moltype = DNA  length = 26
FEATURE                 Location/Qualifiers
misc_feature            1..26
                        note = oligonucleotide sequence of probe 0084TMP686-711
source                  1..26
                        mol_type = other DNA
                        organism = synthetic construct
```

```
SEQUENCE: 80
taccaagatt ccaaaaagaa gccatg                                         26

SEQ ID NO: 81            moltype = DNA  length = 20
FEATURE                  Location/Qualifiers
misc_feature             1..20
                         note = oligonucleotide sequence of probe 2736TMP70-89
source                   1..20
                         mol_type = other DNA
                         organism = synthetic construct
SEQUENCE: 81
aaaaaaggct ggactaaagc                                                20

SEQ ID NO: 82            moltype = DNA  length = 20
FEATURE                  Location/Qualifiers
misc_feature             1..20
                         note = oligonucleotide sequence of probe 2736TMP372-393
source                   1..20
                         mol_type = other DNA
                         organism = synthetic construct
SEQUENCE: 82
acgtcaaaaa aatcattatc                                                20

SEQ ID NO: 83            moltype = DNA  length = 29
FEATURE                  Location/Qualifiers
misc_feature             1..29
                         note = oligonucleotide sequence of probe 2736TMP619-647(GG)
source                   1..29
                         mol_type = other DNA
                         organism = synthetic construct
SEQUENCE: 83
gttttcggtg ctcaaaaagg ggcaagtcc                                      29

SEQ ID NO: 84            moltype = DNA  length = 29
FEATURE                  Location/Qualifiers
misc_feature             1..29
                         note = oligonucleotide sequence of probe 2736TMP619-647(CC)
source                   1..29
                         mol_type = other DNA
                         organism = synthetic construct
SEQUENCE: 84
gttttcggtg ctcaaaaagg cgcaactcc                                      29

SEQ ID NO: 85            moltype = DNA  length = 23
FEATURE                  Location/Qualifiers
misc_feature             1..23
                         note = oligonucleotide sequence of mixed probe
                           (0084TMP535-558(TA) + 0084TMP535-558(CC))
variation                18..22
                         note = ngaan is tgaaa or cgaac
source                   1..23
                         mol_type = other DNA
                         organism = synthetic construct
SEQUENCE: 85
atctggtggc gagaagcnga ana                                            23

SEQ ID NO: 86            moltype = DNA  length = 29
FEATURE                  Location/Qualifiers
misc_feature             1..29
                         note = oligonucleotide sequence of mixed probe
                           (2736TMP619-647(GG) + 2736TMP619-647(CC))
variation                21..26
                         note = ngcaan is ggcaag or cgcaac
source                   1..29
                         mol_type = other DNA
                         organism = synthetic construct
SEQUENCE: 86
gttttcggtg ctcaaaaagg ngcaantcc                                      29
```

LISTERIA-MONOCYTOGENES DETECTION METHOD

CROSS REFERENCE TO RELATED APPLICATIONS

This application is a divisional of U.S. application Ser. No. 16/632,051 filed Jan. 17, 2020, which is the National Phase of PCT International Application No. PCT/JP2017/045280, filed on Dec. 18, 2017, which claims priority under 35 U.S.C. § 119(a) to Patent Application No. 2017-141201, filed in Japan on Jul. 20, 2017, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Nov. 6, 2023, is named "0760-0513PUS2.xml" and is 127,719 bytes in size. The sequence listing contained in this .XML file is pan of the specification and is hereby incorporated by reference herein in its entirety.

TECHNICAL FIELD

The present invention relates to a method of specifically detecting *Listeria monocytogenes* and primers therefor.

BACKGROUND ART

Listeriosis is an infection caused by *Listeria monocytogenes* (which may be hereinafter referred to as "*monocytogenes* bacterium"). Among the about 10 bacterial species known for the genus *Listeria*, only the *monocytogenes* bacterium causes listeriosis in human.

In Western countries, this bacterium is regarded as a serious food-poisoning bacterium. Also in Japan, the *monocytogenes* bacterium is often detected from a variety of foods including meat products and dairy products. Since the *monocytogenes* bacterium can be killed by ordinary cooking with heat, food poisoning hardly occurs by foods requiring cooking with heat. However, since the *monocytogenes* bacterium grows even under low-temperature conditions, for example, in a refrigerator, the risk of food poisoning by the *monocytogenes* bacterium still exists even when appropriate storage is carried out at low temperature for foods eaten without cooking with heat, such as dairy products including cheese; and ham, salami, and smoked salmon.

In the official qualitative test for the *monocytogenes* bacterium, judgment for the *monocytogenes* bacterium is carried out based on formation of a colony accompanied by a milky-white halo on a selective isolation medium such as ALOA agar medium or CHROMagar medium (Non-patent Document 1). However, the genus *Listeria* includes halo-forming species other than the *monocytogenes* bacterium. Therefore, in cases of contamination with such bacteria belonging to the genus *Listeria*, they are judged as positive for the *monocytogenes* bacterium. Further, the official test using a selective isolation medium takes days to carry out the judgment since it requires several days of confirmation culture, and the confirmation culture requires skill, which is problematic.

A variety of primers for detection of the *monocytogenes* bacterium by real-time PCR or the like have been reported (for example, Patent Documents 1 and 2), and there are also commercially available kits. In these prior art techniques, genes associated with pathogenicity of the *monocytogenes* bacterium are targeted. However, since the known methods including the commercially available kits have failed to sufficiently suppress production of false negatives and false positives, they are not sufficiently satisfactory as test methods for specifically detecting only the *monocytogenes* bacterium.

PRIOR ART DOCUMENT(S)

Patent Document(s)

Patent Document 1: JP 2010-263873 A
Patent Document 2: JP 2007-61061 A

NON-PATENT DOCUMENT(S)

Non-Patent Document 1: Notification No. 1128, Article 2 of the Department of Food Safety, "Examination of *Listeria monocytogenes*", Nov. 28, 2014

SUMMARY OF THE INVENTION

Problems to be Solved by the Invention

An object of the present invention is to provide means that enables detection of the *monocytogenes* bacterium alone distinctly from other bacteria belonging to the genus *Listeria* with sufficiently high accuracy.

Means for Solving the Problems

The present inventors intensively analyzed the genome of the *monocytogenes* bacterium to identify two genes as target regions with which the *monocytogenes* bacterium can be specifically detected distinctly from other bacteria belonging to the genus *Listeria* utilizing a nucleic acid amplification method. The present inventors studied the base sequences of these two genes in more detail, and carried out an intensive study by designing a large number of primers and using a variety of combinations of the primers for genomic DNAs of *monocytogenes* bacterial strains and other bacterial strains belonging to the genus *Listeria*. As a result, the present inventors succeeded in identification of primer setting regions for specific detection of the *monocytogenes* bacterium alone with high accuracy, and also in establishment of preferred particular examples of PCR primer sets and LAMP primer sets, thereby completing the present invention.

More specifically, the present invention provides a primer set for detection of *Listeria monocytogenes*, comprising any of the following primer sets for amplification of a partial region of the lmo0084 gene or the lmo2736 gene of *Listeria monocytogenes*:

(A-1) a set of a forward primer containing in its 3'-side the base sequence of SEQ ID NO:26 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-2) a set of a forward primer containing in its 3'-side the base sequence of SEQ ID NO:26 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(A-3) a set of a forward primer containing in its 3'-side the base sequence of SEQ ID NO:27 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-4) a set of a forward primer containing in its 3'-side the base sequence of SEQ ID NO:27 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(A-5) a set of a forward primer containing in its 3'-side the base sequence of SEQ ID NO:28 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-6) a set of a forward primer containing in its 3'-side the base sequence of SEQ ID NO:28 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(A-7) a set of a forward primer containing in its 3'-side the base sequence of SEQ ID NO:29 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-8) a set of a forward primer containing in its 3'-side the base sequence of SEQ ID NO:29 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(B-1) a set of a forward primer containing in its 3'-side the base sequence of SEQ ID NO:58 or a sequence which is the same as the base sequence except that not more than 4 bases are substituted at a genetic polymorphism site(s) in the base sequence, and a reverse primer containing in its 3'-side the base sequence of SEQ ID NO:59 or a sequence which is the same as the base sequence except that not more than 4 bases are substituted at a genetic polymorphism site(s) in the base sequence;

(C-1) a set of a forward primer containing in its 3'-side the base sequence of SEQ ID NO:32 or a sequence which is the same as the base sequence except that not more than 4 bases are substituted at a genetic polymorphism site(s) in the base sequence, and a reverse primer containing in its 3'-side the base sequence of SEQ ID NO:37 or a sequence which is the same as the base sequence except that not more than 4 bases are substituted at a genetic polymorphism site(s) in the base sequence;

(D-1) a set of a forward primer containing in its 3'-side the base sequence of SEQ ID NO:33 or a sequence which is the same as the base sequence except that not more than 4 bases are substituted at a genetic polymorphism site(s) in the base sequence, and a reverse primer containing in its 3'-side the base sequence of SEQ ID NO:38 or a sequence which is the same as the base sequence except that not more than 4 bases are substituted at a genetic polymorphism site(s) in the base sequence;

(E-1) a set of a forward primer containing in its 3'-side the base sequence of SEQ ID NO:34 or a sequence which is the same as the base sequence except that not more than 4 bases are substituted at a genetic polymorphism site(s) in the base sequence, and a reverse primer containing in its 3'-side the base sequence of SEQ ID NO:38 or a sequence which is the same as the base sequence except that not more than 4 bases are substituted at a genetic polymorphism site(s) in the base sequence;

(F-1) a set of a forward primer containing in its 3'-side the base sequence of SEQ ID NO:34 or a sequence which is the same as the base sequence except that not more than 4 bases are substituted at a genetic polymorphism site(s) in the base sequence, and a reverse primer containing in its 3'-side the base sequence of SEQ ID NO:39 or a sequence which is the same as the base sequence except that not more than 4 bases are substituted at a genetic polymorphism site(s) in the base sequence;

(G-1) a set of a forward primer containing in its 3'-side the base sequence of SEQ ID NO:34 or a sequence which is the same as the base sequence except that not more than 4 bases are substituted at a genetic polymorphism site(s) in the base sequence, and a reverse primer containing in its 3'-side the base sequence of SEQ ID NO:40 or a sequence which is the same as the base sequence except that not more than 4 bases are substituted at a genetic polymorphism site(s) in the base sequence;

(H-1) a set of a forward primer containing in its 3'-side the base sequence of SEQ ID NO:35 or a sequence which is the same as the base sequence except that not more than 4 bases are substituted at a genetic polymorphism site(s) in the base sequence, and a reverse primer containing in its 3'-side the base sequence of SEQ ID NO:39 or a sequence which is the same as the base sequence except that not more than 4 bases are substituted at a genetic polymorphism site(s) in the base sequence;

(I-1) a set of a forward primer containing in its 3'-side the base sequence of SEQ ID NO:35 or a sequence which is the same as the base sequence except that not more than 4 bases are substituted at a genetic polymorphism site(s) in the base sequence, and a reverse primer containing in its 3'-side the base sequence of SEQ ID NO:40 or a sequence which is the same as the base sequence except that not more than 4 bases are substituted at a genetic polymorphism site(s) in the base sequence;

(I-2) a set of a forward primer containing in its 3'-side the base sequence of SEQ ID NO:60 or a sequence which is the same as the base sequence except that not more than 4 bases are substituted at a genetic polymorphism site(s) in the base sequence, and a reverse primer containing in its 3'-side the base sequence of SEQ ID NO:61 or a sequence which is the same as the base sequence except that not more than 4 bases are substituted at a genetic polymorphism site(s) in the base sequence;

(I-3) a set of a forward primer containing in its 3'-side the base sequence of SEQ ID NO:62 or a sequence which is the same as the base sequence except that not more than 4 bases are substituted at a genetic polymorphism site(s) in the base sequence, and a reverse primer containing in its 3'-side the base sequence of SEQ ID NO:61 or a sequence which is the same as the base sequence except that not more than 4 bases are substituted at a genetic polymorphism site(s) in the base sequence;

(J-1) a set of a forward primer containing in its 3'-side the base sequence of SEQ ID NO:35 or a sequence which is the same as the base sequence except that not more than 4 bases are substituted at a genetic polymorphism site(s) in the base sequence, and a reverse primer containing in its 3'-side the base sequence of SEQ ID NO:41 or a sequence which is the same as the base sequence except that not more than 4 bases are substituted at a genetic polymorphism site(s) in the base sequence;

(K-1) a set of a forward primer containing in its 3'-side the base sequence of SEQ ID NO:36 or a sequence which is the same as the base sequence except that not more than 4 bases are substituted at a genetic polymorphism site(s) in the base sequence, and a reverse primer containing in its 3'-side the base sequence of SEQ ID NO:39 or a sequence which is the same as the base sequence except that not more than 4 bases are substituted at a genetic polymorphism site(s) in the base sequence;

(L-1) a set of a forward primer containing in its 3'-side the base sequence of SEQ ID NO:36 or a sequence which is the same as the base sequence except that not more than 4 bases are substituted at a genetic polymorphism site(s) in the base sequence, and a reverse primer containing in its 3'-side the base sequence of SEQ ID NO:40 or a sequence which is the same as the base sequence except that not more than 4 bases are substituted at a genetic polymorphism site(s) in the base sequence; and (M-1) a set of a forward primer containing in its 3'-side the base sequence of SEQ ID NO:63 or a sequence which is the same as the base sequence except that not more than 4 bases are substituted at a genetic polymorphism site(s) in the base sequence, and a reverse primer containing in its 3'-side the base sequence of SEQ ID NO:64 or a sequence which is the same as the base sequence except that not more than 4 bases are substituted at a genetic polymorphism site(s) in the base sequence.

The present invention also provides a primer set for detection of *Listeria monocytogenes*, comprising any of the following sets:

(A-9) a set of a mixed forward primer containing in its 3'-side the base sequence of SEQ ID NO:67, and a mixed reverse primer containing in its 3'-side the base sequence of SEQ ID NO:69;

(A-10) a set of a mixed forward primer containing in its 3'-side the base sequence of SEQ ID NO:68, and a mixed reverse primer containing in its 3'-side the base sequence of SEQ ID NO:69;

(D-2) a set of a mixed forward primer containing in its 3'-side the base sequence of SEQ ID NO:70, and a mixed reverse primer containing in its 3'-side the base sequence of SEQ ID NO:74;

(E-2) a set of a mixed forward primer containing in its 3'-side the base sequence of SEQ ID NO:71, and a mixed reverse primer containing in its 3'-side the base sequence of SEQ ID NO:74;

(F-2) a set of a mixed forward primer containing in its 3'-side the base sequence of SEQ ID NO:71, and a mixed reverse primer containing in its 3'-side the base sequence of SEQ ID NO:75;

(G-2) a set of a mixed forward primer containing in its 3'-side the base sequence of SEQ ID NO:71, and a mixed reverse primer containing in its 3'-side the base sequence of SEQ ID NO:76;

(H-2) a set of a mixed forward primer containing in its 3'-side the base sequence of SEQ ID NO:72, and a mixed reverse primer containing in its 3'-side the base sequence of SEQ ID NO:75;

(I-4) a set of a mixed forward primer containing in its 3'-side the base sequence of SEQ ID NO:72, and a mixed reverse primer containing in its 3'-side the base sequence of SEQ ID NO:76;

(J-2) a set of a mixed forward primer containing in its 3'-side the base sequence of SEQ ID NO:72, and a reverse primer containing in its 3'-side the base sequence of SEQ ID NO:41 or a sequence which is the same as the base sequence except that not more than 4 bases are substituted at a genetic polymorphism site(s) in the base sequence;

(K-3) a set of a mixed forward primer containing in its 3'-side the base sequence of SEQ ID NO:73, and a mixed reverse primer containing in its 3'-side the base sequence of SEQ ID NO:75;

(L-2) a set of a mixed forward primer containing in its 3'-side the base sequence of SEQ ID NO:73, and a mixed reverse primer containing in its 3'-side the base sequence of SEQ ID NO:76;

(N-1) a set of a mixed forward primer containing in its 3'-side the base sequence of SEQ ID NO:71, and a reverse primer containing in its 3'-side the base sequence of SEQ ID NO:41 or a sequence which is the same as the base sequence except that not more than 4 bases are substituted at a genetic polymorphism site(s) in the base sequence; and (O-1) a set of a mixed forward primer containing in its 3'-side the base sequence of SEQ ID NO:73, and a reverse primer containing in its 3'-side the base sequence of SEQ ID NO:41 or a sequence which is the same as the base sequence except that not more than 4 bases are substituted at a genetic polymorphism site(s) in the base sequence.

The present invention also provides a loop-mediated isothermal amplification primer set for detection of *Listeria monocytogenes*, comprising any of the following sets:
  (i) a set of an F3 primer composed of the base sequence of SEQ ID NO:42, a B3 primer composed of the base sequence of SEQ ID NO:43, an FIP primer composed of the base sequence of SEQ ID NO:44, and a BIP primer composed of the base sequence of SEQ ID NO:45;
  (ii) a set of an F3 primer composed of the base sequence of SEQ ID NO:46, a B3 primer composed of the base sequence of SEQ ID NO:47, an FIP primer composed of the base sequence of SEQ ID NO:48, and a BIP primer composed of the base sequence of SEQ ID NO:49;
  (iii) a set of an F3 primer composed of the base sequence of SEQ ID NO:50, a B3 primer composed of the base sequence of SEQ ID NO:51, an FIP primer composed of the base sequence of SEQ ID NO:52, and a BIP primer composed of the base sequence of SEQ ID NO:53; and
  (iv) a set of an F3 primer composed of the base sequence of SEQ ID NO:54, a B3 primer composed of the base sequence of SEQ ID NO:55, an FIP primer composed of the base sequence of SEQ ID NO:56, and a BIP primer composed of the base sequence of SEQ ID NO:57.

The present invention also provides a method of detecting *Listeria monocytogenes*, comprising a step of amplifying a partial region of the lmo0084 gene or the lmo2736 gene by a nucleic acid amplification method using the primer set of the present invention described above.

The present invention also provides a probe for detection of *Listeria monocytogenes*, comprising an oligonucleotide portion having the base sequence of SEQ ID NO:77, SEQ ID NOs:80 to 82, SEQ ID NO:85 (wherein ngaan is tgaaa or cgaac), or SEQ ID NO:86 (wherein ngcaan is ggcaag or cgcaac).

The present invention also provides a primer-probe set for real-time PCR for detection of *Listeria monocytogenes*, comprising any of the following sets of primers and a probe:
  [1] a set of a forward primer containing in its 3'-side the base sequence of SEQ ID NO:67, a reverse primer containing in its 3'-side the base sequence of SEQ ID NO:69, and a probe containing an oligonucleotide portion having the base sequence of SEQ ID NO:77 or 80;
  [2] a set of a forward primer containing in its 3'-side the base sequence of SEQ ID NO:67, a reverse primer containing in its 3'-side the base sequence of SEQ ID NO:69, and a mixed probe containing an oligonucleotide portion having the base sequence of SEQ ID NO:85 (wherein ngaan is tgaaa or cgaac);
  [3] a set of a forward primer containing in its 3'-side the base sequence of SEQ ID NO:68, a reverse primer containing in its 3'-side the base sequence of SEQ ID NO:69, and a probe containing an oligonucleotide portion having the base sequence of SEQ ID NO:77 or 80;
  [4] a set of a forward primer containing in its 3'-side the base sequence of SEQ ID NO:68, a reverse primer containing in its 3'-side the base sequence of SEQ ID NO:69, and a mixed probe containing an oligonucleotide portion having the base sequence of SEQ ID NO:85 (wherein ngaan is tgaaa or cgaac);
  [5] a set of a forward primer containing in its 3'-side the base sequence of SEQ ID NO:32, a reverse primer containing in its 3'-side the base sequence of SEQ ID NO:37, and a probe containing an oligonucleotide portion having the base sequence of SEQ ID NO:81; and
  [6] a set of a forward primer containing in its 3'-side the base sequence of SEQ ID NO:70, a reverse primer containing in its 3'-side the base sequence of SEQ ID NO:74, and a probe containing an oligonucleotide portion having the base sequence of SEQ ID NO:82; and
  [7] a set of a forward primer containing in its 3'-side the base sequence of SEQ ID NO:72, a reverse primer containing in its 3'-side the base sequence of SEQ ID NO:76, and a mixed probe containing an oligonucleotide portion having the base sequence of SEQ ID NO:86 (wherein ngcaan is ggcaag or cgcaac).

Effect of the Invention

According to the present invention, primers with which various bacterial strains of the *monocytogenes* bacterium can be specifically detected distinctly from other bacteria belonging to the genus *Listeria* are provided. According to the method of the present invention, occurrence of false negatives and false positives can be remarkably reduced compared to test methods based on conventional nucleic acid amplification methods. Bacteria belonging to the genus *Listeria* also include species other than the *monocytogenes* bacterium that form colonies accompanied by milky-white halos on a selective isolation medium. According to the present invention, no amplification occurs with those bacterial strains, and such bacterial strains can therefore be distinguished from the *monocytogenes* bacterium even based on the result of a nucleic acid amplification method alone. Further, serotypes of the *monocytogenes* bacterium can be identified by designing probes targeting polymorphic sequences characteristic to the individual serotypes, such as the TaqMan (registered trademark) probe 0084TMP535-558 (CC) in the following Examples, and carrying out real-time PCR.

BRIEF DESCRIPTION OF THE DRAWINGS

FIG. 1-2 shows images of colonies obtained by culturing species belonging to the genus *Listeria* other than the *monocytogenes* bacterium on ALOA agar medium or CHROMagar medium (examples of images of a false-positive colony forming a halo).

FIG. 1-3 shows images of colonies obtained by culturing species belonging to the genus *Listeria* other than the *monocytogenes* bacterium on ALOA agar medium or CHROMagar medium (examples of images of a negative colony forming no halo).

FIG. 2-1 shows an example of the result of PCR using PCR primers for detection of *Listeria monocytogenes* designed in Examples. The PCR was carried out using Prime set No. 4, which targets the lmo00084 gene. Detection was carried out by 2% agarose gel electrophoresis. The 476-bp PCR products indicated by arrows are specific amplification products from the *monocytogenes* bacterium. The number assigned to each lane corresponds to a bacterial strain No. listed in Table 5-1 or Table 5-2. The numbers 1 to 10 correspond to *monocytogenes* (corresponding, from No. 1, to the serotypes 1/2a, 1/2b, l/2c, 3a, 3b, 3c, 4a, 4b, 4d, and 5 in this order), and the numbers 11 to 22 correspond to species belonging to the genus *Listeria* other than *monocytogenes*.

FIG. 2-2 shows an example of the result of PCR using PCR primers for detection of *Listeria monocytogenes* designed in Examples. The PCR was carried out using Prime set No. 1, which targets the lmo02736 gene. Detection was carried out by 2% agarose gel electrophoresis. The 168-bp PCR products indicated by arrows are specific amplification products from the *monocytogenes* bacterium. The arrows indicate the specific amplification products. The number assigned to each lane is the same as in FIG. 2-1.

MODE FOR CARRYING OUT THE INVENTION

Figure 1:
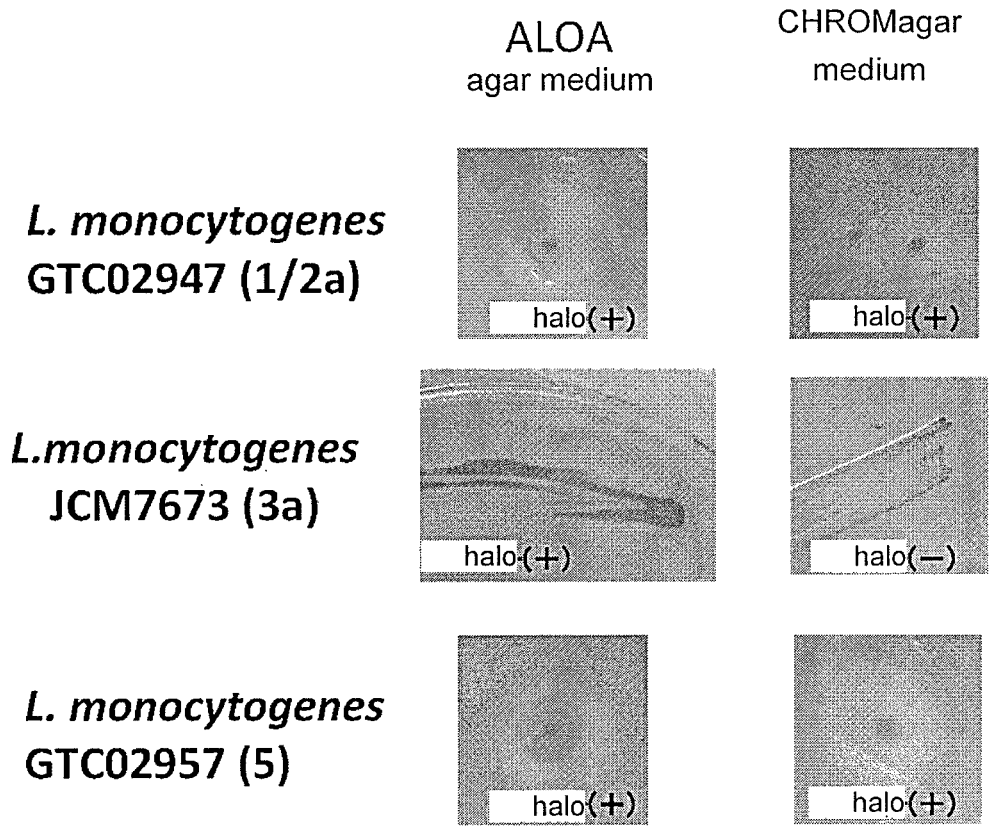
FIG. 1-1 shows images of colonies obtained by culturing the *monocytogenes* bacterium on ALOA agar medium or CHROMagar medium (examples of images of a positive colony forming a halo or a false-negative colony forming no halo).

One of the following two genes present in the genome of the *monocytogenes* bacterium is the target to be detected in the present invention.

TABLE 1

| Gene name (*) | Gene length | Gene type | Description |
| --- | --- | --- | --- |
| lmo0084 | 984 | CDS | similar to oxidoreductases |
| lmo2736 | 1134 | CDS | conserved hypothetical protein |

(*) In the genomic sequence information of GenBank Accession No. AL591824.1, the lmo0084 gene corresponds to the region of 86747-87744, and lmo2736 corresponds to the region of 2811788-2812921.

SEQ ID NOs: 1 to 12 in SEQUENCE LISTING show base sequences of the lmo0084 gene in the serotypes 1/2a, 1/2b, 1/2c, 3a, 3b, 3c, 4a, 4b, 4c, 4d, 4e, and 7, respectively, of the *monocytogenes* bacterium. SEQ ID NOs:13 to 25 show base sequences of the lmo2736 gene of the above individual serotypes of the *monocytogenes* bacterium (regarding 4b, two kinds of base sequences are shown as SEQ ID NOs:20 and 21). In the present description, specification of partial regions of each gene is carried out using, as a standard, the base sequence in the serotype 1/2a shown in SEQ ID NO:1 for the lmo0084 gene, or the base sequence in the serotype 1/2a shown in SEQ ID NO:13 for the lmo2736 gene. For example, "the region of position 306 to position 737 in the lmo0084 gene shown in SEQ ID NO:1" includes the region of position 306 to position 737 in the lmo0084 gene of various serotypes. The same applies to the lmo2736 gene. The accession numbers of the sequences of SEQ ID NOs:1 to 25 are as shown below in Table 2.

TABLE 2

| SEQ ID NO. | Gene name | Serotype | Accession No. |
| --- | --- | --- | --- |
| 1 | lmo0084 | 1/2a | NC_018592.1 |
| 2 | lmo0084 | 1/2b | NC_018587.1 |
| 3 | lmo0084 | 1/2c | NC_018588.1 |
| 4 | lmo0084 | 3a | NC_018593.1 |
| 5 | lmo0084 | 3b | NC_018586.1 |
| 6 | lmo0084 | 3c | NC_018589.1 |

TABLE 2-continued

| SEQ ID NO. | Gene name | Serotype | Accession No. |
| --- | --- | --- | --- |
| 7 | lmo0084 | 4a | NC_017529.1 |
| 8 | lmo0084 | 4b | NC_019556.1 |
| 9 | lmo0084 | 4c | NC_018590.1 |
| 10 | lmo0084 | 4d | NC_018584.1 |
| 11 | lmo0084 | 4e | NC_018585.1 |
| 12 | lmo0084 | 7 | NC_018591.1 |
| 13 | lmo2736 | 1/2a | NC_018592.1 |
| 14 | lmo2736 | 1/2b | NC_018587.1 |
| 15 | lmo2736 | 1/2c | NC_018588.1 |
| 16 | lmo2736 | 3a | NC_018593.1 |
| 17 | lmo2736 | 3b | NC_018586.1 |
| 18 | lmo2736 | 3c | NC_018589,1 |
| 19 | lmo2736 | 4a | NC_017529.1 |
| 20 | lmo2736 | 4b | NC_019556.1 |
| 21 | lmo2736 | 4b | NC_018642.1 |
| 22 | lmo2736 | 4c | NC_018590.1 |
| 23 | lmo2736 | 4d | NC_018584.1 |
| 24 | lmo2736 | 4e | NC_018585.1 |
| 25 | lmo2736 | 7 | NC_018591.1 |

The specific detection of the *monocytogenes* bacterium can be carried out by a nucleic acid amplification method using a primer(s) for detection of *Listeria monocytogenes*, which primer(s) specifically hybridize(s) to a region in the lmo0084 gene or the lmo2736 gene. As the nucleic acid amplification method, various known methods such as the PCR method or the isothermal amplification method may be used. In the present invention, the term "primer" includes PCR primers and isothermal amplification primers. In the present invention, the PCR method means a nucleic acid amplification method in which the temperature is repeatedly changed to amplify a region of interest.

The term "specifically hybridizes" means that, under normal hybridization conditions, the primer hybridizes only to a target region, and does not substantially hybridize to other regions. The term "under normal hybridization conditions" means that a reaction is carried out under conditions used for annealing in normal PCR, for example, at an appropriate annealing temperature of about 54° C. to 60° C. using a common buffer such as 50 mM KCl, 10 mM Tris-HCl (pH 8.3 to 9.0), 1.5 mM $MgCl_2$ in cases of PCR using Taq polymerase. However, the appropriate annealing temperature is not limited to the above example, and may be determined based on the Tm value of the primer and an empirical rule by the experimenter. Those skilled in the art can easily determine the temperature. The term "does not substantially hybridize" means that the primer does not hybridize at all, or, even in cases where it hybridizes, a much smaller amount of the primer hybridizes compared to the case where the primer hybridizes to the target region, so that only a relatively ignorable, small amount of the primer hybridizes.

For detection of the amplification product obtained by the nucleic acid amplification method, any known detection method may be applied. In cases of the PCR method, the detection may be carried out by electrophoresis, the intercalation method, the quencher-mediated fluorescence detection method, or the like, and, in cases of the isothermal amplification method, the detection may be carried out by a method in which pyrophosphoric acid as an amplification by-product is insolubilized, the intercalation method, the quencher-mediated fluorescence detection method, or the like. Alternatively, the amplification product may be detected by nucleic acid chromatography.

The term "PCR method" also includes the real-time PCR method. In real-time PCR, detection and monitoring of the amplification product are commonly carried out by the intercalation method or the quencher-mediated fluorescence detection method. In the following Examples, a specific example of the real-time PCR detection system using the TaqMan (registered trademark) probe method as one example of the quencher-mediated fluorescence detection method is described. However, the detection method is not limited thereto, and a variety of methods may be employed.

In cases of nucleic acid chromatography, the detection is possible by carrying out nucleic acid amplification using a primer set for detection of the *monocytogenes* bacterium of the invention, and then developing the resulting amplification product on a strip on which a capture substance that specifically binds to the amplification product is immobilized in the shape of a line or the like. For capturing the amplification product, for example, a labeling compound such as biotin or DIG, or an arbitrary base sequence may be added to the 5-side of the forward or reverse primer, and a labeling-compound-specific binding substance such as avidin or an anti-DIG antibody, or an oligonucleotide probe having a base sequence complementary to the arbitrary base sequence may be immobilized as the capture substance on the strip. For further increasing the specificity of the detection, as the capture probe on the strip, a probe having a base sequence that specifically hybridizes to a certain partial sequence in the region amplified by the primers may be used. In order to provide such a capture probe, a partial region in the region amplified by the primers may be appropriately selected, and a probe capable of hybridizing to the amplification product of each serotype may be designed with reference to the base sequence of the lmo0084 gene of each serotype of SEQ ID NOs:1 to 12 or the base sequence of the lmo2736 gene of each serotype of SEQ ID NOs:13 to 25. The detection system may be constructed in the same manner as in a known nucleic acid chromatography method, and examples of the detection system include coloring detection methods using an enzyme such as peroxidase or using particles such as colloidal gold or colored latex.

The isothermal amplification method is not limited, and various isothermal amplification methods such as the Loop-Mediated Isothermal Amplification (LAMP) method, the Strand Displacement Amplification (SDA) method, the Isothermal and Chimeric primer-initiated Amplification of Nucleic acids (ICAN) method, the Helicase-Dependent Amplification (HDA) method, and the Nicking Enzyme Amplification Reaction (NEAR) method may be employed. Examples of the isothermal amplification primers include the LAMP primers designed in the following Examples.

In the present invention, typical samples to be tested are samples collected from foods (including raw materials and processed foods). However, the samples to be tested are not limited thereto, and include a variety of samples whose test for the *monocytogenes* bacterium is desired, such as swabs from production lines and fingers of workers in food factories.

As a primer set to be used for the nucleic acid amplification method such as the PCR method or the isothermal amplification method for specifically detecting the *monocytogenes* bacterium distinctly from other bacteria belonging to the genus *Listeria* and from other food-poisoning microbes, a primer set which specifically hybridizes to a region in the lmo0084 gene sequence of SEQ ID NO:1 or the lmo2736 gene sequence of SEQ ID NO:13 may be used. The primer set may be designed taking into account the primer length, the GC content, the Tm value, bias of bases, contiguous sequences, complementarity inside and between primers, the molecular weight of the amplification product, genetic polymorphisms in the target region, and the like. In cases where the primer set is used in the PCR method, it may be designed to have a length of about 15 to 30 bases, a GC content of about 40 to 60%, and a Tm value of about 50 to WPC. For a nucleic acid amplification method other than the PCR method, the primer set may be designed according to the principle of the method, for example, as in the LAMP method described below.

Each primer constituting such a primer set is generally preferably designed for a region having less sequence diversity among serotypes, but may also be designed in a region having a small number of genetic polymorphisms. In cases where the primer is designed for a region containing a genetic polymorphism(s), the primer may be designed such that a base substitution(s) reflecting the genetic polymorphism(s) is/are added to the gene sequence in the serotype 1/2a of SEQ ID NO:1 or SEQ ID NO:13. The number of the base substitution(s) reflecting the genetic polymorphism(s) is preferably not more than 20%, more preferably not more than 15% per primer. More specifically, in cases of a primer having a chain length of 20 bases containing no additional sequence, the primer may be designed to have a sequence in which not more than 4, preferably not more than 3 bases are substituted at a genetic polymorphism site(s) in the 20-base region. In some cases, the thus designed primer may have a sequence identical to the sequence of a partial region of the gene sequence of another serotype, or the complementary strand thereof. In cases where primers containing substitutions at a genetic polymorphism site(s) are used, primers for the individual genetic polymorphisms may be used; a primer mixture prepared by mixing the primers for the individual genetic polymorphisms may be used; or a mixed primer synthesized such that the genetic polymorphism site(s) has/have mixed bases according to the genetic polymorphisms (for example, when some serotypes have G while other serotypes have C as the base at a certain site, a mixed primer prepared such that the base at the site is S (G or C)); may be used.

In the present invention, a primer for specifically detecting the *monocytogenes* bacterium may be designed such that the primer specifically hybridizes to any of the following regions (1) to (14) taking the above factors into account.

(1) The region of position 261 to position 325 of the lmo0084 gene sequence of SEQ ID NO:1, or the region complementary to this region.

LMO00844-F286A (SEQ ID NO:26). LMO0084-F286B (SEQ ID NO:27). LMO0084-F281A (SEQ ID NO:28), and LMO0084-F281B (SEQ ID NO:29) in Examples are specific examples of a forward primer that hybridizes to the region complementary to the region of position 261 to position 325. LMO0084-F286/M (SEQ ID NO:67) and LMO0084-F281/M (SEQ ID NO:68) are specific examples of a mixed forward primer that hybridizes to the region complementary to this region. Primers containing the base sequence of SEQ ID NO:59 in the 3'-side thereof, such as the LAMP primer LMO84 BIP (SEQ ID NO:45) in Examples, are specific examples of a reverse primer that hybridizes to the region of position 261 to position 325.

(2) The region of position 718 to position 777 of the lmo0084 gene sequence of SEQ ID NO: 1, or the region complementary to this region.

LMO0084-R757A (SEQ ID NO:30) and LMO0084-R757B (SEQ ID NO:31) in Examples are specific examples of a reverse primer that hybridizes to the region of position 718 to position 777. LMO0084-R757/M (SEQ ID NO:69) is a specific example of a mixed reverse primer that hybridizes to this region.

(3) The region of position 108 to position 166 of the lmo0084 gene sequence of SEQ ID NO:1, or the region complementary to this region.

Primers containing the base sequence of SEQ ID NO:58 in the 3'-side thereof, such as the LAMP primer LMO84 FIP (SEQ ID NO:44) in Examples, are specific examples of a forward primer that hybridizes to the region complementary to the region of position 108 to position 166.

(4) The region of position 1 to position 47 of the lmo2736 gene sequence of SEQ ID NO:13, or the region complementary to this region.

LMO2736-F8 (SEQ ID NO:32) in Examples is a specific example of a forward primer that hybridizes to the region complementary to the region of position 1 to position 47.

(5) The region of position 202 to position 261 of the lmo2736 gene sequence of SEQ ID NO:13, or the region complementary to this region.

LMO2736-F222 (SEQ ID NO:33) in Examples is a specific example of a forward primer that hybridizes to the region complementary to the region of position 202 to position 261. LMO2736-F222/M (SEQ ID NO:70) is a specific example of a mixed forward primer that hybridizes to the region complementary to this region.

(6) The region of position 468 to position 527 of the lmo2736 gene sequence of SEQ ID NO:13, or the region complementary to this region.

LMO2736-F488 (SEQ ID NO:34) in Examples is a specific example of a forward primer that hybridizes to the region complementary to the region of position 468 to position 527. LMO2736-F488/M (SEQ ID NO:71) is a specific example of a mixed forward primer that hybridizes to the region complementary to this region.

(7) The region of position 510 to position 569 of the lmo2736 gene sequence of SEQ ID NO:13, or the region complementary to this region.

LMO2736-F530 (SEQ ID NO:35) in Examples, and primers containing the base sequence of SEQ ID NO:60 or 62 in the 3'-side thereof, such as LMO2736-1 FIP (SEQ ID NO:48) and LMO2736-2 FIP (SEQ ID NO:52) in Examples, are specific examples of a forward primer that hybridizes to the region complementary to the region of position 510 to position 569. LMO2736-F530/M (SEQ ID NO:72) is a specific example of a mixed forward primer that hybridizes to the region complementary to this region.

(8) The region of position 552 to position 611 of the lmo2736 gene sequence of SEQ ID NO:13, or the region complementary to this region.

LMO2736-F572 (SEQ ID NO:36) is a specific example of a forward primer that hybridizes to the region complementary to the region of position 552 to position 611; LMO2736-F572/M (SEQ ID NO:73) is a specific example of a mixed forward primer that hybridizes to the region complementary to this region; and LMO2736-R591 (SEQ ID NO:38) is a specific example of a reverse primer that hybridizes to the region of position 552 to position 611.

(9) The region of position 137 to position 196 of the lmo2736 gene sequence of SEQ ID NO:13, or the region complementary to this region.

LMO2736-R176 (SEQ ID NO:37) in Examples is a specific example of a reverse primer that hybridizes to the region of position 137 to position 196.

(10) The region of position 646 to position 705 of the lmo2736 gene sequence of SEQ ID NO: 13, or the region complementary to this region.

LMO2736-8685 (SEQ ID NO:39) in Examples is a specific example of a reverse primer that hybridizes to the region of position 646 to position 705. LMO2736-R6851M (SEQ ID NO:75) is a specific example of a mixed reverse primer that hybridizes to this region.

(11) The region of position 732 to position 791 of the lmo2736 gene sequence of SEQ ID NO:13, or the region complementary to this region.

LMO2736-R771 (SEQ ID NO:40) in Examples, and primers containing the base sequence of SEQ ID NO:61 in the 3'-side thereof, such as LMO2736-1 BIP (SEQ ID NO:49) and LMO2736-2 BIP (SEQ ID NO:53) in Examples, are specific examples of a reverse primer that hybridizes to the region of position 732 to position 791. LMO2736-R771/M (SEQ ID NO:76) is a specific example of a mixed reverse primer that hybridizes to this region.

(12) The region of position 953 to position 1012 of the lmo2736 gene sequence of SEQ ID NO:13, or the region complementary to this region.

LMO2736-R992 (SEQ ID NO:41) in Examples is a specific example of a reverse primer that hybridizes to the region of position 953 to position 1012.

(13) The region of position 496 to position 560 of the lmo2736 gene sequence of SEQ ID NO:13, or the region complementary to this region.

Primers containing the base sequence of SEQ ID NO:63 in the 3'-side thereof, such as the LAMP primer LMO2736-10 FIP (SEQ ID NO:56) in Examples, are specific examples of a forward primer that hybridizes to the region complementary to the region of position 496 to position 560.

(14) The region of position 721 to position 775 of the lmo2736 gene sequence of SEQ ID NO:13, or the region complementary to this region.

Primers containing the base sequence of SEQ ID NO:64 in the 3'-side thereof, such as the LAMP primer LMO2736-10 BIP (SEQ ID NO:57) in Examples, are specific examples of a reverse primer that hybridizes to the region of position 721 to position 775.

The primers that specifically hybridize to the regions (1) to (3) of the lmo0084 gene may be, for example, primers each containing in its 3'-side a sequence having not less than 15 consecutive bases, preferably not less than 18 consecutive bases in the region of position 261 to position 325, the region of position 718 to position 777, or the region of position 108 to position 166 in the base sequence of SEQ ID NO:1, or in the region complementary to any of these; or a sequence which is the same as this sequence except that not more than 20% of bases are substituted at a genetic polymorphism site(s) therein.

The primers that specifically hybridize to the regions (4) to (14) of the lmo2736 gene may be, for example, primers each containing in its 3'-side a sequence having not less than 15 consecutive bases, preferably not less than 18 consecutive bases in the region of position 1 to position 47, the region of position 202 to position 261, the region of position 468 to position 527, the region of position 510 to position 569, the region of position 552 to position 611, the region of position 137 to position 196, the region of position 646 to position 705, the region of position 732 to position 791, the region of position 953 to position 1012, the region of position 496 to position 560, or the region of position 721 to position 775 in the base sequence of SEQ ID NO:13, or in the region complementary to any of these; or a sequence which is the same as this sequence except that not more than 20% of bases are substituted at a genetic polymorphism site(s) therein.

Specific examples of a preferred sequence that can be employed for a primer for amplifying/detecting a partial region of the lmo0084 gene include SEQ ID NOs:26 to 31, 58, and 59. SEQ ID NOs:58 and 59 are 3'-sick partial sequences of SEQ ID NOs:44 and 45, which are LAMP primer sequences (sequences of the F2 or B2 portion, which hybridize to target sites in the lmo0084 gene). SEQ ID NOs:26 to 29 and 58 are sequences of the sense strand of the lmo0084 gene, and can be used as the sequences of forward primers that hybridize to the antisense strand of the gene. SEQ ID NOs:30, 31, and 59 are sequences of the antisense strand of the lmo0084 gene, and can be used as sequences of reverse primers that hybridize to the sense strand of the gene.

Specific examples of a preferred sequence that can be employed for a primer for amplifying/detecting a partial region of the lmo2736 gene include SEQ ID NOs:32 to 41, and 60 to 64. SEQ ID NOs:60 to 64 are 3'-side partial sequences of SEQ ID NOs:48, 49, 52, 53, 56, and 57, which are LAMP primer sequences (sequences of the F2 or B2 portion, which hybridize to target sites in the lmo2736 gene). SEQ ID NOs:32 to 36, 60, 62, and 63 are sequences of the sense strand of the lmo2736 gene, and can be used as the sequences of forward primers that hybridize to the antisense strand of the gene. SEQ ID NOs:37 to 41, 61, and 64 are sequences of the antisense strand of the lmo2736 gene, and can be used as sequences of reverse primers that hybridize to the sense strand of the gene.

SEQ ID NOs:26 to 31 and SEQ ID NOs:32 to 41, which were mentioned as preferred specific examples of sequences that can be employed for primers for amplifying/detecting a partial region of the lmo0084 gene or the lmo2736 gene, can be used as LAMP primers by providing an additional sequence to the 5'-side thereof as described below.

Examples of the set of a forward primer and a reverse primer for amplification of a partial region of the lmo0084 gene or the lmo2736 gene of the *monocytogenes* bacterium, designed for the regions (1) to (14), include primer sets containing any of the following. The primer set may be PCR primers, or isothermal amplification primers such as LAMP primers.

(A) A set of a forward primer that hybridizes to the region (1) and a reverse primer that hybridizes to the region (2).
(B) A set of a forward primer that hybridizes to the region (3) and a reverse primer that hybridizes to the region (1).
(C) A set of a forward primer that hybridizes to the region (4) and a reverse primer that hybridizes to the region (9).
(D) A set of a forward primer that hybridizes to the region (5) and a reverse primer that hybridizes to the region (8).
(E) A set of a forward primer that hybridizes to the region (6) and a reverse primer that hybridizes to the region (8).
(F) A set of a forward primer that hybridizes to the region (6) and a reverse primer that hybridizes to the region (10).
(G) A set of a forward primer that hybridizes to the region (6) and a reverse primer that hybridizes to the region (11).
(H) A set of a forward primer that hybridizes to the region (7) and a reverse primer that hybridizes to the region (10).
(I) A set of a forward primer that hybridizes to the region (7) and a reverse primer that hybridizes to the region (11).
(J) A set of a forward primer that hybridizes to the region (7) and a reverse primer that hybridizes to the region (12).
(K) A set of a forward primer that hybridizes to the region (8) and a reverse primer that hybridizes to the region (10).
(L) A set of a forward primer that hybridizes to the region (8) and a reverse primer that hybridizes to the region (11).
(M) A set of a forward primer that hybridizes to the region (13) and a reverse primer that hybridizes to the region (14).
(N) A set of a forward primer that hybridizes to the region (6) and a reverse primer that hybridizes to the region (12).
(O) A set of a forward primer that hybridizes to the region (8) and a reverse primer that hybridizes to the region (12).

Specific examples of the sets (A) to (O) described above include the following sets. The alphabets correspond to the (A) to (O), respectively. For example, the following (A-1) to (A-10) are examples of the set (A).

(A-1) A set of a forward primer containing in its 3'-side a sequence having not less than 15 consecutive bases, preferably not less than 18 consecutive bases in the base sequence of SEQ ID NO:26, more preferably the full-length sequence of the base sequence, or a sequence which is the same as the base sequence of SEQ ID NO:26 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F286A and LMO0084-R757A in the Examples described below.

(A-2) A set of a forward primer containing in its 3'-side a sequence having not less than 15 consecutive bases, preferably not less than 18 consecutive bases in the base sequence of SEQ ID NO:26, more preferably the full-length sequence of the base sequence, or a sequence which is the same as the base sequence of SEQ ID NO:26 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F286A and LMO0084-R757B in the Examples described below.

(A-3) A set of a forward primer containing in its 3'-side a sequence having not less than 15 consecutive bases, preferably not less than 18 consecutive bases in the base sequence of SEQ ID NO:27, more preferably the full-length sequence of the base sequence, or a sequence which is the same as the base sequence of SEQ ID NO:27 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F286B and LMO0084-R757A in the Examples described below.

(A-4) A set of a forward primer containing in its 3'-side a sequence having not less than 15 consecutive bases, preferably not less than 18 consecutive bases in the base sequence of SEQ ID NO:27, more preferably the full-length sequence of the base sequence, or a sequence which is the same as the base sequence of SEQ ID NO:27 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F286B and LMO0084-R757B in the Examples described below.

(A-5) A set of a forward primer containing in its 3'-side a sequence having not less than 15 consecutive bases, preferably not less than 18 consecutive bases in the base sequence of SEQ ID NO:28, more preferably the full-length sequence of the base sequence, or a sequence which is the same as the base sequence of SEQ ID NO:28 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F281A and LMO0084-R757A in the Examples described below.

(A-6) A set of a forward primer containing in its 3'-side a sequence having not less than 15 consecutive bases, preferably not less than 18 consecutive bases in the base sequence of SEQ ID NO:28, more preferably the full-length sequence of the base sequence, or a sequence which is the same as the base sequence of SEQ ID NO:28 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F281 A and LMO0084-875713 in the Examples described below.

(A-7) A set of a forward primer containing in its 3'-side a sequence having not less than 15 consecutive bases, preferably not less than 18 consecutive bases in the base sequence of SEQ ID NO:29, more preferably the full-length sequence of the base sequence, or a sequence which is the same as the base sequence of SEQ ID NO:29 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F281B and LMO0084-R757A in the Examples described below.

(A-8) A set of a forward primer containing in its 3'-side a sequence having not less than 15 consecutive bases, preferably not less than 18 consecutive bases in the base sequence of SEQ ID NO:29, more preferably the full-length sequence of the base sequence, or a sequence which is the same as the base sequence of SEQ ID NO:29 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F281B and LMO0084-R757B in the Examples described below.

(A-9) A set of a mixed forward primer containing in its 3'-side a sequence having not less than 15 consecutive bases, preferably not less than 18 consecutive bases in the base sequence of SEQ ID NO:67, more preferably the full-length sequence of the base sequence, and a mixed reverse primer containing in its 3'-side a sequence having not less than 15 consecutive bases, preferably not less than 18 consecutive bases in the base sequence of SEQ ID NO:69, more preferably the full-length sequence of the base sequence. Specific examples of this set include the set of LMO0084-F286/M and LMO0084-R757M in the Examples described below.

(A-10) A set of a mixed forward primer containing in its 3'-side a sequence having not less than 15 consecutive bases, preferably not less than 18 consecutive bases in the base sequence of SEQ ID NO:68, more preferably the full-length sequence of the base sequence, and a mixed reverse primer containing in its 3'-side a sequence having not less than 15 consecutive bases, preferably not less than 18 consecutive bases in the base sequence of SEQ ID NO:69, more preferably the full-length sequence of the base sequence. Specific examples of this set include the set of LMO0084-F281/M and LMO0084-R7571M in the Examples described below.

(B-1) A set of a forward primer containing in its 3'-side a sequence having not less than 15 consecutive bases, preferably not less than 18 consecutive bases in the base sequence of SEQ ID NO:58, more preferably the full-length sequence of the base sequence, or a sequence which is the same as the base sequence of SEQ ID NO:58 except that not mote than 4 bases are substituted at a genetic polymorphism site(s) therein, and a reverse primer containing in its 3'-side a sequence having not less than 15 consecutive bases in the base sequence of SEQ ID NO:59, preferably the full-length sequence of the base sequence, or a sequence which is the same as the base sequence of SEQ ID NO:59 except that not more than 4 bases are substituted at a genetic polymorphism site(s) therein. Specific examples of this set include the set of the LAMP primers LMO84 FIP and LMO84 BIP in the Examples described below.

(C-1) A set of a forward primer containing in its 3'-side a sequence having not less than 15 consecutive bases, preferably not less than 18 consecutive bases in the base sequence of SEQ ID NO:32, more preferably the full-length sequence of the base sequence, or a sequence which is the same as the base sequence of SEQ ID NO:32 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:37, more preferably the full-length sequence of the base sequence, or a sequence which is the same as the base sequence of SEQ ID NO:37 except that not more than 4 bases are substituted at a genetic polymorphism site(s) therein. Specific examples of this set include the set of LMO2736-F8 and LMO2736-R 176 in the Examples described below.

(D-1) A set of a forward primer containing in its 3'-side a sequence having not less than 15 consecutive bases, preferably not less than 18 consecutive bases in the base sequence of SEQ ID NO:33, more preferably the full-length sequence of the base sequence, or a sequence which is the same as the base sequence of SEQ ID NO:33 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:38, more preferably the full-length sequence of the base sequence, or a sequence which is the same as the base sequence of SEQ ID NO:38 except that not more than 4 bases are substituted at a genetic polymorphism site(s) therein. Specific examples of this set include the set of LMO2736-F222 and LMO2736-R591 in the Examples described below.

(D-2) A set of a mixed forward primer containing in its 3'-side a sequence having not less than 15 consecutive bases, preferably not less than 18 consecutive bases in the base sequence of SEQ ID NO:70, more preferably the full-length sequence of the base sequence, and a mixed reverse primer containing in its 3'-side a sequence having not less than 15 consecutive bases, preferably not less than 18 consecutive bases in the base sequence of SEQ ID NO:74, more preferably the full-length sequence of the base sequence. Specific examples of this set include the set of LMO2736-F2221M and LMO2736-R591/M in the Examples described below.

(E-1) A set of a forward primer containing in its 3'-side a sequence having not less than 15 consecutive bases, preferably not less than 18 consecutive bases in the base sequence of SEQ ID NO:34, more preferably the full-length sequence of the base sequence, or a sequence which is the same as the base sequence of SEQ ID NO:34 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:38, more preferably the full-length sequence of the base sequence, or a sequence which is the same as the base sequence of SEQ ID NO:38 except that not more than 4 bases are substituted at a genetic polymorphism site(s) therein. Specific examples of this set include the set of LMO2736-F488 and LMO2736-R591 in the Examples described below.

(E-2) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a mixed reverse primer containing in its 3'-side a sequence having not less than 15 consecutive bases, preferably not less than 18 consecutive bases in the base sequence of SEQ ID NO:74, more preferably the full-length sequence of the base sequence. Specific examples of this set include the set of LMO2736-F488/M and LMO2736-R591/M in the Examples described below.

(F-1) A set of a forward primer containing in its 3'-side a sequence having not less than 15 consecutive bases, preferably not less than 18 consecutive bases in the base sequence of SEQ ID NO:34, more preferably the full-length sequence of the base sequence, or a sequence which is the same as the base sequence of SEQ ID NO:34 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:39, more preferably the full-length sequence of the base sequence, or a sequence which is the same as the base sequence of SEQ ID NO:39 except that not more than 4 bases are substituted at a genetic polymorphism site(s) therein. Specific examples of this set include the set of LMO2736-F488 and LMO2736-R685 in the Examples described below.

(F-2) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a mixed reverse primer containing in its 3'-side a sequence having not less than 15 consecutive bases, preferably not less than 18 consecutive bases in the base sequence of SEQ ID NO:75, more preferably the full-length sequence of the base sequence. Specific examples of this set include the set of LMO2736-F4881M and LMO2736-R6851M in the Examples described below.

(G-1) A set of a forward primer containing in its 3'-side a sequence having not less than 15 consecutive bases, preferably not less than 18 consecutive bases in the base sequence of SEQ ID NO:34, more preferably the full-length sequence of the base sequence, or a sequence which is the same as the base sequence of SEQ ID NO:34 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:40, more preferably the full-length sequence of the base sequence, or a sequence which is the same as the base sequence of SEQ ID NO:40 except that not more than 4 bases are substituted at a genetic polymorphism site(s) therein. Specific examples of this set include the set of LMO2736-F488 and LMO2736-8771 in the Examples described below.

(G-2) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a mixed reverse primer containing in its 3'-side a sequence having not less than 15 consecutive bases, preferably not less than 18 consecutive bases in the base sequence of SEQ ID NO:76, more preferably the full-length sequence of the base sequence. Specific examples of this set include the set of LMO2736-F4881M and LMO2736-R771/M in the Examples described below.

(H-1) A set of a forward primer containing in its 3'-side a sequence having not less than 15 consecutive bases, preferably not less than 18 consecutive bases in the base sequence of SEQ ID NO:35, more preferably the full-length sequence of the base sequence, or a sequence which is the same as the base sequence of SEQ ID NO:35 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:39, more preferably the full-length sequence of the base sequence, or a sequence which is the same as the base sequence of SEQ ID NO:39 except that not more than 4 bases are substituted at a genetic polymorphism site(s) therein. Specific examples of this set include the set of LMO2736-F530 and LMO2736-R685 in the Examples described below.

(H-2) A set of a mixed forward primer containing in its 3'-side a sequence having not less than 15 consecutive bases, preferably not less than 18 consecutive bases in the base sequence of SEQ ID NO:72, more preferably the full-length sequence of the base sequence, and a mixed reverse primer containing in its 3'-side a sequence having not less than 15 consecutive bases, preferably not less than 18 consecutive bases in the base sequence of SEQ ID NO:75, more preferably the full-length sequence of the base sequence. Specific examples of this set include the set of LMO2736-F530/M and LMO2736-R6851M in the Examples described below.

(I-1) A set of a forward primer containing in its 3'-side a sequence having not less than 15 consecutive bases, preferably not less than 18 consecutive bases in the base sequence of SEQ ID NO:35, more preferably the full-length sequence of the base sequence, or a sequence which is the same as the base sequence of SEQ ID NO:35 except that not mote than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:40, more preferably the full-length sequence of the base sequence, or a sequence which is the same as the base sequence of SEQ ID NO:40 except that not more than 4 bases are substituted at a genetic polymorphism site(s) therein. Specific examples of this set include the set of LMO2736-F530 and LMO2736-R771 in the Examples described below.

(I-2) A set of a forward primer containing in its 3'-side a sequence having not less than 15 consecutive bases, preferably not less than 18 consecutive bases in the base sequence of SEQ ID NO:60, more preferably the full-length sequence of the base sequence, or a sequence which is the same as the base sequence of SEQ ID NO:60 except that not more than 4 bases are substituted at a genetic polymorphism site(s) therein, and a reverse primer containing in its 3'-side a sequence having not less than 15 consecutive bases in the base sequence of SEQ ID NO:61, preferably the full-length sequence of the base sequence, or a sequence which is the same as the base sequence of SEQ ID NO:61 except that not more than 4 bases are substituted at a genetic polymorphism site(s) therein. Specific examples of this set include the set of the LAMP primers LMO2736-1 F IP and LMO2736-1 BIP in the Examples described below.

(I-3) A set of a forward primer containing in its 3'-side a sequence having not less than 15 consecutive bases, preferably not less than 18 consecutive bases in the base sequence of SEQ ID NO:62, more preferably the full-length sequence of the base sequence, or a sequence which is the same as the base sequence of SEQ ID NO:62 except that not more than 4 bases are substituted at a genetic polymorphism site(s) therein, and a reverse primer containing in its 3'-side a sequence having not less than 15 consecutive bases in the base sequence of SEQ ID NO:61, preferably the full-length sequence of the base sequence, or a sequence which is the same as the base sequence of SEQ ID NO:61 except that not more than 4 bases are substituted at a genetic polymorphism site(s) therein. Specific examples of this set include the set of the LAMP primers LMO2736-2 FIP and LMO2736-2 BIP in the Examples described below.

(I-4) A set of a mixed forward primer containing in its 3'-side a sequence having not less than 15 consecutive bases, preferably not less than 18 consecutive bases in the base sequence of SEQ ID NO:72, more preferably the full-length sequence of the base sequence, and a mixed reverse primer containing in its 3'-side a sequence having not less than 15 consecutive bases, preferably not less than 18 consecutive bases in the base sequence of SEQ ID NO:76, more preferably the full-length sequence of the base sequence. Specific examples of this set include the set of LMO2736-F530/M and LMO2736-R771/M in the Examples described below.

(J-1) A set of a forward primer containing in its 3'-side a sequence having not less than 15 consecutive bases, preferably not less than 18 consecutive bases in the base sequence of SEQ ID NO:35, more preferably the full-length sequence of the base sequence, or a sequence which is the same as the base sequence of SEQ ID NO:35 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F530 and LMO2736-R992 in the Examples described below.

(J-2) A set of a mixed forward primer containing in its 3'-side a sequence having not less than 15 consecutive bases, preferably not less than 18 consecutive bases in the base sequence of SEQ ID NO:72, more preferably the full-length sequence of the base sequence, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F530/M and LMO2736-R992 in the Examples described below.

(K-1) A set of a forward primer containing in its 3'-side a sequence having not less than 15 consecutive bases, preferably not less than 18 consecutive bases in the base sequence of SEQ ID NO:36, more preferably the full-length sequence of the base sequence, or a sequence which is the same as the base sequence of SEQ ID NO:36 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:39, more preferably the full-length sequence of the base sequence, or a sequence which is the same as the base sequence of SEQ ID NO:39 except that not more than 4 bases are substituted at a genetic polymorphism site(s) therein. Specific examples of this set include the set of LMO2736-F572 and LMO2736-R685 in the Examples described below.

(K-2) A set of a mixed forward primer containing in its 3'-side a sequence having not less than 15 consecutive bases, preferably not less than 18 consecutive bases in the base sequence of SEQ ID NO:73, more preferably the full-length sequence of the base sequence, and a mixed reverse primer containing in its 3'-side a sequence having not less than 15 consecutive bases, preferably not less than 18 consecutive bases in the base sequence of SEQ ID NO:75, more preferably the full-length sequence of the base sequence. Specific examples of this set include the set of LMO2736-F5721M and LMO2736-R685/M in the Examples described below.

(L-1) A set of a forward primer containing in its 3'-side a sequence having not less than 15 consecutive bases, preferably not less than 18 consecutive bases in the base sequence of SEQ ID NO:36, more preferably the full-length sequence of the base sequence, or a sequence which is the same as the base sequence of SEQ ID NO:36 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:40, more preferably the full-length sequence of the base sequence, or a sequence which is the same as the base sequence of SEQ ID NO:40 except that not more than 4 bases are substituted at a genetic polymorphism site(s) therein. Specific examples of this set include the set of LMO2736-F572 and LMO2736-R771 in the Examples described below.

(L-2) A set of a mixed forward primer containing in its 3'-side a sequence having not less than 15 consecutive bases, preferably not less than 18 consecutive bases in the base sequence of SEQ ID NO:73, more preferably the full-length sequence of the base sequence, and a mixed reverse primer containing in its 3'-side a sequence having not less than 15 consecutive bases, preferably not less than 18 consecutive bases in the base sequence of SEQ ID NO:76, more preferably the full-length sequence of the base sequence. Specific examples of this set include the set of LMO2736-F572/M and LMO2736-R771/M in the Examples described below.

(M-1) A set of a forward primer containing in its 3'-side a sequence having not less than 15 consecutive bases, preferably not less than 18 consecutive bases, more preferably not less than 20 consecutive bases in the base sequence of SEQ ID NO:63, still more preferably the full-length sequence of the base sequence, or a sequence which is the same as the base sequence of SEQ ID NO:63 except that not more than 4 bases are substituted at a genetic polymorphism site(s) therein, and a reverse primer containing in its 3'-side the base sequence of SEQ ID NO:64 or a sequence which is the same as the base sequence of SEQ ID NO:64 except that not more than 4 bases are substituted at a genetic polymorphism site(s) therein. Specific examples of this set include the set of the LAMP primers LMO2736-10 FIP and LMO2736-10 BIP in the Examples described below.

(N-1) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F488/M and LMO2736-R992 in the Examples described below.

(O-1) A set of a mixed forward primer containing in its 3'-side a sequence having not less than 15 consecutive bases, preferably not less than 18 consecutive bases in the base sequence of SEQ ID NO:73, more preferably the full-length sequence of the base sequence, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F572/M and LMO2736-R992 in the Examples described below.

A primer containing a particular sequence in its 3'-side includes a primer in which an arbitrary sequence is added to the 5'-side of the particular sequence, and a primer composed of the particular sequence. For example, a primer containing the base sequence of SEQ ID NO:26 in its 3'-side includes a primer in which an arbitrary sequence is added to the 5'-side of the base sequence of SEQ ID NO:26, and a primer composed of the base sequence of SEQ ID NO:26.

Preferred specific examples of the genetic polymorphism sites in the base sequences described in (A-1) to (O-1) are as follows. Preferred specific examples of the primers containing a base substitution include primers each containing in its 3'-side a sequence in which at least one base selected from the following specific examples of genetic polymorphism sites is substituted. These specific examples are genetic polymorphism sites specified based on an alignment of the 12 kinds of lmo0084 gene sequences of 12 serotypes of SEQ ID NOs: 1 to 12, and an alignment of the 13 kinds of lmo2736 gene sequences of 12 serotypes of SEQ ID NOs:13 to 25. It should noted, however, that genetic polymorphism sites other than the following specific examples may be found in cases where gene sequences of *monocytogenes* bacterial strains of other serotypes or other *monocytogenes* bacterial strains of the same serotypes are further taken into account, and that base substitutions in such sites are acceptable in the present invention. Thus, the genetic polymorphism sites in the sequences in the present invention are not limited to the following specific examples.

SEQ ID NO:26: position 6, position 15, and position 16
SEQ ID NO:27: position 6, position 15, and position 16
SEQ ID NO:28: position 2, position 11, and position 20
SEQ ID NO:29: position 2, position 11, and position 20
SEQ ID NO:30: position 8 and position 11
SEQ ID NO:31: position 8 and position 11
SEQ ID NO:33: position 5, position 18, and position 20
SEQ ID NO:34: position 5 and position 8
SEQ ID NO:35: position 5 and position 11
SEQ ID NO:36: position 5 and position 11
SEQ ID NO:38: position 10 and position 16
SEQ ID NO:39: position 14, position 15, and position 16
SEQ ID NO:40: position 7
SEQ ID NO:58: position 5, position 9, position 11, and position 14
SEQ ID NO:59: position 1 and position 10
SEQ ID NO:60: position 7 and position 13
SEQ ID NO:61: position 5
SEQ ID NO:62: position 7 and position 13
SEQ ID NO:63: position 1, position 4, position 19, and position 25
SEQ ID NO:64: position 6 and position 15

Preferred specific examples of the arbitrary additional sequence that may be present in the 5'-side of the primer include an additional sequence for construction of a LAMP primer. By selecting an arbitrary partial region positioned in the inner side relative to the target region of the primer, and adding the complementary strand of the partial region to the 5'-side of the primer, a LAMP primer can be constructed. Software for designing LAMP primers is known, and such known software can be used for designing LAMP primers for specific detection of the *monocytogenes* bacterium based on the specific primer setting regions (1) to (14) described above.

In the designing of a LAMP primer, the regions F3, F2, F1, B1, B2, and B3, located in this order from the 5'-upstream side, are necessary. A LAMP primer set is constituted with an FIP primer, in which the complementary sequence (the sequence of the antisense strand) of the F1 sequence is added to the 5'-end of F2; a BIP primer, in which the complementary sequence (the sequence of the sense strand) of the B1 sequence is added to the 5'-end of B2; a forward primer that hybridizes to the F3 region, and a reverse primer that hybridises to the B3 region. The specific primer setting regions (1) to (14) described above may be employed for at least one of F2 and B2 among these, preferably for both of these. When the design is based on the primer sets of (a) to (v), in cases where the amplification size of the set is about 200 to 300 bp, both F2 and B2 may be selected such that they overlap with the primer setting regions. In cases where the amplification size of the set is outside this range, one of F2 and B2 may be selected such that it overlaps with the primer setting regions, and the other may be appropriately selected from candidate sequences proposed by the software.

The following (i) to (iv) are LAMP primer sets each of which was designed based on the set of LMO0084-F286A and LMO0084-R757B, which is one example of the primer set of (A-2), and the set of LMO2736-F530 and LMO2736-R771, which is one example of the primer set of (1-1). Preferred specific examples of the LAMP primer set for detection of the *monocytogenes* bacterium include these sets.

(i) A set of an F3 primer composed of the base sequence of SEQ ID NO:42, a B3 primer composed of the base sequence of SEQ ID NO:43, an FIP primer composed of the base sequence of SEQ ID NO:44, and a BIP primer composed of the base sequence of SEQ ID NO:45.

(ii) A set of an F3 primer composed of the base sequence of SEQ ID NO:46, a B3 primer composed of the base sequence of SEQ ID NO:47, an FIP primer composed of the base sequence of SEQ ID NO:48, and a BIP primer composed of the base sequence of SEQ ID NO:49.

(iii) A set of an F3 primer composed of the base sequence of SEQ ID NO:50, a B3 primer composed of the base sequence of SEQ ID NO:51, an FIP primer composed of the base sequence of SEQ ID NO:52, and a BIP primer composed of the base sequence of SEQ ID NO:53.

(iv) A set of an F3 primer composed of the base sequence of SEQ ID NO:54, a B3 primer composed of the base sequence of SEQ ID NO:55, an FIP primer composed of the base sequence of SEQ ID NO:56, and a BIP primer composed of the base sequence of SEQ ID NO:57.

Isothermal amplification primers used of methods other than the LAMP method may also be designed using known software or the like based on the specific primer setting regions (1) to (14) described above.

Preferred specific examples of the probe for detection of the PCR amplification product include probes containing oligonucleotide portions having the following sequences. The probe containing an oligonucleotide portion having the sequence of SEQ ID NO:85 is a mixed probe of a probe containing an oligonucleotide portion in which n- - -n is T- - -A (SEQ ID NO:78), and a probe containing an oligonucleotide portion in which n- - -n is C- - -C (SEQ ID NO:79). Similarly, the probe containing an oligonucleotide portion having the sequence of SEQ ID NO:86 is a mixed probe of a probe containing an oligonucleotide portion in which n- - -n is G- - -G (SEQ ID NO:83), and a probe containing an oligonucleotide portion in which n- - -n is C- - -C (SEQ ID NO:84).

```
<Probes for LMO0084 Gene>
                                        (SEQ ID NO: 77)
TATTACATTCATAGAATTGACCC (set at position 366 to
position 389)

(SEQ ID NO: 85)
ATCTGGTGGCGAGAAGCnGAAnA (set at position 535 to
position 558; nGAAn is TGAAA or CGAAC)

(SEQ ID NO: 80)
TACCAAGATTCCAAAAAGAAGCCATG (set at position 686 to
position 711)
```

-continued

<Probes for LMO2736 Gene>

(SEQ ID NO: 81)
AAAAAAGGCTGGACTAAAGC (set at position 70 to position 89)

(SEQ ID NO: 82)
ACGTCAAAAAAATCATTATC (set at position 372 to position 393)

(SEQ ID NO: 86)
GTTTTCGGTGCTCAAAAAGGnGCAAnTCC (set at position 619 to position 647; nGCAAn is GGCAAG or CGCAAC)

Each of the probe of SEQ ID NO:85 and the probe of SEQ ID NO:86 is a mixed probe of two kinds of oligonucleotide probes. The mixing ratio of these two kinds of probes, in terms of the molar ratio, may be about 1:5 to 5:1, for example, about 1:2 to 2:1, or about 1:1.5 to 1.5:1. The probes can be preferably used at a mixing ratio of 1:1.

Since the position where each probe is set is as described above, the probe may be used in combination with a primer set which amplifies a region containing this set region. A probe containing an oligonucleotide portion having these sequences can be preferably used as a capture probe for nucleic acid chromatography or a probe for real-time PCR. In cases where the probe is used as a real-time PCR probe, the 5'-end and the 3'-end of the oligonucleotide may be modified with a fluorescent substance and a quencher substance. It is common to modify the 5'-end with a fluorescent substance, and the 3'-end with a quencher substance. Especially preferred combinations of the primers and the probe are described in Table 23 and Table 25 in the following Examples.

EXAMPLES

The present invention is described below more concretely by way of Examples. However, the present invention is not limited to the following Examples.

1. Search for Target Genes

Conventional products for gene testing of the *monocytogenes* bacterium target pathogenicity genes of the *monocytogenes* bacterium, such as the hlyA gene, clpC gene, inlA gene, and plcA gene. However, they are not capable of distinguishing the *monocytogenes* bacterium from other bacteria belonging to the genus *Listeria*. Aiming at establishment of a primer set capable of distinguishing the *monocytogenes* bacterium from other bacteria belonging to the genus *Listeria* with high accuracy, a study was carried out using genes other than the pathogenicity genes described above as targets.

First, the site of http://genolist.pasteur.fr/ListiList/ was used. The information on *monocytogenes* in Accession No. NC_003210.1 and *innocua* in Accession No. NC_003212.1 on this site was utilized. *Listeria innocua* (number of genes: 3068) and *Listeria monocytogenes* (number of genes: 2941), which belong to the genus *Listeria*, were subjected to comparative genomic analysis to narrow down *monocytogenes*-specific genes to 296 genes.

Subsequently, for each of the selected 296 genes, BLAST search was carried out against a database to investigate whether or not the gene can be confirmed to be present in the genome sequences of all isolated strains of *monocytogenes* of each serotype deposited therein. Genes whose presence could not be confirmed in any of the isolated strains were excluded from the candidates. Examples of the search results are shown in Table 3.

TABLE 3

| Serotype | LMO00038 | LMO00077 | LMO00313 | LMO02387 | LMO02736 |
|---|---|---|---|---|---|
| L.monocytogenes 1/2a | 18 | 18 | 1 | 18 | 18 |
| L.monocytogenes 1/2b | 5 | 5 | 2 | 5 | 5 |
| L.monocytogenes 1/2c | 2 | 2 | 2 | 2 | 2 |
| L.monocytogenes 3a | 2 | 2 | 0 | 2 | 2 |
| L.monocytogenes 3b | 1 | 1 | 0 | 1 | 1 |
| L.monocytogenes 3c | 1 | 1 | 1 | 1 | 1 |
| L.monocytogenes 4a | 0 | 3 | 0 | 3 | 3 |
| L.monocytogenes 4b | 12 | 12 | 5 | 12 | 12 |
| L.monocytogenes 4c | 1 | 1 | 0 | 1 | 1 |
| L.monocytogenes 4d | 1 | 1 | 0 | 1 | 1 |
| L.monocytogenes 4e | 0 | 0 | 0 | 1 | 1 |
| L.monocytogenes 7 | 1 | 1 | 0 | 1 | 1 |
| | There is/are an isolated strain(s) for which the presence of the gene cannot be confirmed. ↓ Excluded from candidates | There is/are an isolated strain(s) for which the presence of the gene cannot be confirmed. ↓ Excluded from candidates | There is/are an isolated strain(s) for which the presence of the gene cannot be confirmed. ↓ Excluded from candidates | The presence of the gene could be confirmed in genomic sequences of all isolated strains deposited. ↓ Selected as a candidate | The presence of the gene could be confirmed in genomic sequences of all isolated strains deposited. ↓ Selected as a candidate |

By this, the candidate genes were finally narrowed down to 6 genes (LMO 0083, LMO 0084, LMO 0444, LMO 0833, LMO 2387, and LMO 2736).

For each of the 6 genes, a plurality of PCR primers were designed, and PCR was actually carried out for the 6 strains of the *monocytogenes* bacterium (serotypes 1/2a, 1/2b, 1/2c, 4a, 4b, and 4d) and 3 strains of other bacteria belonging to the genus *Listeria* (*L. innocua*, *L. grayi*, and *L. ivanovii*), to study specificity to the *monocytogenes* bacterium. Based on comparison among sequences of various serotypes of *monocytogenes* (using the sequences of the accession numbers described above in Table 2), the PCR primers in this study were designed such that they target common regions. As a result, with LMO 0083, LMO 0444, LMO 0833, and MLO 2387, detection of some of the 6 strains was unsuccessful, or amplification occurred with other bacteria belonging to the genus *Listeria*. Thus, design of a primer set having high specificity was difficult therewith. For example, in the case of the LMO0833 gene, specificity was obtained since no amplification of the bacteria belonging to the genus *Listeria* was found as a result of combination of the primer F329 (ggaaagcaattgtccactcga; SEQ ID NO:65) and the primer R610 (tgttggtgagtagcgtggaa; SEQ ID NO:66). However, *monocytogenes* of the serotype 4a also did not show the amplification. Table 4 shows examples of the PCR results for the candidate genes. With LMO 0084 and LMO 2736, specific amplification products were obtained only from the 6 strains of the *monocytogenes* bacterium. For comparison, two commercially available kits for gene testing of the *monocytogenes* bacterium were used for detection of the same bacterial strains. As a result, neither of these succeeded in specific detection of the *monocytogenes* bacteria used herein (Table 4). From these results, the candidate genes were narrowed down to LMO 0084 and LMO 2736, and construction of *monocytogenes* bacterium-specific primers was attempted therewith.

II. Construction of *Monocytogenes* Bacterium-Specific Primer Sets

Base sequences of the two genes LMO 0084 and LMO 2736 in various serotypes, identified by the narrowing down as described above, were studied in more detail, and a large number of primers were designed therefrom. By performing a PCR study using an increased number of bacterial strains, construction of primers for specific detection of the *monocytogenes* bacterium with high accuracy was attempted.

<Methods>

1. Bacterial Strains Used

The bacterial strains subjected to the PCR test (Table 5-1 to Table 5-3) were obtained from Microbe Division, RIKEN BioResource Research Center (JCM); Center for Conservation of Microbial Genetic Resource, Organization for Research and Community Development, Gifu University (GTC); Department of Biotechnology, National Institute of Technology and Evaluation (IFO); JA Zen-noh Institute of Animal Health (JA); and Institute of Applied Microbiology. University of Tokyo (IMCB).

TABLE 4

| Genename | Description | *L. monocytogenes* GTC02947 1/2a | *L. monocytogenes* GTC02948 1/2b | *L. monocytogenes* JCM7672 1/2c | *L. monocytogenes* JCM7674 4a | *L. monocytogenes* JCM7675 4b |
|---|---|---|---|---|---|---|
| LMO 0083 | similar to transcription regulator | − | + | + | + | + |
| LMO 0084 | similar to oxidoreductases | + | + | + | + | + |
| LMO 0444 | conserved hypothetical protein | + | + | + | − | − |
| LMO 0833 | similar to transcription regulator | + | + | + | − | + |
| LMO 2387 | conserved hypothetical protein | + | + | + | + | + |
| LMO 2736 | conserved hypothetical protein | + | + | + | + | + |
| hlyA gene | Psthogenic Bacterial Multiplex PCR Detection kit TA10 (TAKARA:RR106A) | + | + | + | − | − |
| (Unknown) | mericon *L. monocytogenes* Kit (QIAGEN: 290023) | + | + | + | + | + |

| Genename | Description | *L. monocytogenes* JCM7680 4d | *L. gayi* GTC02964T | *L. innocua* GTC16426T | *L. ivanovii* JCM7681 |
|---|---|---|---|---|---|
| LMO 0083 | similar to transcription regulator | + | − | − | − |
| LMO 0084 | similar to oxidoreductases | + | − | − | − |
| LMO 0444 | conserved hypothetical protein | − | − | − | − |
| LMO 0833 | similar to transcription regulator | + | − | − | − |
| LMO 2387 | conserved hypothetical protein | + | + | − | + |
| LMO 2736 | conserved hypothetical protein | + | − | + | − |
| hlyA gene | Psthogenic Bacterial Multiplex PCR Detection kit TA10 (TAKARA:RR106A) | − | − | − | − |
| (Unknown) | mericon *L. monocytogenes* Kit (QIAGEN: 290023) | + | + | + | + |

TABLE 5-1

Monocytogenes bacterium

| Bacterial strain No. | Microorganism name | Resource name | Serotype |
|---|---|---|---|
| 1 | L. monocytogenes | GTC02947 | 1/2a |
| 2 | L. monocytogenes | GTC02948 | 1/2b |
| 3 | L. monocytogenes | JCM7672 | 1/2c |
| 4 | L. monocytogenes | JCM7673 | 3a |
| 5 | L. monocytogenes | JCM7677 | 3b |
| 6 | L. monocytogenes | JCM7678 | 3c |
| 7 | L. monocytogenes | JCM7674 | 4a |
| 8 | L. monocytogenes | JCM7675 | 4b |
| 9 | L. monocytogenes | JCM7680 | 4d |
| 10 | L. monocytogenes | GTC02957 | 5 |

TABLE 5-2

Bacteria belonging to the genus Listeria other than the monocytogenes bacterium.

| Bacterial strain No. | Microorganism name | Resource name |
|---|---|---|
| 11 | L. ivanovii | GTC02961 |
| 12 | L. ivanovii subsp. ivanovii | JCM7681 |
| 13 | L. ivanovii subsp. ivanovii | GTC01640T |
| 14 | L. ivanovii subsp. londoniensis | GTC01641 |
| 15 | L. innocua | GTC16426T |
| 16 | L. innocua | GTC02960 |
| 17 | L. welshimeri | GTC02963T |
| 18 | L. seeligeri | GTC16428T |
| 19 | L. grayi | GTC02964T |
| 20 | L. murrayi | GTC02964 |
| 21 | L. marthii | GTC16430T |
| 22 | L. rocourtiae | GTC16429T |

TABLE 5-3

Food-poisoning bacteria other than Listeria bacteria which tend to cause problems in the field of foods

| Bacterial strain No. | Microorganism name | Resource name | Serotype |
|---|---|---|---|
| 23 | Escherichia coli | ATCC10798 | |
| 24 | Salmonella subsp. enterica (I) | JA.107 | Type I |
| 25 | Salmonella subsp. salamae (II) | JA.125 | Type II |
| 26 | Salmonella subsp. arizonae (IIIa) | JA.76 | Type IIIa |
| 27 | Salmonella subsp. diarizinae (IIIb) | JA.129 | Type IIIb |
| 28 | Salmonella subsp. houtenae (IV) | JA.n-22 | Type IV |
| 29 | Salmonella bongori (V) | JA.94 | Type V |
| 30 | Salmonella subsp. enterica Typhimurium | ATCC43971 | |
| 31 | Staphylococcus aureus | ATCC6538P | |
| 32 | Staphylococcus aureus | ATCC25923 | |
| 33 | Staphylococcus aureus | ATCC29213 | |
| 34 | Staphylococcus aureus | JMC2197 | |
| 35 | Staphylococcus aureus | IMCB.IMA2 | |
| 36 | Staphylococcus cohnii | ATCC29974 | |
| 37 | Staphylococcus haemolyticus | ATCC29970 | |
| 38 | Staphylococcus hyicus subsp. | ATCC11249 | |
| 39 | Staphylococcus intermedius | ATCC29663 | |
| 40 | Staphylococcus saprophyticus | ATCC15305 | |
| 41 | Citrobacter freundii | ATCC8090 | |
| 42 | Citrobacter freundii | ATCC8043 | |
| 43 | Proteus vulgaris | IFO3988 | |
| 44 | Lactobacillus bulgaricus | IFO13953 | |
| 45 | Lactobacillus helveticus | IFO3809 | |
| 46 | Streptococcus sp. | IFO3535 | |
| 47 | Streptococcus sanguis | ATCC10558 | |
| 48 | Streptococcus mitis | ATCC6249 | |

2. Primers and PCR Reaction Conditions

Various primers were designed based on sequence information for the lmo0084 gene (SEQ ID NOs: 1 to 12) and the lmo2736 gene (SEQ ID NOs:13 to 25) in various serotypes of Listeria monocytogenes. Table 6 shows part of those sequences. For the lmo0084 gene, primers of SEQ ID NOs:26, 28, and 30 were designed such that they reflect genetic polymorphism in the serotype 1/2a of the monocytogenes bacterium, and primers of SEQ ID NOs:27, 29, and 31 were designed such that they reflect genetic polymorphism in the serotype 4a. For the lmo2736 gene, primers of SEQ ID NOs:32, 37, and 41 were designed such that they reflect common sequences among the various serotypes of the monocytogenes bacterium, and primers of SEQ ID NOs:33, 34, 35, 36, 38, 39, and 40 were designed such that they reflect genetic polymorphism in the serotype 112c of the monocytogenes bacterium. The designed PCR primers were synthesized by custom synthesis by Fasmac Co., Ltd. Template DNA was obtained by extracting genomic DNA from each bacterial strain using a mericon DNA Bacteria Plus Kit (QIAGEN).

TABLE 6

| Target gene | Oligonucleotide name [a] | Sequence [b] | Setting position [c] | SEQ ID NO. |
|---|---|---|---|---|
| lmo0084 | LM00084-F286A | AGCCGTCGAGAAAGCATCAA<br>-----*--------**---- | 286 to 305 | 26 |
| | LM00084-F286B | AGCCGCCCAGAAAGTCTCAA<br>-----*--------**---- | 286 to 305 | 27 |
| | LM00084-F281A | TCGATAGCCGTCCAGAAAGC<br>-*--------*--------* | 281 to 300 | 28 |
| | LM00084-F281B | TTGATAGCCGCCCAGAAAGT<br>-*--------*--------* | 281 to 300 | 29 |
| | LM00084-R757A | GCTCGTCGGCGATTTCTTTC<br>-------*--*--------- | 738 to 757 | 30 |
| | LM00084-R757B | GCTCGTCGGCTATTTCTTTC<br>-------*--*--------- | 738 to 757 | 31 |

TABLE 6-continued

| Target gene | Oligonucleotide name [a] | Sequence [b] | Setting position [c] | SEQ ID NO. |
|---|---|---|---|---|
| lmo2736 | LMO2736-F8 | TCGTCATCGCACCTGATTCA<br>-------------------- | 8 to 27 | 32 |
| | LMO2736-F222 | GGCCTCCTACGGTATTCACG<br>----------------*-* | 222 to 241 | 33 |
| | LMO2736-F488 | CCGGTGGCATTCATTTGCAA<br>----*--*------------ | 488 to 507 | 34 |
| | LMO2736-F530 | GCAACCTTAACCCAAAGCTG<br>----*-----*--------- | 530 to 548 | 35 |
| | LMO2736-F572 | CCTGTGACGTSACGAATCCA<br>----*-----*--------- | 572 to 591 | 36 |
| | LMO2736-R176 | TCCACCTCGGAAGACTCACT<br>-------------------- | 157 to 176 | 37 |
| | LMO2736-R591 | TGGATTCGTCACGTCACAGG<br>---------*-----*---- | 572 to 591 | 38 |
| | LMO2736-R685 | AGTTCTGCATGGCGTTCTCT<br>-------------***---- | 666 to 685 | 39 |
| | LMO2736-R771 | TAGTCCAGCAGCGATACCAC<br>------*------------- | 752 to 771 | 40 |
| | LMO2736-R992 | TTGTTTTCGAGTGCAAGGCT<br>-------------------- | 973 to 992 | 41 |

[a] In the oligonucleotide nunes, F represents "forward", and R represents "reverse".
[b] * represents a base showing polymorphism based on comparison among the sequences of SEQ ID NOs: 1 to 25.
[c] The setting position is described using as a standard SEQ ID NO: 1 in the cases of the points targeting lmo0084, and SEQ ID NO: 13 in the cams of the primers targeting lmo2736.

The composition of the PCR reaction liquid is shown below in Table 7. The PCR was carried out using GeneAmp PCR System 9700. The reaction cycle was as follows: 94° C. for 2 minutes→(94° C. for 20 seconds→60° C. for 20 seconds→72° C. for 40 seconds)×30 cycles→72° C. for 7 minutes→4° C.

TABLE 7

| Reagent | Manufacturer | Code.No. | Liquid volume (AL) |
|---|---|---|---|
| TaKaRa Ex Taq (5 U/μl) | TaKaRa | RR01AM | 0.2 |
| 10× Ex Taq Buffer (Mg$^{2+}$ free) | TaKaRa | RR01AM | 2.0 |
| MgCl$_2$ (25 mM) | TaKaRa | RR01AM | 1.6 |
| dNTP Mixture (2.5 mM each) | TaKaRa | RR01AM | 1.6 |
| 100 μM Primer F | Fasmac | — | 0.1 |
| 100 μM Primer R | Fasmac | — | 0.1 |
| D.W. | — | — | 12.4 |
| 1 ng/μL Template DNA | — | — | 2.0 |
| Per tube | | | 20.0 |

3. Selective Isolation Medium for *Monocytogenes*

Various bacteria belonging to the genus *Listeria* were plated on ALOA agar medium (Sysmex Corporation) or CHROMagar medium (Kanto Chemical Co., Inc.), and cultured at 37° C. for about 24 hours, followed by observation of colonies. The *monocytogenes* bacterium forms bluish-green colonies accompanied by milky-white halos on ALOA agar medium, and blue colonies accompanied by milky-white halos on CHROMagar medium.
<Results>

Figures 1, 2:
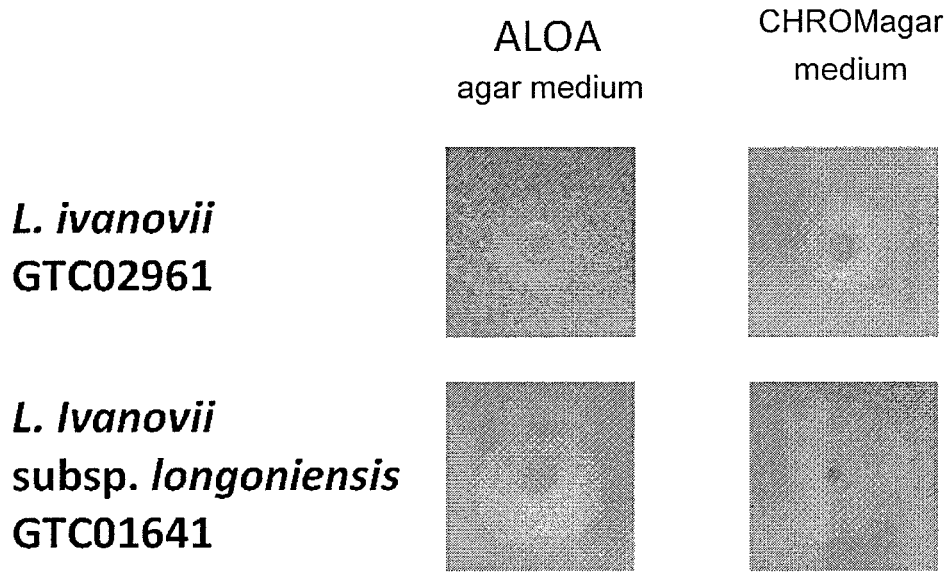
Figures 1, 2, 3:
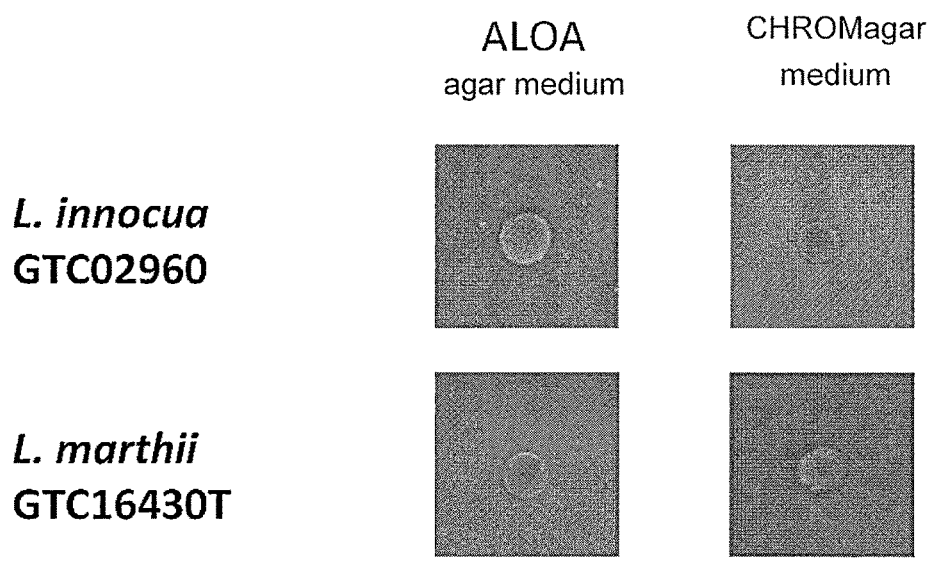
Figures 1, 2:
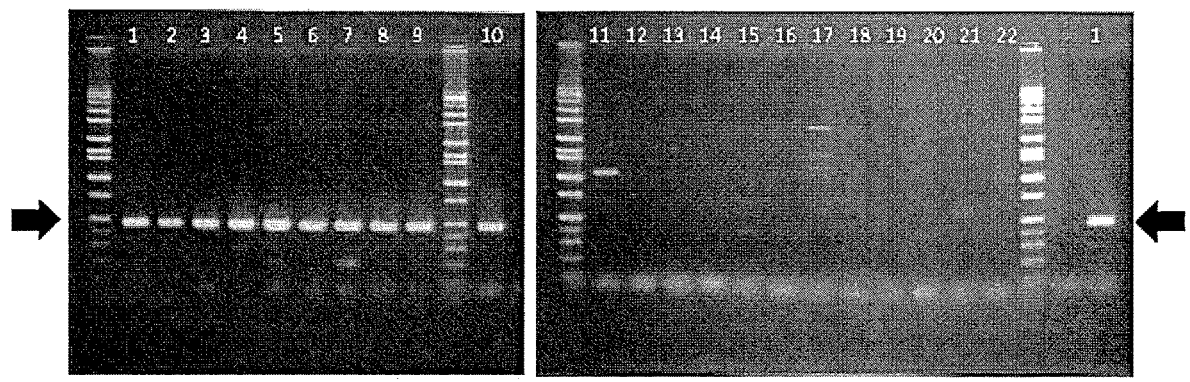
Figure 2:
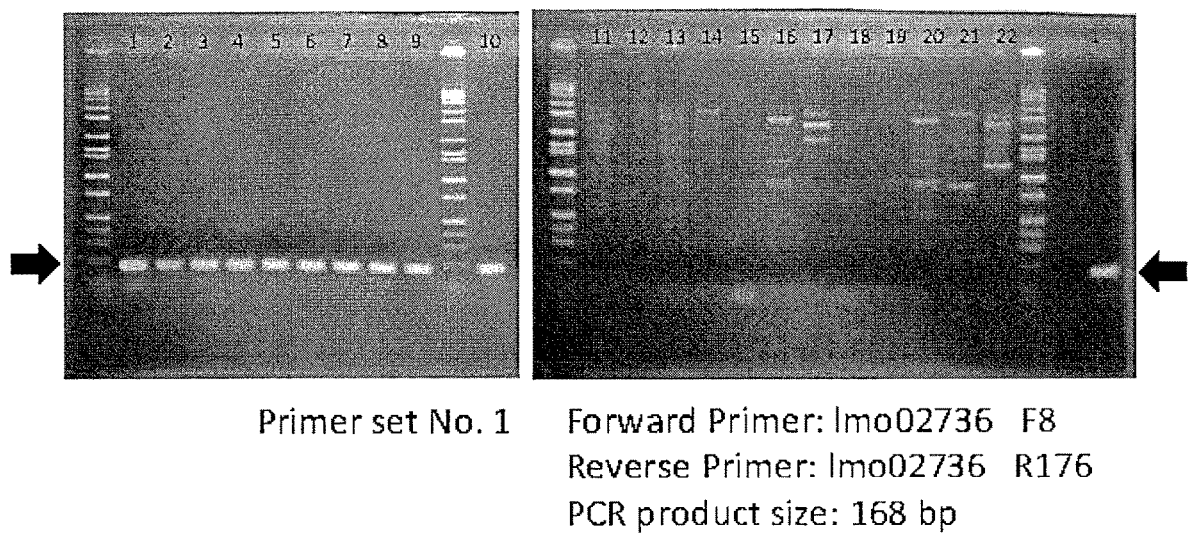

In the halo formation test, all strains of the *monocytogenes* bacterium showed formation of halos to give positive results although some strains such as the bacterial strain No. 4 partially showed colonies forming no halo. On the other hand, *L. ivanovii* (bacterial strain Nos. 11, 12, 13, and 14) and *L. seeligeri* (bacterial strain No. 18) showed false-positive results. No colony formation was found for 26 food-poisoning bacterial strains other than those of the genus *Listeria* (bacterial strain Nos. 23 to 48). Part of the results of the halo test are shown in FIG. 2-1 to FIG. 2-3.

As a result of study using various combinations of the designed primers, the *monocytogenes* bacterium could be specifically detected with the combinations shown in Table 8-1 to Table 8-4 independent of genetic polymorphism. None of these combinations produced a PCR product having the specific size from bacteria belonging to the genus *Listeria* other than the *monocytogenes* bacterium (bacterial strain Nos. 11 to 22), or from the other 26 food-poisoning bacterial strains (bacterial strain Nos. 23 to 48) (Table 9-1 to Table 9-6). Examples of the PCR results are shown in FIG. 2-1 and FIG. 2-2.

Since *L. ivanovii* and *L. seeligeri* form halos similarly to the *monocytogenes* bacterium on ALOA agar medium and CHROMagar medium, which are commonly used for selective isolation of the *monocytogenes* bacterium, they cannot be easily distinguished from the *monocytogenes* bacterium. However, with the primer sets shown in Table 8-1 to Table 8-4, various isolated bacterial strains of these bacteria belonging to the genus *Listeria* showed no amplification, giving negative results. On the other hand, the *monocytogenes* bacterial strain JMC7673 (bacterial strain No. 4 in the tables) could also be detected as the *monocytogenes* bacterium in spite of the fact that it also produces colonies forming no halo. Thus, it could be confirmed that the primer sets shown in Table 8-1 to Table 8-4 have very high specificities to the *monocytogenes* bacterium. It could be further confirmed that those primer sets are superior to the conventional *monocytogenes* bacterium detection PCR kits shown in Table 3.

TABLE 8-1

PCR for detection of the lmo0084 gene, and halo formation

| primer set. No | F primer | SEQ ID NO. | R primer | SEQ ID NO. | Amplification size (bp) | \multicolumn{10}{c}{Bacterial strain No. (*monocytogenes* bacterium)} | | | | | | | | | |
|---|---|---|---|---|---|---|---|---|---|---|---|---|---|---|---|
| | | | | | | 1 | 2 | 3 | 4 | 5 | 6 | 7 | 8 | 9 | 10 |
| 6 | F286A | 28 | R757A | 30 | 471 | + | + | + | + | + | + | + | + | + | + |
| 8 | F286A | 28 | R757B | 31 | 471 | + | + | + | + | + | + | + | + | + | + |
| 14 | F286B | 27 | R757A | 30 | 471 | + | + | + | + | + | + | + | + | + | + |
| 16 | F286B | 27 | 8757B | 31 | 471 | + | + | + | + | + | + | + | + | + | + |
| 2 | F281A | 28 | R757A | 30 | 476 | + | + | + | + | + | + | + | + | + | + |
| 4 | F281A | 28 | R757B | 31 | 476 | + | + | + | + | + | + | + | + | + | + |
| 10 | F281B | 28 | R757A | 30 | 476 | + | + | + | + | + | + | + | + | + | + |
| 12 | F281B | 29 | R757B | 31 | 476 | + | + | + | + | + | + | + | + | + | + |
| | Halo formation | | | | | (+) | (+) | (+) | (+/−) | (+) | (+) | (+) | (+) | (+) | (+) |

TABLE 8-2

PCR for detection of the lmo0084 gene, and halo formation

| primer set No. | F primer | R primer | Amplification size (bp) | \multicolumn{12}{c}{Bacterial strain No. (bacteria belonging ts the genus *Listeria* other than the *monocytogenes* bacterium)} | | | | | | | | | | | |
|---|---|---|---|---|---|---|---|---|---|---|---|---|---|---|---|---|
| | | | | 11 | 12 | 13 | 14 | 15 | 16 | 17 | 18 | 19 | 20 | 21 | 22 |
| 6 | F286A | R757A | 471 | − | − | − | − | − | − | − | − | − | − | − | − |
| 8 | F286A | R757B | 471 | − | − | − | − | − | − | − | − | − | − | − | − |
| 14 | F286B | R757A | 471 | − | − | − | − | − | − | − | − | − | − | − | − |
| 16 | F286B | 8757B | 471 | − | − | − | − | − | − | − | − | − | − | − | − |
| 2 | F281A | R757A | 476 | − | − | − | − | − | − | − | − | − | − | − | − |
| 4 | F281A | R757B | 476 | − | − | − | − | − | − | − | − | − | − | − | − |
| 10 | F281B | R757A | 476 | − | − | − | − | − | − | − | − | − | − | − | − |
| 12 | F281B | R757B | 476 | − | − | − | − | − | − | − | − | − | − | − | − |
| | Halo formation | | | (+) | (+) | (+) | (+) | (−) | (−) | (−) | (+) | (−) | (−) | (−) | (−) |

TABLE 8-3

PCR for detection of the lmo2736 gene, and halo fomation

| primer set. No | F primer | SEQ ID NO. | R primer | SEQ ID NO. | Amplification size (bp) | \multicolumn{10}{c}{Bacterial strain No. (*monocytogenes* bacterium)} | | | | | | | | | |
|---|---|---|---|---|---|---|---|---|---|---|---|---|---|---|---|
| | | | | | | 1 | 2 | 3 | 4 | 5 | 6 | 7 | 8 | 9 | 10 |
| 1 | F8 | 32 | R176 | 37 | 168 | + | + | + | + | + | + | + | + | + | + |
| 3 | F222 | 33 | R591 | 38 | 369 | + | + | + | + | + | + | + | + | + | |
| 4 | F488 | 34 | R591 | 38 | 103 | + | + | + | + | + | + | + | + | + | |
| 5 | F488 | 34 | R685 | 39 | 197 | + | + | + | + | + | + | + | + | + | |
| 6 | F488 | 34 | R771 | 40 | 283 | + | + | + | + | + | + | + | + | + | |
| 9 | F530 | 35 | R685 | 39 | 155 | + | + | + | + | + | + | + | + | + | |
| 10 | F530 | 35 | R771 | 40 | 241 | + | + | + | + | + | + | + | + | + | |
| 12 | F530 | 35 | R992 | 41 | 462 | + | + | + | + | + | + | + | + | + | |
| 13 | F572 | 36 | R685 | 39 | 113 | + | + | + | + | + | + | + | + | + | |
| 14 | F572 | 36 | R771 | 40 | 199 | + | + | + | + | + | + | + | + | + | |
| | Halo formation | | | | | (+) | (+) | (+) | (+/−) | (+) | (+) | (+) | (+) | (+) | (+) |

TABLE 8-4

PCR for detection of the lmo2736 gene, and halo formation

| primer set No. | F primer | R primer | Amplification size (bp) | \multicolumn{12}{c}{Bacterial strain No. (bacteria belonging to the genus *Listeria* other than the *monocytogenes* bacterium)} | | | | | | | | | | | |
|---|---|---|---|---|---|---|---|---|---|---|---|---|---|---|---|---|
| | | | | 11 | 12 | 13 | 14 | 15 | 16 | 17 | 18 | 19 | 20 | 21 | 22 |
| 1 | F8 | R176 | 168 | − | − | − | − | − | − | − | − | − | − | − | − |
| 3 | F222 | R591 | 369 | − | − | − | − | − | − | − | − | − | − | − | − |
| 4 | F488 | R591 | 103 | − | − | − | − | − | − | − | − | − | − | − | − |

TABLE 8-4-continued

PCR for detection of the lmo2736 gene, and halo formation

| primer set No. | F primer | R primer | Amplification size (bp) | Bacterial strain No. (bacteria belonging to the genus Listeria other than the monocytogenes bacterium) | | | | | | | | | | | |
|---|---|---|---|---|---|---|---|---|---|---|---|---|---|---|---|
| | | | | 11 | 12 | 13 | 14 | 15 | 16 | 17 | 18 | 19 | 20 | 21 | 22 |
| 5 | F488 | R685 | 197 | − | − | − | − | − | − | − | − | − | − | − | − |
| 6 | F488 | R771 | 283 | − | − | − | − | − | − | − | − | − | − | − | − |
| 9 | F530 | R685 | 185 | − | − | − | − | − | − | − | − | − | − | − | − |
| 10 | F530 | R771 | 241 | − | − | − | − | − | − | − | − | − | − | − | − |
| 12 | F530 | R992 | 462 | − | − | − | − | − | − | − | − | − | − | − | − |
| 13 | F572 | R685 | 113 | − | − | − | − | − | − | − | − | − | − | − | − |
| 14 | F572 | R771 | 198 | − | − | − | − | − | − | − | − | − | − | − | − |
| | Halo formation | | | (+) | (+) | (+) | (+) | (−) | (−) | (−) | (+) | (−) | (−) | (−) | (−) |

TABLE 9-1

| LMO 00084 | | | | | 23 Escherichia coli | 24 Salmonella subsp. enterica (I) | 25 Salmonella subsp. salamae (II) |
|---|---|---|---|---|---|---|---|
| No. | primer F | | primer: R | size | ATCC10798 | JA.107 | JA.125 |
| 6 | 286 | A | 757 | A | 471 | — | — | — |
| 8 | 286 | A | 757 | B | 471 | — | — | — |
| 14 | 286 | B | 757 | A | 471 | — | — | — |
| 16 | 286 | B | 757 | B | 471 | — | — | — |
| 2 | 281 | A | 757 | A | 476 | — | — | — |
| 4 | 281 | A | 757 | B | 476 | — | — | — |
| 10 | 281 | B | 757 | A | 476 | — | — | — |
| 12 | 281 | B | 757 | B | 476 | — | — | — |

| LMO 00084 No. | 26 Salmonella subsp. arizonae (IIIa) JA.76 | 27 Salmonella subsp. diarizinae (IIIb) JA.129 | 28 Salmonella subsp. houtenae JA.n-22 | 29 Salmonella bongori (V) JA.94 | 30 Salmonella subsp. enterica Typhimurium ATCC43971 | 31 Staphylococcus aureus ATCC6538P |
|---|---|---|---|---|---|---|
| 6 | — | — | — | — | — | — |
| 8 | — | — | — | — | — | — |
| 14 | — | — | — | — | — | — |
| 16 | — | — | — | — | — | — |
| 2 | — | — | — | — | — | — |
| 4 | — | — | — | — | — | — |
| 10 | — | — | — | — | — | — |
| 12 | — | — | — | — | — | — |

TABLE 9-2

| LMO 00084 | | | | | 32 Staphylococcus aureus | 33 Staphylococcus aureus | 34 Staphylococcus aureus |
|---|---|---|---|---|---|---|---|
| No. | primer F | | primer R | size | ATCC25923 | ATCC29213 | JMC2197 |
| 6 | 286 | A | 757 | A | 471 | — | — | — |
| 8 | 286 | A | 757 | B | 471 | — | — | — |
| 14 | 286 | B | 757 | A | 471 | — | — | — |
| 16 | 286 | B | 757 | B | 471 | — | — | — |
| 2 | 281 | A | 757 | A | 476 | — | — | — |
| 4 | 281 | A | 757 | B | 476 | — | — | — |
| 10 | 281 | B | 757 | A | 476 | — | — | — |
| 12 | 281 | B | 757 | B | 476 | — | — | — |

TABLE 9-2-continued

| LMO 00084 No. | 35 Staphylococcus aureus IMCB.IMA2 | 36 Staphylococcus cohnii ATCC29974 | 37 Staphylococcus haemolyticus ATCC29970 | 38 Staphylococcus hyicus subsp. ATCC11249 | 39 Staphylococcus intermedius ATCC29663 | 40 Staphylococcus saprophyticus ATCC15305 |
|---|---|---|---|---|---|---|
| 6  | — | — | — | — | — | — |
| 8  | — | — | — | — | — | — |
| 14 | — | — | — | — | — | — |
| 16 | — | — | — | — | — | — |
| 2  | — | — | — | — | — | — |
| 4  | — | — | — | — | — | — |
| 10 | — | — | — | — | — | — |
| 12 | — | — | — | — | — | — |

TABLE 9-3

| | LMO 00084 | | | | 41 Citrobacter freundii | 42 Citrobacter freundii |
|---|---|---|---|---|---|---|
| No. | primer: F | | primer: R | | size | ATCC8090 | ATCC8043 |
| 6  | 286 | A | 757 | A | 471 | — | — |
| 8  | 286 | A | 757 | B | 471 | — | — |
| 14 | 286 | B | 757 | A | 471 | — | — |
| 16 | 286 | B | 757 | B | 471 | — | — |
| 2  | 281 | A | 757 | A | 476 | — | — |
| 4  | 281 | A | 757 | B | 476 | — | — |
| 10 | 281 | B | 757 | A | 476 | — | — |
| 12 | 281 | B | 757 | B | 476 | — | — |

| LMO 00084 No. | 43 Proteus vulgaris IFO3988 | 44 Lactobacillus bulgaricus IFO13953 | 45 Lactobacillus helveticus IFO3809 | 46 Streptococcus sp. IFO3535 | 47 Streptococcus sanguis ATCC10558 | 48 Streptococcus mitis ATCC6249 |
|---|---|---|---|---|---|---|
| 6  | — | — | — | — | — | — |
| 8  | — | — | — | — | — | — |
| 14 | — | — | — | — | — | — |
| 16 | — | — | — | — | — | — |
| 2  | — | — | — | — | — | — |
| 4  | — | — | — | — | — | — |
| 10 | — | — | — | — | — | — |
| 12 | — | — | — | — | — | — |

TABLE 9-4

| | LMO 02736 | | | 23 Escherichia coli | 24 Salmonella subsp. enterica (I) | 25 Salmonella subsp. salamae (II) | 26 Salmonella subsp. arizonae (IIIa) | 27 Salmonella subsp. diarizinae (IIIb) |
|---|---|---|---|---|---|---|---|---|
| No. | primer:F | primer:R | size | ATCC10798 | JA. 107 | JA. 125 | JA. 76 | JA. 129 |
| 1  | 8   | 176 | 168 | — | — | — | — | — |
| 3  | 222 | 591 | 369 | — | — | — | — | — |
| 4  | 488 | 591 | 103 | — | — | — | — | — |
| 5  | 188 | 685 | 197 | — | — | — | — | — |
| 6  | 488 | 771 | 283 | — | — | — | — | — |
| 8  | 488 | 992 | 504 | — | — | — | — | — |
| 9  | 530 | 685 | 155 | — | — | — | — | — |
| 10 | 530 | 771 | 241 | — | — | — | — | — |
| 12 | 530 | 992 | 462 | — | — | — | — | — |
| 13 | 572 | 685 | 113 | — | — | — | — | — |
| 14 | 572 | 771 | 199 | — | — | — | — | — |

TABLE 9-4-continued

| | LMO 02736 No. | 28 Salmonella subsp. houtenae (IV) JA. n-22 | 29 Salmonella bongori (V) JA. 94 | 30 Salmonella subsp. enterica Typhimurium ATCC43971 | 31 Staphylococcus aureus ATCC6538P |
|---|---|---|---|---|---|
| | 1 | — | — | — | — |
| | 3 | — | — | — | — |
| | 4 | — | — | — | — |
| | 5 | — | — | — | — |
| | 6 | — | — | — | — |
| | 8 | — | — | — | — |
| | 9 | — | — | — | — |
| | 10 | — | — | — | — |
| | 12 | — | — | — | — |
| | 13 | — | — | — | — |
| | 14 | — | — | — | — |

TABLE 9-5

| LMO 02736 | | | 32 Staphylococcus aureus | 33 Staphylococcus aureus | 34 Staphylococcus aureus | 35 Staphylococcus aureus | 36 Staphylococcus cohnii |
|---|---|---|---|---|---|---|---|
| No. | primer:F | primer:R | size | ATCC25923 | ATCC29213 | JMC2197 | IMCB. IMA2 | ATCC29974 |
| 1 | 8 | 176 | 168 | — | — | — | — | — |
| 3 | 222 | 591 | 369 | — | — | — | — | — |
| 4 | 488 | 591 | 103 | — | — | — | — | — |
| 5 | 488 | 685 | 197 | — | — | — | — | — |
| 6 | 488 | 771 | 283 | — | — | — | — | — |
| 8 | 488 | 992 | 504 | — | — | — | — | — |
| 9 | 530 | 685 | 155 | — | — | — | — | — |
| 10 | 530 | 771 | 241 | — | — | — | — | — |
| 12 | 530 | 992 | 462 | — | — | — | — | — |
| 13 | 572 | 685 | 113 | — | — | — | — | — |
| 14 | 572 | 771 | 199 | — | — | — | — | — |

| | No. | 37 Staphylococcus haemolyticus ATCC29970 | 38 Staphylococcus hyicus subsp. ATCC11249 | 39 Staphylococcus intermedius ATCC29663 | 40 Staphylococcus saprophyticus ATCC15305 |
|---|---|---|---|---|---|
| | 1 | — | — | — | — |
| | 3 | — | — | — | — |
| | 4 | — | — | — | — |
| | 5 | — | — | — | — |
| | 6 | — | — | — | — |
| | 8 | — | — | — | — |
| | 9 | — | — | — | — |
| | 10 | — | — | — | — |
| | 12 | — | — | — | — |
| | 13 | — | — | — | — |
| | 14 | — | — | — | — |

TABLE 9-6

| LMO 02736 | | | 41 Citrobacter freundii | 42 Citrobacter freundii | 43 Proteus vulgaris | 44 Lactbacillus bulgarius | 45 Lactbacillus helveticus | 46 Streptococcus sp. | 47 Streptococcus sanguis | 48 Streptcoccus mitis |
|---|---|---|---|---|---|---|---|---|---|---|
| No. | primer: F | primer: R | size | ATCC8090 | ATCC8043 | IFO3988 | IFO13953 | IFO3809 | IFO3535 | ATCC10558 | ATCC6249 |
| 1 | 8 | 176 | 168 | — | — | — | — | — | — | — | — |
| 3 | 222 | 591 | 369 | — | — | — | — | — | — | — | — |
| 4 | 488 | 591 | 103 | — | — | — | — | — | — | — | — |
| 5 | 488 | 685 | 197 | — | — | — | — | — | — | — | — |
| 6 | 488 | 771 | 283 | — | — | — | — | — | — | — | — |
| 8 | 488 | 992 | 504 | — | — | — | — | — | — | — | — |
| 9 | 530 | 685 | 155 | — | — | — | — | — | — | — | — |
| 10 | 530 | 771 | 241 | — | — | — | — | — | — | — | — |

TABLE 9-6-continued

| | LMO 02736 | | | 41 Citrobacter freundii | 42 Citrobacter freundii | 43 Proteus vulgaris | 44 Lactbacillus bulgarius | 45 Lactbacillus helveticus | 46 Streptococcus sp. | 47 Streptococcus sanguis | 48 Streptcoccus mitis |
|---|---|---|---|---|---|---|---|---|---|---|---|
| No. | primer: F | primer: R | size | ATCC8090 | ATCC8043 | IFO3988 | IFO13953 | IFO3809 | IFO3535 | ATCC10558 | ATCC6249 |
| 12 | 530 | 992 | 462 | — | — | — | — | — | — | — | — |
| 13 | 572 | 685 | 113 | — | — | — | — | — | — | — | — |
| 14 | 572 | 771 | 199 | — | — | — | — | — | — | — | — |

<Designing of LAMP Primers>

LAMP primers were designed based on the primer set F286A/R757B, which targets the lmo0084 gene, and the primer set F530/R771, which targets the lmo2736 gene. For the designing of the primers, LAMP. Designer 1.14 (manufactured by OptiGene Limited), which is known support software for designing primers for the LAMP method, was used.

[Designing of LAMP Method Primers Targeting lmo0084]
1. The search region was entered as 1 to 984.
2. The range from F2 to B2 was entered as 150 to 300.
3. Sequences were predicted for the sets of F3/B3, F2/B2, and F1/B1 by the software.
4. Sets were selected such that one of F2 and B2 overlaps with the PCR primer F286A or R757B.
5. Optimization was carried out to select sets in which both F2 and B2 sequences overlap with the primers F286A and R757B.

[Designing of LAMP Method Primers Targeting lmo2736]
1. The search region was entered as 491 to 811.
2. The range from F2 to B2 was entered as 150 to 300.
3. The range from F1 to B1 was entered as 100 to 200.
4. Sequences were predicted for the sets of F3/B3, F21132, and F1/B1 by the software.
5. Sets were selected such that F2/B2 overlaps with the PCR primer F530 or R771.
6. The LAMP method was actually carried out with the designed primers, and optimization was carried out mainly for the F2/B2 selected.

The thus obtained LAMP primer sets for specific detection of the *monocytogenes* bacterium are shown below. The lmo0084 LAMP primer set was designed such that it reflects the genetic polymorphism in the serotype 1/2a of the *monocytogenes* bacterium. The lmo2736 LAMP primer sets were designed such that they reflect the genetic polymorphism in the serotype 1/2c of the *monocytogenes* bacterium except for SEQ ID NO:64. As a result of detection tests using the above bacterial strains, all of the primer sets were found to have specificity to the *monocytogenes* bacterium without being influenced by the genetic polymorphisms, as shown below in Table 14-1 to Table 14-3.

TABLE 10 lmo0084 LAMP primer set

| | Sequence (5' → 3') | SEQ ID No. | Setting position |
|---|---|---|---|
| LMO84 F3 | AAATGATTGAAGTCGTACGC | 42 | 104-123 |
| LMO84 B3 | GCAACCTCTTCAATTGGGATA | 43 | 384-404 |
| LMO84 FIP | CTAAAGCTTCTCCGACAAGTTCAATGGATGCAGGGATTAC<br>----*---*-*---*----- | 44 | 191-211 (F1)<br>128-146 (F2) |
| LMO84 BIP | AGAAACCATGTTCAAATTGCAAGAGCTTTCTGGACGGCTATC<br>*---------*-------- | 45 | 220-243 (B1)<br>283-300 (B2) |

SEQ ID NO: 58 shows the sequence of the F2 portion in the 3'-side of FIP, and SEQ ID NO: 59 shows the sequence of the B2 portion in the 3'-side of BIP. In the F2 portion and the B2 portion, * represents a base showing polymorphism based on comparison among the sequences of SEQ ID NOs: 1 to 25.

TABLE 11 lmo2736 LAMP primer set 1

| | Sequence (5' → 3') | SEQ ID NO. | Setting position |
|---|---|---|---|
| LMO2736-1 F3 | GAACTAGCCTACATTGATGC | 46 | 508-527 |
| LMO2736-1 B3 | TTGAACCGCTTAATAAGTCTG | 47 | 788-808 |

TABLE 11-continued lmo2736 LAMP primer set 1

| | Sequence (5' → 3') | SEQ ID NO. | Setting position |
|---|---|---|---|
| LMO2736-1 FIP | TTCGTCACGTCACAGGCTATCAGCAACCTTAACCCAAAG<br>------*-----*------ | 48 | 568-587 (F1)<br>528-546 (F2) |
| LMO2736-1 BIP | GGAGCAAAACTCGACCAATTTTCGTCCAGGAGCGATACCAC<br>----*------------- | 49 | 688-710 (B1)<br>752-769 (B2) |

SEQ ID NO: 60 shows the sequence of the F2 portion in the 3'-side of FIP, and SEQ ID NO: 61 shows the sequence of the B2 portion in the 3'-side of BIP. In the F2 portion and the B2 portion, * represents a base showing polymorphism based on comparison among the sequences of SEQ ID NOs: 1 to 25.

TABLE 12 lmo2736 LAMP primer set 2

| | Sequence (5' → 3') | SEQ ID NO. | Setting position |
|---|---|---|---|
| LMO2736-2 F3 | CAAGAACTAGCCTACATTGATG | 50 | 505-526 |
| LMO2736-2 B3 | TCTGCATTTAGGAAGGGCATT | 51 | 771-791 |
| LMO2736-2 FIP | TTCGTCACGTCACAGGCTATCAGCAACCTTAACCCAAAGC<br>------*-----*------ | 52 | 568-587 (F1)<br>528-547 (F2) |
| LMO2736-2 BIP | GGAGCAAAACTCGACCAATTTTC-GTCCAGCAGCGATACCAC<br>----*------------- | 53 | 688-710 (B1)<br>752-769 (B2) |

SEQ ID NO: 62 shows the sequence of the F2 portion in the 3'-side of FIP, and SEQ ID NO: 61 shows the sequence of the B2 portion in the 3'-side of BIP. In the F2 portion and the B2 portion, * represents a base showing polymorphism based on comparison among the sequences of SEQ ID NOs: 1 to 25.

TABLE 13 lmo2736 LAMP primer set 10

| | Sequence (5' → 3') | SEQ ID NO. | Setting position |
|---|---|---|---|
| LMO2736-10 F3 | GTGGCATTCATTTGCAAGAAC | 54 | 491-511 |
| LMO2736-10 B3 | GAGCTGAACCGCTTAATAAGTC | 55 | 790-811 |
| LMO2736-10 FIP | GAAGTGGATTCGTCACGTCACAGGCTACATTGATGCCAGCAACCTTAAC<br>*---*--------------*-----* | 56 | 572-595 (F1)<br>516-540 (F2) |
| LMO2736-10 BIP | CTCGACCAATTTTCTTCTCAAAAAATCACCACCAGCGGCTCCG<br>-----*--------* | 57 | 697-724 (B1)<br>741-755 (B2) |

SEQ ID NO: 63 shows the sequence of the F2 portion in the 3'-side of FIP, and SEQ ID NO: 64 shows the sequence of the B2 portion in the 3'-side of BIP. In the F2 portion and the B2 portion, * represents a base showing polymorphism based on comparison among the sequences of SEQ ID NOs: 1 to 25.

TABLE 14-1

| | *Listeria monocytogenes* | | | LMO2736 | | | |
|---|---|---|---|---|---|---|---|
| No. | Bacterial strain | | Halo | set 1 | set 2 | set 10 | LMO0084 |
| 1 | *L. monocytogenes* 1/2a | GTC02947 | (+) | + | + | + | + |
| 2 | *L. monocytogenes* 1/2b | GTC02948 | (+) | + | + | + | + |
| 3 | *L. monocytogenes* 1/2c | JMC7672 | (+) | + | + | + | + |
| 4 | *L. monocytogenes* 3g | JMC7673 | (+/−) | + | + | + | + |
| 5 | *L. monocytogenes* 3b | JMC7677 | (+) | + | + | + | + |
| 6 | *L. monocytogenes* 3c | JMC7678 | (+) | + | + | + | + |
| 7 | *L. monocytogenes* 4a | JMC7674 | (+) | + | + | + | + |

TABLE 14-1-continued

| | Listeria monocytogenes | | | LMO2736 | | | |
|---|---|---|---|---|---|---|---|
| No. | Bacterial strain | | Halo | set 1 | set 2 | set 10 | LMO0084 |
| 8 | L. monocytogenes 4b | JMC7675 | (+) | + | + | + | + |
| 9 | L. monocytogenes 4d | JMC7680 | (+) | + | + | + | + |
| 10 | L. monocytogenes 5 | GTC02957 | (+) | + | + | + | + |

TABLE 14-2

| | Bacteria belonging to the genus Listeria other than the monocytogenes bacterium | | | LMO2736 | | | |
|---|---|---|---|---|---|---|---|
| No. | Bacterial strain | | Halo | set 1 | set 2 | set 10 | LMO0084 |
| 11 | L. ivanovii | GTC02961 | (+) | − | − | − | − |
| 12 | L. ivanovii subsp. Ivanovii | JMC7681 | (+) | − | − | − | − |
| 13 | L. ivanovii subsp. Ivanovii | GTC01640T | (+) | − | − | − | − |
| 14 | L. ivanovii subsp. londoniensis | GTC01641 | (+) | − | − | − | − |
| 15 | L. innocua | GTC16426T | (−) | − | − | − | − |
| 16 | L. innocua | GTC02960 | (−) | − | − | − | − |
| 17 | L. welshimeri | GTC02963T | (−) | − | − | − | − |
| 18 | L. seeligeri | GTC16428T | (+) | − | − | − | − |
| 19 | L. grayi | GTC02964T | (−) | − | − | − | − |
| 20 | L. murrayi | GTC02964 | (−) | − | − | − | − |
| 21 | L. marthii | GTC16430T | (−) | − | − | − | − |
| 22 | L. rocourtiae | GTC16429T | (−) | − | − | − | − |

TABLE 14-3

| | Food-poisoning bacteria other than bacteria belonging to the genus Listeria | | LMO2736 | | | |
|---|---|---|---|---|---|---|
| No. | Bacterial strain | | set 1 | set 2 | set 10 | LMO0084 |
| 23 | Escherichia coli | ATCC10798 | — | — | — | — |
| 24 | Salmonella subsp.enterica (I) | JA.107 | — | — | — | — |
| 25 | Salmonella subsp.salamae (II) | JA.125 | — | — | — | — |
| 26 | Salmonella subsp.arizonae (IIIa) | JA.76 | — | — | — | — |
| 27 | Salmonella subsp.diarizinae (IIIb) | JA.129 | — | — | — | — |
| 28 | Salmonella subsp.houtenae (IV) | JA.n-22 | — | — | — | — |
| 29 | Salmonella bongori (V) | JA.94 | — | — | — | — |
| 30 | Salmonella subsp. enterica Typhimurium | ATCC43971 | — | — | — | — |
| 31 | Staphylococcus aureus | ATCC6538P | — | — | — | — |
| 32 | Staphylococcus aureus | ATCC25923 | — | — | — | — |
| 33 | Staphylococcus aureus | ATCC29213 | — | — | — | — |
| 34 | Staphylococcus aureus | JMC2197 | — | — | — | — |
| 35 | Staphylococcus aureus | IMCB.IMA2 | — | — | — | — |
| 36 | Staphylococcus colinti | ATCC29974 | — | — | — | — |
| 37 | Staphylococcus haemolyticus | ATCC29970 | — | — | — | — |
| 38 | Staphylococcus hyiens subsp. | ATCC11249 | — | — | — | — |
| 39 | Staphylococcus intermedius | ATCC29663 | — | — | — | — |
| 40 | Staphylococcus saprophyticus | ATCC15305 | — | — | — | — |
| 41 | Citrobacter freundii | ATCC8000 | — | — | — | — |
| 42 | Citrobacter freundii | ATCC8043 | — | — | — | — |
| 43 | Proteus vulgaris | IFO3988 | — | — | — | — |
| 44 | Lactobacillus bulgaricus | IFO13953 | — | — | — | — |
| 45 | Lactobacillus helveticus | IFO3809 | — | — | — | — |
| 46 | Streptococcus sp. | IF03535 | — | — | — | — |
| 47 | Streptococcus sanguis | ATCC10558 | — | — | — | — |
| 48 | Streptococcus mitis | ATCC6249 | — | — | — | — |

<Designing of Mixed Primers>

For covering polymorphic sequences of more serotypes, mixed primers using 5 mixed bases were designed at the LMO0084 primer designing sites shown above in Table 6.

TABLE 15

| LMO0084 primer | SEQ ID NO. | Sequence | Serotype |
|---|---|---|---|
| F286A | 26 | AGCCGTCCAGAAAGCATCAA | 1/2a, 1/2b, 1/2c, 3a, 3b, 3c, 4b, 4e |
| F286B | 27 | AGCCGCCCAGAAAGTCTCAA | 4a, 4c |
| F286/M | 67 | AGCCG<u>Y</u>CCAGAAAG<u>Y</u>MTCAA | |
| F281A | 28 | TCGATAGCCGTCCAGAAAGC | 1/2a, 1/2b, 1/2c, 3a, 3b, 3c, 4b, 4e |
| F281B | 29 | TTGATAGCCGCCCAGAAAGT | 4a, 4c |
| F281/M | 68 | T<u>Y</u>GATAGCCG<u>Y</u>CCAGAAAG<u>Y</u> | |
| R757A | 30 | GCTCGTCGGCGATTTCTTTC | 1/2a, 1/2c, 3a, 3c |
| R757B | 31 | GCTCGTCGGCTATTTCTTTC | 1/2b, 3b, 3c, 4a, 4b, 4e |

TABLE 15-continued

| LMO0084 primer | SEQ ID NO. | Sequence | Serotype |
|---|---|---|---|
| R757 | See 9 | GCTCGTCAGCTATTTCTTTC | 4c |
| R757/M | 69 | GCTCGTC<u>R</u>GC<u>K</u>ATTTCTTTC | |

Ordinary PCR was carried out with the combinations of F286/M and R757/M, and F281/M and R757/M, to see whether *monocytogenes*-specific amplification can be found therewith. Detection tests were carried out using the *monocytogenes* bacterial strains of the bacterial strain Nos. 1 to 10 shown in Table 5-1, the bacterial strains of the bacterial strain Nos. 11 to 22 belonging to the genus *Listeria* shown in Table 5-2, and the food-poisoning bacteria of the bacterial strain Nos. 23 to 48 (wherein, however, the *Citrobacter freundii* N-326 strain was used instead of the bacterial strain No. 42).

As a result, all *monocytogenes* bacteria showed amplification, and none of the bacterial strains other than the *monocytogenes* bacteria showed amplification (Tables 16-1 to 16-6).

TABLE 16-1

| | LMO0084 | | | 1 monocytogenes 1/2a | 2 monocytogenes 1/2b | 3 monocytogenes 1/2c | 4 monocytogenes 3a |
|---|---|---|---|---|---|---|---|
| No | primer: F | primer: R | size | | | | |
| 1 | F286/M | R757/M | 471 | + | + | + | + |
| 2 | F281/M | R757/M | 476 | + | + | + | + |

| | LMO0084 No | 5 monocytogenes 3b | 6 monocytogenes 3c | 7 monocytogenes 4a | 8 monocytogenes 4b | 9 monocytogenes 4d | 10 monocytogenes 5 |
|---|---|---|---|---|---|---|---|
| | 1 | + | + | + | + | + | + |
| | 2 | + | + | + | + | + | + |

TABLE 16-2

| | | LMO0084 | | 11 ivanovii | 12 ivanovii subsp. Ivanovii | 13 ivanovii subsp. Ivanovii | 14 ivanovii subsp. londoniensisi | 15 innocua |
|---|---|---|---|---|---|---|---|---|
| No. | primer: F | primer: R | size | GTC02961 | JMC7681 | GTC01640T | GTC01641 | GTC16426T |
| 1 | F286/M | R757/M | 471 | — | — | — | — | — |
| 2 | F281/M | R757/M | 476 | — | — | — | — | — |

| | | LMO0084 | | 16 innocua | 17 welshimeri | 18 seeligeri | 19 grayi | 20 murrayi |
|---|---|---|---|---|---|---|---|---|
| No. | primer: F | primer: R | size | GTC02960 | GTC02963T | GTC16428T | GTC02964T | GTC02964 |
| 1 | F286/M | R757/M | 471 | — | — | — | — | — |
| 2 | F281/M | R757/M | 476 | — | — | — | — | — |

TABLE 16-3

| | LMO0084 | | 21 *marthii* | 22 *rocourtiae* |
|---|---|---|---|---|
| No. | primer: F | primer: R | size | GTC16430T | GTC16429T |
| 1 | F286/M | R757/M | 471 | — | — |
| 2 | F281/M | R757/M | 476 | — | — |

TABLE 16-4

| | LMO0084 | | | 23 *Escherichia coli* (K12) | 24 *Salmonella* subsp. Enterica (I) | 25 *Salmonella* subsp. Salamae (II) | 26 *Salmonella* subsp. Arizonae (IIIa) | 27 *Salmonella* subsp. Diarizinae (IIIb) |
|---|---|---|---|---|---|---|---|---|
| No. | primer: F | primer: R | size | ATCC10798 | JA. 107 | JA. 125 | JA. 76 | JA. 129 |
| 1 | F286/M | R757/M | 471 | — | — | — | — | — |
| 2 | F281/M | R757/M | 476 | — | — | — | — | — |

| | LMO0084 | | | 28 *Salmonella* subsp. Houtenae (IV) | 29 *Salmonella bongori* (V) | 30 *Salmonella* subsp. Enterica Typhimurium | 31 *Staphylococcus aureus* | 32 *Staphylococcus aureus* |
|---|---|---|---|---|---|---|---|---|
| No. | primer: F | primer: R | size | JA. n-22 | JA. 94 | ATCC43971 | ATCC6538P | ATCC25923 |
| 1 | F286/M | R757/M | 471 | — | — | — | — | — |
| 2 | F281/M | R757/M | 476 | — | — | — | — | — |

TABLE 16-5

| | LMO0084 | | | 33 *Staphylococcus aureus* | 34 *Staphylococcus aureus* | 35 *Staphylococcus aureus* | 36 *Staphylococcus cohnii* | 40 *Staphylococcus saprophyticus* |
|---|---|---|---|---|---|---|---|---|
| No. | primer: F | primer: R | size | ATCC29213 | JMC2197 | IMCB. IMA2 | ATCC29974 | ATCC15305 |
| 1 | F286/M | R757/M | 471 | — | — | — | — | — |
| 2 | F281/M | R757/M | 476 | — | — | — | — | — |

| | LMO0084 | | | 37 *Staphylococcus haemolyticus* | 38 *Staphylococcus hyicus* subsp. | 39 *Staphylococcus intermedius* | 41 *Citrobacter freundii* | *Citrobacter freundii* |
|---|---|---|---|---|---|---|---|---|
| No. | primer: F | primer: R | size | ATCC29970 | ATCC11249 | ATCC29663 | ATCC8090 | N-326 |
| 1 | F286/M | R757/M | 471 | — | — | — | — | — |
| 2 | F281/M | R757/M | 476 | — | — | — | — | — |

TABLE 16-6

| | LMO0084 | | | 43 *Proteus vulgaris* | 44 *Lactbacillus bulgarius* | 45 *Lactbacillus helveticus* | 46 *Streptococcus* sp. | 47 *Streptcoccus sanguis* | 48 *Streptococcus mitis* |
|---|---|---|---|---|---|---|---|---|---|
| No. | primer: F | primer: R | size | IFO3988 | IFO13953 | IFO3809 | IFO3535 | ATCC10558 | ATCC6249 |
| 1 | F286/M | R757/M | 471 | — | — | — | — | — | — |
| 2 | F281/M | R757/M | 476 | — | — | — | — | — | — |

TABLE 17

| F/R | Position Primer abbreviations are shown in ( ) | Sequence | SEQ ID NO. | Serotype |
|---|---|---|---|---|
| F | 8-27 (F8) | TCGTCATCGCACCTGATTCA | 32 | 1/2a, 1/2b, 1/2c, 3a, 3b, 3c, 4a, 4b, 4c, 4d, 4e |
| F | 222-241 | GGCCTCCTACGGTATTCACG | 15 etc | 1/2c, 3a, 3c |
| F | 222-241 | GGCCCCCTACGGTATTCACA | 13 | 1/2a |
| F | 222-241 | GGCCTCTACGGTATTCACA | 19, 22 | 4a, 4c |
| F | 222-241 | GGCCTCCTACGGTATTCTCG | 14 etc | 1/2b, 3b, 4b, 4d, 4e |
| F | 222Mix (F222/M) | GGCCYCCTACGGTATTCWCR | 70 | |
| F | 488-507 | CCGGTGGCATTCATTTGCAA | 14 etc | 1/2b, 1/2c, 3b, 3c, 4a, 4b, 4c, 4d, 4e |
| F | 488-507 | CCGGCGGTATTCATTTGCAA | 13, 16 | 1/2a, 3a |
| F | 488Mix (F488/M) | CCGGYGGYATTCATTTGCAA | 71 | |
| F | 530-549 | GCAACCTTAACCCAAAGCTG | 15, 18 | 1/2c, 3c |
| F | 530-549 | GCAATCTTAACCCAAAGCTG | 13, 16 | 1/2a, 3a |
| F | 530-549 | GCAACCTTAATCCAAAGCTG | 14 etc | 1/2b, 3b, 4a, 4b, 4c, 4d, 4e |
| F | 530Mix (F530/M) | GCAAYCTTAAYCCAAAGCTG | 72 | |
| F | 572-591 | CCTGTGACGTGACGAATCCA | 13 etc | 1/2a, 1/2c, 3a, 3c |
| F | 572-591 | CCTGCGACGTCACGAATCCA | 14 etc | 1/2b, 3b, 4b, 4c, 4d, 4e |
| F | 572-591 | CCTGTGACGTCACGAATCCA | 19 | 4a |
| F | 572Mix (F572/M) | CCTGYGACGTSACGAATCCA | 73 | |
| R | 176-157 (R176) | TCCACCTCGGAAGACTCACT | 37 | 1/2a, 1/2b, 1/2c, 3a, 3b, 3c, 4a, 4b, 4c, 4d, 4e |
| R | 591-572 | TGGATTCGTGACGTCACAGG | 13 etc | 1/2a, 1/2c, 3a, 3c |
| R | 591-572 | TGGATTCGTGACGTCGCAGG | 14 etc | 1/2b, 3b, 4b, 4c, 4d, 4e |
| R | 591-572 | TGGATTCGTGACGTCACAGG | 19 | 4a |
| R | 591Mix (R591/M) | TGGATTCGTSACGTCRCAGG | 74 | |
| R | 685-666 | AGTTCTGCATGGCGTTCTCT | 13 etc | 1/2a, 1/2c, 3a, 3c |
| R | 685-666 | AGTTCTGCATGGCGCGCTCT | 14 etc | 1/2b, 3b, 4b, 4d, 4e |
| R | 685-666 | AGTTCTGCATGCCGTGCTCT | 19 | 4a |
| R | 685-666 | AGTTCTGCATGGCATGCTCT | 22 | 4c |
| R | 686Mix (R685/M) | AGTTCTGCATGGCRYKCTCT | 75 | |
| R | 771-752 | TAGTCCAGCAGCGATACCAC | 13 etc | 1/2a, 1/2c, 3a, 3c |
| R | 771-752 | TAGTCCGGCAGCGATACCAC | 14 etc | 1/2b, 3b, 4a, 4b, 4c, 4d, 4e |
| R | 771Mix (R771/M) | TAGTCCRGCAGCGATACCAC | 78 | |
| R | 992-973 (R992) | TTGTTTTCGAGTGCAAGGCT | 41 | 1/2a, 1/2b, 1/2c, 3a, 3b, 3c, 4a, 4b, 4c, 4d, 4e |

Ordinary PCR was carried out with the combinations of an F primer and an R primer shown below in Table 19 to see whether monocytogenes-specific amplification can be found therewith. Detection tests were carried out using the *mono-* cytogenes bacterial strains of the bacterial strain Nos. 1 to 10 shown in Table 5-1, the bacterial strains of the bacterial strain Nos. 11 to 22 belonging to the genus *Listeria* shown in Table 5-2, and the food-poisoning bacteria of the bacterial strain Nos. 23 to 48 (wherein, however, the *Citrobacter freundii* N-326 strain was used instead of the bacterial strain No. 42).

As a result, all *monocytogenes* bacteria showed amplification, and none of the bacterial strains other than the *monocytogenes* bacteria showed amplification (Tables 19-1 to 19-6).

TABLE 18

|    | LMO2736 F primer | LMO2736 R primer | Amplification size |
|----|------------------|------------------|--------------------|
| 1  | F8               | R176             | 168                |
| 2  | F222/M           | R591/M           | 369                |

TABLE 18-continued

|    | LMO2736 F primer | LMO2736 R primer | Amplification size |
|----|------------------|------------------|--------------------|
| 3  | F488/M           | R591/M           | 103                |
| 4  | F488/M           | R685/M           | 197                |
| 5  | F488/M           | R771/M           | 283                |
| 6  | F488/M           | R992             | 504                |
| 7  | F530/M           | R685/M           | 155                |
| 8  | F530/M           | R771/M           | 241                |
| 9  | F530/M           | R992             | 462                |
| 10 | F572/M           | R685/M           | 133                |
| 11 | F572/M           | R771/M           | 199                |
| 12 | F572/M           | R992             | 420                |

TABLE 19-1

| | LMO2736 | | | 1 *monocytogenes* 1/2a | 2 *monocytogenes* 1/2b | 3 *monocytogenes* 1/2c | 4 *monocytogenes* 3a | 5 *monocytogenes* 3b |
|---|---|---|---|---|---|---|---|---|
| No. | primer: F | primer: R | size | GTC02947 | GTC02948 | JMC7672 | JMC7673 | JMC7677 |
| 1  | F8     | R176   | 168 | + | + | + | + | + |
| 2  | F222/M | R591/M | 369 | + | + | + | + | + |
| 3  | F488/M | R591/M | 103 | + | + | + | + | + |
| 4  | F488/M | R685/M | 197 | + | + | + | + | + |
| 5  | F488/M | R771/M | 283 | + | + | + | + | + |
| 6  | F488/M | R992   | 504 | + | + | + | + | + |
| 7  | F530/M | R685/M | 155 | + | + | + | + | + |
| 8  | F530/M | R771/M | 241 | + | + | + | + | + |
| 9  | F530/M | R992   | 162 | + | + | + | + | + |
| 10 | F572/M | R685/M | 133 | + | + | + | + | + |
| 11 | F572/M | R771/M | 199 | + | + | + | + | + |
| 12 | F572/M | R992   | 420 | + | + | + | + | + |

| | LMO2736 | | | 6 *monocytogenes* 3c | 7 *monocytogenes* 4a | 8 *monocytogenes* 4b | 9 *monocytogenes* 4d | 10 *monocytogenes* 5 |
|---|---|---|---|---|---|---|---|---|
| No. | primer: F | primer: R | size | JMC7678 | JMC7674 | JMC7675 | JMC7680 | GTC02957 |
| 1  | F8     | R176   | 168 | + | + | + | + | + |
| 2  | F222/M | R591/M | 369 | + | + | + | + | + |
| 3  | F488/M | R591/M | 103 | + | + | + | + | + |
| 4  | F488/M | R685/M | 197 | + | + | + | + | + |
| 5  | F488/M | R771/M | 283 | + | + | + | + | + |
| 6  | F488/M | R992   | 504 | + | + | + | + | + |
| 7  | F530/M | R685/M | 155 | + | + | + | + | + |
| 8  | F530/M | R771/M | 241 | + | + | + | + | + |
| 9  | F530/M | R992   | 162 | + | + | + | + | + |
| 10 | F572/M | R685/M | 133 | + | + | + | + | + |
| 11 | F572/M | R771/M | 199 | + | + | + | + | + |
| 12 | F572/M | R992   | 420 | + | + | + | + | + |

TABLE 19-2

| | LMO2736 | | | 11 ivanovii | 12 ivanovii subsp. Ivanovii | 13 ivanovii subsp. Ivanovii | 14 ivanovii subsp. londoniensisi | 15 innocua |
|---|---|---|---|---|---|---|---|---|
| No. | primer: F | primer: R | size | GTC02961 | JMC7681 | GTC01640T | GTC01641 | GTC16426T |
| 1 | F8 | R176 | 168 | — | — | — | — | — |
| 2 | F222/M | R591/M | 369 | — | — | — | — | — |
| 3 | F488/M | R591/M | 103 | — | — | — | — | — |
| 4 | F488/M | R685/M | 197 | — | — | — | — | — |
| 5 | F488/M | R771/M | 283 | — | — | — | — | — |
| 6 | F488/M | R992 | 504 | — | — | — | — | — |
| 7 | F530/M | R685/M | 155 | — | — | — | — | — |
| 8 | F530/M | R771/M | 241 | — | — | — | — | — |
| 9 | F530/M | R992 | 462 | — | — | — | — | — |
| 10 | F572/M | R685/M | 133 | — | — | — | — | — |
| 11 | F572/M | R771/M | 199 | — | — | — | — | — |
| 12 | F572/M | R992 | 420 | — | — | — | — | — |

| | LMO2736 | | | 16 innocua | 17 welshimeri | 18 seeligeri | 19 grayi | 20 murrayi |
|---|---|---|---|---|---|---|---|---|
| No. | primer: F | primer: R | size | GTC02960 | GTC02963T | GTC16428T | GTC02964T | GTC02964 |
| 1 | F8 | R176 | 168 | — | — | — | — | — |
| 2 | F222/M | R591/M | 369 | — | — | — | — | — |
| 3 | F488/M | R591/M | 103 | — | — | — | — | — |
| 4 | F488/M | R685/M | 197 | — | — | — | — | — |
| 5 | F488/M | R771/M | 283 | — | — | — | — | — |
| 6 | F488/M | R992 | 504 | — | — | — | — | — |
| 7 | F530/M | R685/M | 155 | — | — | — | — | — |
| 8 | F530/M | R771/M | 241 | — | — | — | — | — |
| 9 | F530/M | R992 | 462 | — | — | — | — | — |
| 10 | F572/M | R685/M | 133 | — | — | — | — | — |
| 11 | F572/M | R771/M | 199 | — | — | — | — | — |
| 12 | F572/M | R992 | 420 | — | — | — | — | — |

TABLE 19-3

| | LMO2736 | | | 21 marthii | 22 rocourtiae |
|---|---|---|---|---|---|
| No. | primer: F | primer: R | size | GTC16430T | GTC16429T |
| 1 | F8 | R176 | 165 | — | — |
| 2 | F222/M | R591/M | 369 | — | — |
| 3 | F488/M | R591/M | 103 | — | — |
| 4 | F488/M | R885/M | 197 | — | — |
| 5 | F488/M | R771/M | 283 | — | — |
| 6 | F488/M | R992 | 504 | — | — |
| 7 | F530/M | R885/M | 155 | — | — |
| 8 | F530/M | R771/M | 241 | — | — |
| 9 | F530/M | R992 | 462 | — | — |
| 10 | F572/M | R685/M | 133 | — | — |
| 11 | F572/M | R771/M | 199 | — | — |
| 12 | F572/M | R992 | 420 | — | — |

TABLE 19-4

| | LMO2736 | | | 23 Escherichia coli (K12) | 24 Salmonella subsp. Enterica (I) | 25 Salmonella subsp. Salamae (II) | 26 Salmonella subsp. Arizonae (IIIa) | 27 Salmonella subsp. Diarizinae (IIIb) |
|---|---|---|---|---|---|---|---|---|
| No. | primer: F | primer: R | size | ATCC10798 | JA. 107 | JA. 125 | JA. 76 | JA. 129 |
| 1 | F8 | R176 | 168 | — | — | — | — | — |
| 2 | F222/M | R591/M | 369 | — | — | — | — | — |
| 3 | F488/M | R591/M | 103 | — | — | — | — | — |
| 4 | F488/M | R685/M | 197 | — | — | — | — | — |
| 5 | F488/M | R771/M | 283 | — | — | — | — | — |
| 6 | F488/M | R992 | 504 | — | — | — | — | — |
| 7 | F530/M | R685/M | 155 | — | — | — | — | — |
| 8 | F530/M | R771/M | 241 | — | — | — | — | — |
| 9 | F530/M | R992 | 462 | — | — | — | — | — |
| 10 | F572/M | R685/M | 133 | — | — | — | — | — |
| 11 | F572/M | R771/M | 199 | — | — | — | — | — |
| 12 | F572/M | R992 | 420 | — | — | — | — | — |

TABLE 19-4-continued

| | LMO2736 | | | 28 Salmonella subsp. Houtenae (IV) | 29 Salmonella bongori (V) | 30 Salmonella subsp. Enterica Typhimurium | 31 Staphylococcus aureus | 32 Staphylococcus aureus |
|---|---|---|---|---|---|---|---|---|
| No. | primer: F | primer: R | size | JA. n-22 | JA. 94 | ATCC43971 | ATCC6538P | ATCC25923 |
| 1 | F8 | R176 | 168 | — | — | — | — | — |
| 2 | F222/M | R591/M | 369 | — | — | — | — | — |
| 3 | F488/M | R591/M | 103 | — | — | — | — | — |
| 4 | F488/M | R685/M | 197 | — | — | — | — | — |
| 5 | F488/M | R771/M | 283 | — | — | — | — | — |
| 6 | F488/M | R992 | 504 | — | — | — | — | — |
| 7 | F530/M | R685/M | 155 | — | — | — | — | — |
| 8 | F530/M | R771/M | 241 | — | — | — | — | — |
| 9 | F530/M | R992 | 462 | — | — | — | — | — |
| 10 | F572/M | R685/M | 133 | — | — | — | — | — |
| 11 | F572/M | R771/M | 199 | — | — | — | — | — |
| 12 | F572/M | R992 | 420 | — | — | — | — | — |

TABLE 19-5

| | LMO2736 | | | 33 Staphylococcus aureus | 34 Staphylococcus aureus | 35 Staphylococcus aureus | 36 Staphylococcus aureus | 40 Staphylococcus aureus |
|---|---|---|---|---|---|---|---|---|
| No. | primer: F | primer: R | size | ATCC29213 | JMC2197 | IMCB. IMA2 | ATCC29974 | ATCC15305 |
| 1 | F8 | R176 | 168 | — | — | — | — | — |
| 2 | F222/M | R591/M | 369 | — | — | — | — | — |
| 3 | F488/M | R591/M | 103 | — | — | — | — | — |
| 4 | F488/M | R685/M | 197 | — | — | — | — | — |
| 5 | F488/M | R771/M | 283 | — | — | — | — | — |
| 6 | F488/M | R992 | 504 | — | — | — | — | — |
| 7 | F530/M | R685/M | 155 | — | — | — | — | — |
| 8 | F530/M | R771/M | 241 | — | — | — | — | — |
| 9 | F530/M | R992 | 462 | — | — | — | — | — |
| 10 | F572/M | R685/M | 133 | — | — | — | — | — |
| 11 | F572/M | R771/M | 199 | — | — | — | — | — |
| 12 | F572/M | R992 | 420 | — | — | — | — | — |

| | LMO2736 | | | 37 Staphylococcus aureus | 38 Staphylococcus cohnii | 39 Staphylococcus saprophyticus | 41 Citrobacter haemolyticus | Citrobacter hyicus subsp. |
|---|---|---|---|---|---|---|---|---|
| No. | primer: F | primer: R | size | ATCC29970 | ATCC11249 | ATCC29663 | ATCC8090 | N-326 |
| 1 | F8 | R176 | 168 | — | — | — | — | — |
| 2 | F222/M | R591/M | 369 | — | — | — | — | — |
| 3 | F488/M | R591/M | 103 | — | — | — | — | — |
| 4 | F488/M | R685/M | 197 | — | — | — | — | — |
| 5 | F488/M | R771/M | 283 | — | — | — | — | — |
| 6 | F488/M | R992 | 504 | — | — | — | — | — |
| 7 | F530/M | R685/M | 155 | — | — | — | — | — |
| 8 | F530/M | R771/M | 241 | — | — | — | — | — |
| 9 | F530/M | R992 | 462 | — | — | — | — | — |
| 10 | F572/M | R685/M | 133 | — | — | — | — | — |
| 11 | F572/M | R771/M | 199 | — | — | — | — | — |
| 12 | F572/M | R992 | 420 | — | — | — | — | — |

TABLE 19-6

| | LMO2736 | | 43 Proteus vulgaris | 44 Lactbacillus bulgarius | 45 Lactbacillus helveticus | 46 Streptococcus sp. | 47 Streptococcus sanguis | 48 Streptococcus mitis |
|---|---|---|---|---|---|---|---|---|
| No. | primer: F | primer: R | size | IFO3988 | IFO13953 | IFO3809 | IFO3535 | ATCC10558 | ATCC6249 |
| 1 | F8 | R176 | 168 | — | — | — | — | — | — |
| 2 | F222/M | R591/M | 369 | — | — | — | — | — | — |
| 3 | F488/M | R591/M | 103 | — | — | — | — | — | — |
| 4 | F488/M | R686/M | 197 | — | — | — | — | — | — |
| 5 | F488/M | R771/M | 283 | — | — | — | — | — | — |
| 6 | F488/M | R992 | 504 | — | — | — | — | — | — |
| 7 | F530/M | R685/M | 155 | — | — | — | — | — | — |
| 8 | F530/M | R771/M | 241 | — | — | — | — | — | — |
| 9 | F530/M | R992 | 462 | — | — | — | — | — | — |
| 10 | F572/M | R685/M | 133 | — | — | — | — | — | — |
| 11 | F572/M | R771/M | 199 | — | — | — | — | — | — |
| 12 | F572/M | R992 | 420 | — | — | — | — | — | — |

<Designing of TaqMan (Registered Trademark) Probes>

Aiming at construction of a real-time PCR detection system, TaqMan (registered trademark) probes were designed.

[1] LMO0084 Gene

A TaqMan (registered trademark) probe is commonly designed under the following conditions.

A TaqMan (registered trademark) probe is designed as a 20-mer to 30-mer probe (citation from Thermo Fisher).

The amplification target ideally has a length of 70 bp to 200 bp, and should have a length of less than 300 bp (citation from QIAGEN).

However, according to the sets of mixed primers targeting the LMO0084 gene, designed as described above (LMO0084-F286/M and LMO0084-8757/M. and LMO0084-F281/M and LMO0084-R757M), the length of the amplification target was about 470 bp. Since specificity in the PCR could not be obtained with a length shorter than this. TaqMan (registered trademark) probes were designed within this range. In the amplification target, 20-mer or longer sequences containing a common sequence of not more than two bases in the *monocytogenes* bacterium were present at three locations (Table 20).

TABLE 20

| Probe | Number of bases | Characteristics |
|---|---|---|
| TMP366-389 | 23 mer | Common to all sequences |
| TMP535-558 | 23 mer | TA-type and CC-type exist |
| TMP686-711 | 26 mer | Common to all sequences |

In view of this, the following four kinds of sequences were employed as probe sequences. The oligonucleotide having each sequence was modified with the fluorescent substance FAM (6-carboxyfluorescein) at the 5'-end, and with the quencher substance TAMRA at the 3'-end, to prepare a TaqMan (registered trademark) probe.

```
0084TMP366-389:
                                    (SEQ ID NO: 77)
TATTACATTCATAGAATTGACCC

0084TMP535-558(TA):
                                    (SEQ ID NO: 78)
ATCTGGTGGCGAGAAGCTGAAAA

0084TMP535-558(CC):
                                    (SEQ ID NO: 79)
ATCTGGTGGCGAGAAGCCGAACA

0084TMP686-711:
                                    (SEQ ID NO: 80)
TACCAAGATTCCAAAAAGAAGCCATG
```

The sets of mixed primers shown in Table 15 (LMO0084-F286M and LMO0084-R757M, and LMO0084-F281M and LMO0084-R757M) were used in combination with these TaqMan (registered trademark) probes to carry out detection experiments by real-time PCR using the genomes of test bacterial strains as templates. As the test bacterial strains, the *monocytogenes* bacterial strains of the bacterial strain Nos. 1 to 10 shown in Table 5-1, the bacterial strains of the bacterial strain Nos. 11 to 22 belonging to the genus *Listeria* shown in Table 5-2, and the food-poisoning bacteria of the bacterial strain Nos. 23 to 48 (wherein, however, the *Citrobacter freundii* N-326 strain was used instead of the bacterial strain No. 42) were used.

TABLE 21

[Composition of the reaction liquid for real-time PCR (total 20 μL)]

| | |
|---|---|
| Template DNA (1 ng/μL) | 1.00 μL |
| TaqMan Fast Advanced Master Mix(2x) | 10.00 μL |
| 100 μM Primer F | 0.08 μL (per primer sequence) |
| 100 μM Primer R | 0.08 μL (per primer sequence) |
| 100 μM TaqMan probe | 0.25 μL |
| Distilled Water | Appropriate volume |

[Reaction Conditions]

Apparatus used: Corbett Research: Roter-Gene6000

50° C. for 2 minutes (holding)→(95° C. for 2 minutes (holding)→(95° C. for 3 seconds −64° C. for 15 seconds)×40 cycles Evaluation was carried out based on the presence or absence of the amplification curve. At arose electrophoresis of the PCR product was also carried out, and the presence or absence of a band, and the band size were investigated.

The results of the real-time PCR tests are shown in Tables 22-1 to 22-3. 0084TMP366-389 and 0084TMP686-711 were capable of specific detection of the *monocytogenes* bacterium by combination with either primer set. 0084TMP535-558(TA) and 0084TMP535-558(CC) were found to be similarly capable of specific detection of the *monocytogenes* bacterium when they were used as a mixed probe. In cases where these are used as a mixture, the reaction liquid composition may be 0.25 μL of 100 μM 0084TMP535-558(TA) and 0.25 μL of 100 μM 0084TMP535-558(CC).

TABLE 22-1

| | LMO 0084 | | | TaqMan ® probe primer: F primer: R size | TMP366-389 — F286/M R757/M 471 | TMP535-558 TA F286/M R757/M 476 | TMP535-558 CC F286/M R757/M 476 | TMP535-558 Mix (TA/CC) F286/M R757/M 476 | TMP686-711 — F286/M R757/M 471 |
|---|---|---|---|---|---|---|---|---|---|
| 1 | Listeria monocytogenes | 1/2a | GTC02947 | | + | + | — | + | + |
| 2 | Listeria monocytogenes | 1/2b | GTC02948 | | + | + | — | + | + |
| 3 | Listeria monocytogenes | 1/2c | JMC7672 | | + | + | — | + | + |
| 4 | Listeria monocytogenes | 3a | JMC7673 | | + | + | — | + | + |
| 5 | Listeria monocytogenes | 3b | JMC7677 | | + | + | — | + | + |
| 6 | Listeria monocytogenes | 3c | JMC7678 | | + | + | — | + | + |
| 7 | Listeria monocytogenes | 4a | JMC7674 | | + | — | + | + | + |
| 8 | Listeria monocytogenes | 4b | JMC7675 | | + | + | — | + | + |
| 9 | Listeria monocytogenes | 4d | JMC7680 | | + | + | — | + | + |
| 10 | Listeria monocytogenes | 5 | GTC02957 | | + | + | — | + | + |

| | LMO 0084 | | | TaqMan ® probe primer: F primer: R size | TMP366-389 — F281/M R757/M 476 | TMP535-558 TA F281/M R757/M size | TMP535-558 CC F281/M R757/M 476 | TMP535-558 Mix (TA/CC) F281/M R757/M 476 | TMP686-711 — F281/M R757/M 476 |
|---|---|---|---|---|---|---|---|---|---|
| 1 | Listeria monocytogenes | 1/2a | GTC02947 | | + | + | — | + | + |
| 2 | Listeria monocytogenes | 1/2b | GTC02948 | | + | + | — | + | + |
| 3 | Listeria monocytogenes | 1/2c | JMC7672 | | + | + | — | + | + |
| 4 | Listeria monocytogenes | 3a | JMC7673 | | + | + | — | + | + |
| 5 | Listeria monocytogenes | 3b | JMC7677 | | + | + | — | + | + |
| 6 | Listeria monocytogenes | 3c | JMC7678 | | + | + | — | + | + |
| 7 | Listeria monocytogenes | 4a | JMC7674 | | + | — | + | + | + |
| 8 | Listeria monocytogenes | 4b | JMC7675 | | + | + | — | + | + |
| 9 | Listeria monocytogenes | 4d | JMC7680 | | + | + | — | + | + |
| 10 | Listeria monocytogenes | 5 | GTC02957 | | + | + | — | + | + |

TABLE 22-2

| | LMO 0084 | | TaqMan ® probe primer: F primer R size | TMP366-389 — F286/M R757/M 471 | TMP535-558 TA F286/M R757/M 471 | TMP535-558 CC F286/M R757/M 471 | TMP535-558 Mix (TA/CC) F286/M R757/M 471 | TMP686-711 — F286/M R757/M 471 |
|---|---|---|---|---|---|---|---|---|
| 11 | Listeria ivanovii | GTC02961 | | — | — | — | — | — |
| 12 | Listeria ivanovii subsp.Ivanovii | JMC7681 | | — | — | — | — | — |
| 13 | Listeria ivanovii subsp.Ivanovii | GTC01640T | | — | — | — | — | — |
| 14 | Listeria ivanovii subsp.londoniensisi | GTC01641 | | — | — | — | — | — |
| 15 | Listeria innocua | GTC16426T | | — | — | — | — | — |
| 16 | Listeria innocua | GTC02960 | | — | — | — | — | — |
| 17 | Listeria welshimeri | GTC02963T | | — | — | — | — | — |
| 18 | Listeria seeligeri | GTC16428T | | — | — | — | — | — |
| 19 | Listeria grayi | GTC02964T | | — | — | — | — | — |

TABLE 22-2-continued

| | | LMO 0084 | TaqMan ® probe primer: F primer R size | TMP366-389 — F281/M R757/M 476 | TMP535-558 TA F281/M R757/M 476 | TMP535-558 CC F281/M R757/M 476 | TMP535-558 Mix (TA/CC) F281/M R757/M 476 | TMP686-711 — F281/M R757/M 476 |
|---|---|---|---|---|---|---|---|---|
| 20 | Listeria murrayi | GTC02964 | | — | — | — | — | — |
| 21 | Listeria marthii | GTC16430T | | — | — | — | — | — |
| 22 | Listeria rocourtiae | GTC16429T | | — | — | — | — | — |
| 11 | Listeria ivanovii | GTC02961 | | — | — | — | — | — |
| 12 | Listeria ivanovii subsp.Ivanovii | JMC7681 | | — | — | — | — | — |
| 13 | Listeria ivanovii subsp.Ivanovii | GTC01640T | | — | — | — | — | — |
| 14 | Listeria ivanovii subsp.londoniensisi | GTC01641 | | — | — | — | — | — |
| 15 | Listeria innocua | GTC16426T | | — | — | — | — | — |
| 16 | Listeria innocua | GTC02960 | | — | — | — | — | — |
| 17 | Listeria welshimeri | GTC02963T | | — | — | — | — | — |
| 18 | Listeria seeligeri | GTC16428T | | — | — | — | — | — |
| 19 | Listeria grayi | GTC02964T | | — | — | — | — | — |
| 20 | Listeria murrayi | GTC02964 | | — | — | — | — | — |
| 21 | Listeria marthii | GTC16430T | | — | — | — | — | — |
| 22 | Listeria rocourtiae | GTC16429T | | — | — | — | — | — |

TABLE 22-3

| | | LMO 0084 | TaqMan ® probe primer: F primer: R size | TMP366-389 — F286/M R757/M 471 | TMP535-558 TA F286/M R757/M 471 | TMP535-558 CC F286/M R757/M 471 | TMP535-558 Mix (TA/CC) F286/M R757/M 471 | TMP686-711 — F286/M R757/M 471 |
|---|---|---|---|---|---|---|---|---|
| 23 | Escherichia coli (K12) | ATCC10798 | | — | — | — | — | — |
| 24 | Salmonella subsp. Enterica | JA.107 | | — | — | — | — | — |
| 25 | Salmonella subsp. Salamae | JA.125 | | — | — | — | — | — |
| 26 | Salmonella subsp. Arizonae | JA.76 | | — | — | — | — | — |
| 27 | Salmonella subsp. Diarizinae | JA.129 | | — | — | — | — | — |
| 28 | Salmonella subsp. Houtenae | JA.n-22 | | — | — | — | — | — |
| 29 | Salmonella bongori (V) | JA.94 | | — | — | — | — | — |
| 30 | Salmonella subsp. Enterica Typhimurium | ATCC43971 | | — | — | — | — | — |
| 31 | Staphylococcus aureus | ATCC6538P | | — | — | — | — | — |
| 32 | Staphylococcus aureus | ATCC25923 | | — | — | — | — | — |
| 33 | Staphylococcus aureus | ATCC29213 | | — | — | — | — | — |
| 34 | Staphylococcus aureus | JMC2197 | | — | — | — | — | — |
| 35 | Staphylococcus aureus | IMCB.IMA2 | | — | — | — | — | — |
| 36 | Staphylococcus cohnii | ATCC29974 | | — | — | — | — | — |
| 40 | Staphylococcus saprophyticus | ATCC15305 | | — | — | — | — | — |
| 37 | Staphylococcus haemolyticus | ATCC29970 | | — | — | — | — | — |
| 38 | Staphylococcus hyicus subsp. | ATCC11249 | | — | — | — | — | — |
| 39 | Staphylococcus intermedius | ATCC29663 | | — | — | — | — | — |
| 41 | Citrobacter freundii | ATCC8090 | | — | — | — | — | — |
| 43 | Citrobacter freundii | N-326 | | — | — | — | — | — |
| | Proteus vulgaris | IFO3988 | | — | — | — | — | — |
| 44 | Lactbacillus bulgarius | IFO13953 | | — | — | — | — | — |
| 45 | Lactbacillus helveticus | IFO3809 | | — | — | — | — | — |
| 46 | Streptococcus sp. | IFO3535 | | — | — | — | — | — |
| 47 | Streptococcus sanguis | ATCC10558 | | — | — | — | — | — |
| 48 | Streptococcus mitis | ATCC6249 | | — | — | — | — | — |

TABLE 22-3-continued

| | LMO 0084 | | TaqMan® probe primer: F primer: R size | TMP366-389 — F286/M R757/M 471 | TMP535-558 TA F286/M R757/M 471 | TMP535-558 CC F286/M R757/M 471 | TMP535-558 Mix (TA/CC) F286/M R757/M 471 | TMP686-711 — F286/M R757/M 471 |
|---|---|---|---|---|---|---|---|---|
| | LMO 0084 | | TaqMan® probe primer: F primer: R size | TMP366-389 — F281/M R757/M 476 | TMP535-558 TA F281/M R757/M 476 | TMP535-558 CC F281/M R757/M 476 | TMP535-558 Mix (TA/CC) F281/M R757/M 476 | TMP686-711 — F281/M R757/M 476 |
| 23 | *Escherichia coli* (K12) | ATCC10798 | — | — | — | — | — | |
| 24 | *Salmonella* subsp. Enterica | JA.107 | — | — | — | — | — | |
| 25 | *Salmonella* subsp. Salamae | JA.125 | — | — | — | — | — | |
| 26 | *Salmonella* subsp. Arizonae | JA.76 | — | — | — | — | — | |
| 27 | *Salmonella* subsp. Diarizinae | JA.129 | — | — | — | — | — | |
| 28 | *Salmonella* subsp. Houtenae | JA.n-22 | — | — | — | — | — | |
| 29 | *Salmonella bongori* (V) | JA.94 | — | — | — | — | — | |
| 30 | *Salmonella* subsp. Enterica Typhimurium | ATCC43971 | — | — | — | — | — | |
| 31 | *Staphylococcus aureus* | ATCC6538P | — | — | — | — | — | |
| 32 | *Staphylococcus aureus* | ATCC25923 | — | — | — | — | — | |
| 33 | *Staphylococcus aureus* | ATCC29213 | — | — | — | — | — | |
| 34 | *Staphylococcus aureus* | JMC2197 | — | — | — | — | — | |
| 35 | *Staphylococcus aureus* | IMCB.IMA2 | — | — | — | — | — | |
| 36 | *Staphylococcus cohnii* | ATCC29974 | — | — | — | — | — | |
| 40 | *Staphylococcus saprophyticus* | ATCC15305 | — | — | — | — | — | |
| 37 | *Staphylococcus haemolyticus* | ATCC29970 | — | — | — | — | — | |
| 38 | *Staphylococcus hyicus* subsp. | ATCC11249 | — | — | — | — | — | |
| 39 | *Staphylococcus intermedius* | ATCC29663 | — | — | — | — | — | |
| 41 | *Citrobacter freundii* | ATCC8090 | — | — | — | — | — | |
| 43 | *Citrobacter freundii* | N-326 | — | — | — | — | — | |
| | *Proteus vulgaris* | IFO3988 | — | — | — | — | — | |
| 44 | *Lactbacillus bulgarius* | IFO13953 | — | — | — | — | — | |
| 45 | *Lactbacillus helveticus* | IFO3809 | — | — | — | — | — | |
| 46 | *Streptococcus* sp. | IFO3535 | — | — | — | — | — | |
| 47 | *Streptococcus sanguis* | ATCC10558 | — | — | — | — | — | |
| 48 | *Streptococcus mitis* | ATCC6249 | — | — | — | — | — | |

Based on the above results, the following are primer-probe combinations that can be preferably used for detection of the LMO0084 gene by real-time PCR. The number in 1 (represents a SEQ ID NO. in SEQUENCE LISTING.

TABLE 23

| | LMO0084 primers | | LMO0084 |
|---|---|---|---|
| | primer: F | primer: R | TaqMan (registered trademark) probe |
| 1 | F286/M [67] | R757/M [69] | 0084TMP366-389 [77] |
| 2 | F286/M [67] | R757/M [69] | 0084TMP535-558(TA) [78] 0084TMP535-558(CC) [79] |
| 3 | F286/M [67] | R757/M [69] | 0084TMP686-711 [80] |
| 4 | F281/M [68] | R757/M [69] | 0084TMP366-389 [77] |
| 5 | F281/M [68] | R757/M [69] | 0084TMP535-558(TA) [78] 0084TMP535-558(CC) [79] |
| 6 | F281/M [68] | R757/M [69] | 0084TMP686-711 [80] |

[2] LMO2736 Gene

For each of No. 1 and No. 2 among the primer sets shown in Table 18, one TaqMan (registered trademark) probe was designed in the PCR amplification region (Table 24).

Since common sequences were hardly present in the PCR amplification of No. 3 to No. 12, a TaqMan (registered trademark) probe was set at one location in a common sequence in the PCR amplification regions of No. 4 to No. 12 (position 488 to position 992) (Table 24).

TABLE 24

| LMO0084 probe | Number of bases | Characteristics |
|---|---|---|
| TMP70-89 | 20 mer | Common to all sequences |
| TMP372-393 | 20 mer | Common to all sequences |
| TMP619-647 | 29 mer | GG-type and CC-type exist |

The following four kinds of sequences were employed as probe sequences. The oligonucleotide having each sequence was modified with the fluorescent substance FAM (6-carboxyfluorescein) at the 5'-end, and with the quencher substance TAMRA at the 3'-end, to prepare a TaqMan (registered trademark) probe.

2736TMP70-89:

(SEQ ID NO: 81)

AAAAAAGGCTGGACTAAAGC

-continued

2736TMP372-393:

(SEQ ID NO: 82)

ACGTCAAAAAAATCATTATC

2736TMP619-647(GG):

(SEQ ID NO: 83)

GTTTTCGGTGCTCAAAAAGGGGCAAGTCC

2736TMP619-647(CC):

(SEQ ID NO: 84)

GTTTTCGGTGCTCAAAAAGGCGCAACTCC

Real-time PCR tests were carried out using the combinations of primers and a probe shown below in Table 24. 2736TMP619-647(GG) and 2736TMP619-647(CC) were used individually or as a mixture to provide a probe. In the table, the number in [ ] represents a SEQ ID NO. in SEQUENCE LISTING. The test bacterial strains used, the composition of the reaction liquid for the real-time PCR, and the reaction conditions were the same as in the above detection tests for the LMO0084 gene. When 2736TMP619-647(SS) was used, the reaction liquid composition was 0.25 μL of 100 μM 2736TMP619-647(GG) and 0.25 μL of 100 μM 2736TMP619-647(CC).

TABLE 25

| | LMO2736 primers | | LMO2736 |
|---|---|---|---|
| | primer: F | primer: R | TaqMan (registered trademark) probe |
| 1 | F8 [32] | R176 [37] | 2736TMP70-89 [81] |
| 2 | F222/M [70] | R591/M [74] | 2736TMP372-393 [82] |
| 3 | F530/M [72] | R771/M [76] | 2736TMP619-647(GG) [83] |
| 4 | F530/M [72] | R771/M [76] | 2736TMP619-647(CC) [84] |
| 5 | F530/M [72] | R771/M [76] | 2736TMP619-647(GG) [83] 2736TMP619-647(CC) [84] |

The results are shown in Tables 26-1 to 26-3. The primer-probe sets 1 and 2 in Table 25 were capable of specific detection of the *monocytogenes* bacterium. 2736TMP619-647 (GG) and 2736TMP619-647 (CC) were capable of specific detection of the *monocytogenes* bacterium when they were used as a mixed probe. Based on the above results, 1, 2, and 5 in Table 25 are primer-probe combinations that can be especially preferably used for detection of the LMO2736 gene by real-time PCR.

TABLE 26-1

| | LMO 2736 | | TaqMan ® probe primer: F primer: R size | TMP70-89 — F8 R176 168 | TMP372-393 — F222/M R591/M 368 | TMP619-647 GG F530/M R771/M 241 | TMP619-617 CC F530/M R771/M 241 | TMP619-647 Mix (GG/CC) F530/M R771/M 241 |
|---|---|---|---|---|---|---|---|---|
| 1 | *Listeria monocytogenes* | 1/2a | GTC02947 | + | + | + | — | + |
| 2 | *Listeria monocytogenes* | 1/2b | GTC02948 | + | + | + | — | + |
| 3 | *Listeria monocytogenes* | 1/2c | JMC7672 | + | — | + | — | + |
| 4 | *Listeria monocytogenes* | 3a | JMC7673 | + | + | + | — | + |
| 5 | *Listeria monocytogenes* | 3b | JMC7677 | + | + | — | + | + |
| 6 | *Listeria monocytogenes* | 3c | JMC7678 | + | + | + | — | + |
| 7 | *Listeria monocytogenes* | 4a | JMC7674 | + | + | — | + | + |
| 8 | *Listeria monocytogenes* | 4b | JMC7675 | + | + | — | + | + |
| 9 | *Listeria monocytogenes* | 4d | JMC7680 | + | + | + | + | + |
| 10 | *Listeria monocytogenes* | | GTC02957 | + | + | — | + | + |

TABLE 26-2

| | LMO 2736 | TaqMan ® probe primer: F primer: R size | TMP70-89 — F8 R176 168 | TMP372-393 — F222/M R591/M 368 | TMP619-647 GG F530/M R771/M 241 | TMP619-647 CC F530/M R771/M 241 | TMP619-647 Mix (GG/CC) F530/M R771/M 241 |
|---|---|---|---|---|---|---|---|
| 11 | *Listeria ivanovii* | GTC02961 | — | — | — | — | — |
| 12 | *Listeria ivanovii* subsp. *Ivanovii* | JMC7681 | — | — | — | — | — |
| 13 | *Listeria ivanovii* subsp. *Ivanovii* | GTC01640T | — | — | — | — | — |
| 14 | *Listeria ivanovii* subsp. *londoniensisi* | GTC01641 | — | — | — | — | — |
| 15 | *Listeria innocua* | GTC16426T | — | — | — | — | — |
| 16 | *Listeria innocua* | GTC02960 | — | — | — | — | — |

TABLE 26-2-continued

|  | LMO 2736 | TaqMan® probe<br>primer: F<br>primer: R<br>size | TMP70-89<br>—<br>F8<br>R176<br>168 | TMP372-393<br>—<br>F222/M<br>R591/M<br>368 | TMP619-647<br>GG<br>F530/M<br>R771/M<br>241 | TMP619-647<br>CC<br>F530/M<br>R771/M<br>241 | TMP619-647<br>Mix (GG/CC)<br>F530/M<br>R771/M<br>241 |
|---|---|---|---|---|---|---|---|
| 17 | Listeria welshimeri | GTC02963T | — | — | — | — | — |
| 18 | Listeria seeligeri | GTC16428T | — | — | — | — | — |
| 19 | Listeria grayi | GTC02964T | — | — | — | — | — |
| 20 | Listeria murrayi | GTC02964 | — | — | — | — | — |
| 21 | Listeria marthii | GTC16430T | — | — | — | — | — |
| 22 | Listeria rocourtiae | GTC16429T | — | — | — | — | — |

TABLE 26-3

|  | LMO 2736 | TaqMan® probe<br>primer: F<br>primer: R<br>size | TMP70-89<br>—<br>F8<br>R176<br>168 | TMP372-393<br>—<br>F222/M<br>R591/M<br>368 | TMP619-647<br>GG<br>F530/M<br>R771/M<br>241 | TMP619-647<br>CC<br>F530/M<br>R771/M<br>241 | TMP619-647<br>Mix (GG/CC)<br>F530/M<br>R771/M<br>241 |
|---|---|---|---|---|---|---|---|
| 23 | Escherichia coli (K12) | ATCC10798 | — | — | — | — | — |
| 24 | Salmonella subsp. Enterica (I) | JA. 107 | — | — | — | — | — |
| 25 | Salmonella subsp. Salamae (II) | JA. 125 | — | — | — | — | — |
| 26 | Salmonella subsp. Arizonae (IIIa) | JA. 76 | — | — | — | — | — |
| 27 | Salmonella subsp. Diarizinae (IIIb) | JA. 129 | — | — | — | — | — |
| 28 | Salmonella subsp. Houtenae (IV) | JA. n-22 | — | — | — | — | — |
| 29 | Salmonella bongori (V) | JA. 94 | — | — | — | — | — |
| 30 | Salmonella subsp. EntericaTyphimuri | ATCC43971 | — | — | — | — | — |
| 31 | Staphylococcus aureus | ATCC6538P | — | — | — | — | — |
| 32 | Staphylococcus aureus | ATCC25923 | — | — | — | — | — |
| 33 | Staphylococcus aureus | ATCC29213 | — | — | — | — | — |
| 34 | Staphylococcus aureus | JMC2197 | — | — | — | — | — |
| 35 | Staphylococcus aureus | IMCB. IMA2 | — | — | — | — | — |
| 36 | Staphylococcus cohnii | ATCC29974 | — | — | — | — | — |
| 40 | Staphylococcus saprophyticus | ATCC15305 | — | — | — | — | — |
| 37 | Staphylococcus haemolyticus | ATCC29970 | — | — | — | — | — |
| 38 | Staphylococcus hyicus subsp. | ATCC11249 | — | — | — | — | — |
| 39 | Staphylococcus intermedius | ATCC29663 | — | — | — | — | — |
| 41 | Citrobacter freundii | ATCC8090 | — | — | — | — | — |
|  | Citrobacter freundii | N-326 | — | — | — | — | — |
| 43 | Proteus vulgaris | IFO3988 | — | — | — | — | — |
| 44 | Lactbacillus bulgarius | IFO13953 | — | — | — | — | — |
| 45 | Lactbacillus helveticus | IFO3809 | — | — | — | — | — |
| 46 | Streptcoccus sp. | IFO3535 | — | — | — | — | — |
| 47 | Streptcoccus sanguis | ATCC10558 | — | — | — | — | — |
| 48 | Streptcoccus mitis | ATCC6249 | — | — | — | — | — |

The following is an example of the procedure for preparation of a DNA sample in a case where a *monocytogenes* bacterium test is carried out for food using the present real-time PCR detection system.

(1) To 25 g of food, 225 mL of a bacterial growth selection medium is added, and culture is performed at 30° C. for 24 hours±3 hours. To 10 mL of BHI (Brain-Heart Infusion) medium, 0.1 mL of the resulting culture is added. Alternatively, a single colony on a selection agar medium is picked up, and then inoculated to 10 mL of BHI medium, followed by carrying out culture at 37° C. for 24 hours±3 hours.

(2) Centrifugation (13,000×g, 10 minutes, 20° C.) is carried out to collect bacterial cells from 1 mL of the resulting culture.

(3) DNA is extracted using a DNA extraction kit such as a mericon DNA Bacteria Plus Kit (QIAGEN: 69534).

(4) The DNA concentration is measured.

It was shown that, by this, *monocytogenes* can be specifically detected using a TaqMan (registered trademark) probe designed in the LMO0084 gene or the LMO2736 gene. By using a mixture of a plurality of TaqMan (registered trademark) probes taking polymorphic sequences of these genes into account, various serotypes of the *monocytogenes* bacterium can be comprehensively and specifically detected. The results shown in Table 22-1 and Table 26-1 indicate that, by designing a probe for targeting a polymorphism characteristic to a particular serotype, the *monocytogenes* bacterium can be detected specifically to the serotype, that is, serotype identification is possible. For example, 0084TMP535-558(CC) is a probe capable of specific detection of the serotype 4a. By designing new primers and probes from the regions in these two genes identified by the present inventors as target regions for specific detection of the *monocytogenes* bacterium, or from other regions, and appropriately combining these, identification of serotypes of the *monocytogenes* bacterium is possible.

The invention claimed is:

1. A loop-mediated isothermal amplification primer set for detection of *Listeria monocytogenes*, comprising any of the following sets:
   (i) a set of an F3 primer composed of the base sequence of SEQ ED NO:42, a B3 primer composed of the base sequence of SEQ ID NO:43, an FIP primer composed of the base sequence of SEQ ID NO:44, and a BIP primer composed of the base sequence of SEQ ID NO:45;
   (ii) a set of an F3 primer composed of the base sequence of SEQ ID NO:46, a B3 primer composed of the base sequence of SEQ ID NO:47, an FIP primer composed of the base sequence of SEQ ID NO:48, and a BIP primer composed of the base sequence of SEQ ID NO:49;
   (iii) a set of an F3 primer composed of the base sequence of SEQ ID NO:50, a B3 primer composed of the base sequence of SEQ ID NO:51, an FIP primer composed of the base sequence of SEQ ID NO:52, and a BIP primer composed of the base sequence of SEQ ID NO:53; and
   (iv) a set of an F3 primer composed of the base sequence of SEQ ID NO:54, a B3 primer composed of the base sequence of SEQ ID NO:55, an FIP primer composed of the base sequence of SEQ ID NO:56, and a BIP primer composed of the base sequence of SEQ ID NO:57.

2. A method of detecting *Listeria monocytogenes*, comprising a step of amplifying a partial region of lmo0084 gene or lmo2736 gene by a loop-mediated isothermal amplification method using the primer set according to claim 1.

* * * * *

UNITED STATES PATENT AND TRADEMARK OFFICE
CERTIFICATE OF CORRECTION

PATENT NO.         : 12,163,195 B2
APPLICATION NO.    : 18/505697
DATED              : December 10, 2024
INVENTOR(S)        : Mika Tsuna et al.

Page 1 of 1

It is certified that error appears in the above-identified patent and that said Letters Patent is hereby corrected as shown below:

In the Specification

<u>In Column 34, Line 28:</u>
Please change:
"FIG. 2-1 to FIG. 2-3"
To:
--FIG. 1-1 to FIG. 1-3--

Signed and Sealed this
Seventeenth Day of June, 2025

Coke Morgan Stewart
*Acting Director of the United States Patent and Trademark Office*